(12) United States Patent
Deng et al.

(10) Patent No.: US 12,397,029 B2
(45) Date of Patent: *Aug. 26, 2025

(54) USE OF MVA OR MVADELTAE3L AS IMMUNOTHERAPEUTIC AGENTS AGAINST SOLID TUMORS

(71) Applicant: Memorial Sloan Kettering Cancer Center, New York, NY (US)

(72) Inventors: Liang Deng, New York, NY (US); Jedd Wolchok, New York, NY (US); Taha Merghoub, New York, NY (US); Stewart Shuman, New York, NY (US); Peihong Dai, New York, NY (US); Weiyi Wang, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 656 days.

This patent is subject to a terminal disclaimer.

(21) Appl. No.: 17/575,462

(22) Filed: Jan. 13, 2022

(65) Prior Publication Data

US 2022/0211785 A1    Jul. 7, 2022

Related U.S. Application Data

(63) Continuation of application No. 16/741,634, filed on Jan. 13, 2020, now Pat. No. 11,253,560, which is a continuation of application No. 15/565,609, filed as application No. PCT/US2016/028184 on Apr. 18, 2016, now Pat. No. 10,548,930.

(60) Provisional application No. 62/149,484, filed on Apr. 17, 2015.

(51) Int. Cl.
| | |
|---|---|
| *A61K 35/768* | (2015.01) |
| *A61K 39/12* | (2006.01) |
| *A61K 39/395* | (2006.01) |
| *C07K 16/28* | (2006.01) |
| *A61K 39/00* | (2006.01) |

(52) U.S. Cl.
CPC ............ *A61K 35/768* (2013.01); *A61K 39/12* (2013.01); *A61K 39/3955* (2013.01); *C07K 16/2818* (2013.01); *C07K 16/2827* (2013.01); *A61K 2039/505* (2013.01); *A61K 2039/525* (2013.01); *A61K 2039/5254* (2013.01); *A61K 2039/54* (2013.01); *A61K 2039/545* (2013.01); *A61K 2039/57* (2013.01); *C12N 2710/24122* (2013.01); *C12N 2710/24132* (2013.01); *C12N 2710/24134* (2013.01); *C12N 2710/24171* (2013.01)

(58) Field of Classification Search
None
See application file for complete search history.

(56) References Cited

U.S. PATENT DOCUMENTS

| | | |
|---|---|---|
| 5,494,807 A | 2/1996 | Paoletti et al. |
| 5,762,938 A | 6/1998 | Paoletti et al. |
| 5,766,882 A | 6/1998 | Falkner et al. |
| 6,004,777 A | 12/1999 | Tartaglia et al. |
| 6,265,189 B1 | 7/2001 | Paoletti |
| 6,372,455 B1 | 4/2002 | Jacobs et al. |
| 6,475,999 B1 | 11/2002 | Mastrangelo et al. |
| 6,548,068 B1 | 4/2003 | Schlom et al. |
| 6,750,043 B2 | 6/2004 | Jacobs et al. |
| 6,761,893 B2 | 7/2004 | Chaplin et al. |
| 6,846,652 B2 | 1/2005 | Jacobs et al. |
| 6,942,855 B2 | 9/2005 | Jacobs et al. |
| 7,001,718 B2 | 2/2006 | Jacobs et al. |
| 7,049,145 B2 | 5/2006 | Erfle et al. |
| 7,208,313 B2 | 4/2007 | McCart et al. |
| 7,252,817 B2 | 8/2007 | Coffey et al. |
| 7,256,037 B2 | 8/2007 | Ellenhorn et al. |
| 7,306,902 B2 | 12/2007 | Thompson et al. |
| 7,431,929 B2 | 10/2008 | Jacobs et al. |
| 7,550,147 B2 | 6/2009 | Howley et al. |
| 7,588,767 B2 | 9/2009 | Szalay et al. |
| 7,807,146 B2 | 10/2010 | Delcayre et al. |
| 8,052,968 B2 | 11/2011 | Chen et al. |
| 8,105,578 B2 | 1/2012 | Roberts et al. |
| 8,377,688 B2 | 2/2013 | Delcayre et al. |
| 8,506,947 B2 | 8/2013 | Mccart et al. |
| 8,679,509 B2 | 3/2014 | Evans et al. |

(Continued)

FOREIGN PATENT DOCUMENTS

| | | |
|---|---|---|
| CA | 2435967 A1 | 1/2005 |
| CA | 2436196 A1 | 1/2005 |

(Continued)

OTHER PUBLICATIONS

Gómez CE, Perdiguero B, García-Arriaza J, Esteban M. Clinical applications of attenuated MVA poxvirus strain. Expert Rev Vaccines. Dec. 2013;12(12): 1395-416. (Year: 2013).*

(Continued)

*Primary Examiner* — Stacy B Chen
(74) *Attorney, Agent, or Firm* — ArentFox Schiff LLP; Daniel W. Clarke; Shawn P. Foley, Esq

(57) ABSTRACT

The present disclosure relates to modified vaccinia Ankara (MVA) virus or MVAΔE3L delivered intratumorally or systemically as an anticancer immunotherapeutic agent, alone, or in combination with one or more immune checkpoint blocking agents for the treatment of malignant solid tumors. Particular embodiments relate to mobilizing the host's immune system to mount an immune response against the tumor.

13 Claims, 32 Drawing Sheets

Specification includes a Sequence Listing.

(56) References Cited

U.S. PATENT DOCUMENTS

| | | |
|---|---|---|
| 8,747,837 B2 | 6/2014 | Kirn et al. |
| 8,778,328 B2 | 7/2014 | Erbs et al. |
| 8,852,927 B2 | 10/2014 | Szalay et al. |
| 8,859,256 B2 | 10/2014 | Szalay et al. |
| 8,865,153 B2 | 10/2014 | Szalay et al. |
| 8,871,219 B2 | 10/2014 | Heeney et al. |
| 9,101,658 B2 | 8/2015 | Contag et al. |
| 9,132,281 B2 | 9/2015 | Zeng et al. |
| 9,175,057 B2 | 11/2015 | Schlom et al. |
| 9,180,150 B2 | 11/2015 | Erbs et al. |
| 9,234,197 B2 | 1/2016 | Chaput et al. |
| 9,273,327 B2 | 3/2016 | Cottingham |
| 9,670,506 B2 | 6/2017 | Pantaleo et al. |
| 9,879,281 B2 | 1/2018 | Son et al. |
| 9,919,062 B2 | 3/2018 | Kirn |
| 10,512,662 B2 | 12/2019 | Deng et al. |
| 10,548,930 B2* | 2/2020 | Deng ............ A61P 35/00 |
| 10,639,366 B2 | 5/2020 | Deng et al. |
| 10,736,962 B2* | 8/2020 | Deng ............ A61P 35/00 |
| 10,765,711 B2 | 9/2020 | Deng et al. |
| 11,253,560 B2* | 2/2022 | Deng ............ A61P 43/00 |
| 11,285,209 B2* | 3/2022 | Deng ............ A61K 9/0019 |
| 11,541,087 B2 | 1/2023 | Deng et al. |
| 11,986,503 B2 | 5/2024 | Deng et al. |
| 12,036,279 B2* | 7/2024 | Deng ............ A61P 35/00 |
| 2002/0061298 A1 | 5/2002 | Coffey et al. |
| 2002/0155529 A1 | 10/2002 | Jacobs et al. |
| 2003/0113919 A1 | 6/2003 | Emtage et al. |
| 2004/0091995 A1 | 5/2004 | Schlom et al. |
| 2004/0208850 A1 | 10/2004 | Ellenhorn et al. |
| 2005/0028226 A1* | 2/2005 | Erfle ............ C12N 7/00 435/325 |
| 2005/0287162 A1 | 12/2005 | Baier et al. |
| 2006/0088909 A1 | 4/2006 | Compans et al. |
| 2006/0099181 A1 | 5/2006 | Jacobs et al. |
| 2006/0216312 A1 | 9/2006 | Jacobs |
| 2007/0036758 A1 | 2/2007 | Jacobs et al. |
| 2007/0178065 A1 | 8/2007 | Lattime et al. |
| 2007/0275010 A1 | 11/2007 | Feinberg et al. |
| 2008/0075694 A1 | 3/2008 | Drexler et al. |
| 2008/0181870 A1 | 7/2008 | Lowenstein et al. |
| 2009/0162288 A1 | 6/2009 | Chen et al. |
| 2010/0247622 A1 | 9/2010 | Coffey et al. |
| 2010/0316609 A1 | 12/2010 | Dewhurst et al. |
| 2011/0064650 A1 | 3/2011 | Szalay |
| 2011/0142874 A1 | 6/2011 | Jacobs et al. |
| 2011/0206640 A1 | 8/2011 | Bell et al. |
| 2012/0308484 A1 | 12/2012 | Szalay et al. |
| 2012/0328649 A1 | 12/2012 | Falkner et al. |
| 2013/0195912 A1 | 8/2013 | Cottingham |
| 2013/0243813 A1 | 9/2013 | Howley et al. |
| 2013/0295675 A1 | 11/2013 | Jacobs et al. |
| 2014/0086976 A1 | 3/2014 | Szalay et al. |
| 2014/0087362 A1 | 3/2014 | Szalay et al. |
| 2014/0193859 A1 | 7/2014 | Jacobs et al. |
| 2014/0271549 A1 | 9/2014 | Szalay |
| 2014/0377870 A1 | 12/2014 | Jacobs et al. |
| 2015/0037355 A1 | 2/2015 | Kirn et al. |
| 2015/0202272 A1 | 7/2015 | Lauterbach et al. |
| 2015/0240246 A1 | 8/2015 | Jacobs et al. |
| 2015/0250837 A1 | 9/2015 | Nolin et al. |
| 2015/0250869 A1 | 9/2015 | Sene et al. |
| 2015/0283220 A1 | 10/2015 | Mandl et al. |
| 2016/0008479 A1 | 1/2016 | Antony |
| 2016/0130564 A1 | 5/2016 | Marais et al. |
| 2016/0185875 A1 | 6/2016 | Univ. |
| 2016/0235793 A1 | 8/2016 | Thorne |
| 2016/0271239 A1* | 9/2016 | Foy ............ A61K 39/001193 |
| 2016/0339090 A1 | 11/2016 | Hacohen et al. |
| 2017/0020938 A1 | 1/2017 | Wang et al. |
| 2017/0021009 A1 | 1/2017 | Jacobs et al. |
| 2017/0106065 A1 | 4/2017 | Foy et al. |
| 2017/0143780 A1 | 5/2017 | Zitvogel et al. |
| 2017/0157188 A1 | 6/2017 | Silvestre et al. |
| 2017/0246280 A1 | 8/2017 | Pantaleo et al. |
| 2017/0266270 A1 | 9/2017 | Foy et al. |
| 2017/0340687 A1 | 11/2017 | Nakao et al. |
| 2022/0056475 A1 | 2/2022 | Deng et al. |
| 2023/0057304 A1* | 2/2023 | Deng ............ A61K 39/3955 |

FOREIGN PATENT DOCUMENTS

| | | |
|---|---|---|
| CN | 1842602 A | 10/2006 |
| CN | 105039269 A | 11/2015 |
| CN | 106456747 A | 2/2017 |
| CN | 107735103 A | 2/2018 |
| CN | 109152827 A | 1/2019 |
| DE | 10144664.9 A1 | 6/2005 |
| EP | 2 771 465 A1 | 5/2013 |
| EP | 2 136 633 B1 | 10/2015 |
| EP | 3 142 690 A2 | 4/2017 |
| EP | 3 850 103 A1 | 7/2021 |
| JP | 2005-502360 A | 1/2005 |
| JP | 2006-512097 A | 4/2006 |
| JP | 2010-521497 A | 6/2010 |
| JP | 5690214 B2 | 3/2015 |
| WO | WO-03/023040 A2 | 3/2003 |
| WO | WO-2003/088994 | 10/2003 |
| WO | WO-2004/024756 A2 | 3/2004 |
| WO | WO-2004/058801 A2 | 7/2004 |
| WO | WO-2004/003987 A1 | 8/2004 |
| WO | WO-2006/120474 A2 | 11/2006 |
| WO | WO-2007/119895 A1 | 10/2007 |
| WO | WO-2007/126805 A2 | 11/2007 |
| WO | WO-2008/045346 A2 | 4/2008 |
| WO | WO-2008/113078 A1 | 9/2008 |
| WO | WO-2009/152179 A1 | 12/2009 |
| WO | WO-2011/156470 A1 | 12/2011 |
| WO | WO-2012/009644 A2 | 1/2012 |
| WO | WO-2013/038066 A1 | 3/2013 |
| WO | WO-2014/036412 A2 | 3/2014 |
| WO | WO-2014/081976 A1 | 5/2014 |
| WO | WO-2015/066715 A1 | 5/2015 |
| WO | WO-2015/069571 A1 | 5/2015 |
| WO | WO-2015/084897 A2 | 6/2015 |
| WO | WO-2015/138741 A1 | 9/2015 |
| WO | WO-2016/008976 A1 | 1/2016 |
| WO | WO-2016/046357 A1 | 3/2016 |
| WO | WO-2016/128542 A1 | 8/2016 |
| WO | WO-2016/144564 A1 | 9/2016 |
| WO | WO-2016/144564 A2 | 9/2016 |
| WO | WO-2016/168862 A1 | 10/2016 |
| WO | WO-2016/205429 A1 | 12/2016 |
| WO | WO-2017/024000 A1 | 2/2017 |
| WO | WO-2017/037523 A1 | 3/2017 |
| WO | WO-2017/043815 A1 | 3/2017 |
| WO | WO-2017/044780 A1 | 3/2017 |
| WO | WO-2017/075570 A1 | 5/2017 |
| WO | WO-2017/103291 A1 | 6/2017 |
| WO | WO-2017/129765 A1 | 8/2017 |
| WO | WO-2017/147553 A2 | 8/2017 |
| WO | WO-2017/147554 A1 | 8/2017 |
| WO | WO-2017/147554 A2 | 8/2017 |
| WO | WO-2017/156349 A1 | 9/2017 |
| WO | WO-2017/205674 A1 | 11/2017 |
| WO | WO-2018/015448 A1 | 1/2018 |
| WO | WO-2018/016917 A1 | 1/2018 |
| WO | WO-2018/017747 A2 | 1/2018 |
| WO | WO-2018/031694 A1 | 1/2018 |
| WO | WO-2018/049248 A1 | 3/2018 |
| WO | WO-2018/057755 A1 | 3/2018 |
| WO | WO-2018/058258 A1 | 4/2018 |

OTHER PUBLICATIONS

Carroll et al., "Highly attenuated modified vaccinia virus Ankara (MVA) as an effective recombinant vector:a Murine tumor model", Vaccine, 15(4), pp. 387-394, 31.

Greiner et al., "The blockade of immune checkpoints in cancer immunotherapy", Nat Rev Cancer, 12(4), pp. 252-264, Mar. 22, 2012 (Mar. 22, 2012).

Liu Z, Zhou H, Wang W, Fu YX, Zhu M. A novel dendritic cell targeting HPV16 E7 synthetic vaccine in combination with PD-L1

(56) References Cited

OTHER PUBLICATIONS blockade elicits therapeutic antitumor immunity in mice. Oncoimmunology. Mar. 10, 2016;5(6):e1147641. doi: 10.1080/2162402X. 2016.1147641. PMID: 27471615; PMCID: PMC4938372. (Year: 2016).
Terawaki S, Chikuma S, Shibayama S, Hayashi T, Yoshida T, Okazaki T, Honjo T. IFN-a directly promotes programmed cell death- 1 transcription and limits the duration of T cell-mediated immunity. J Immunol. Mar. 1, 2011; 186(5):2772-9. (Year: 2011).
Yang, et al., "Vaccinia E5 is a major inhibitor of the DNA sensor cGAS." BioRxiv, Oct. 26, 2021, 45 pages.
Yang, et al., "Intratumoral delivery of engineered recombinant modified vaccinia virus Ankara expressing Flt3L and OX40L generates potent antitumor immunity through activating the cGAS/STING pathway and depleting tumor-infiltrating regulatory T cells." BioRxiv, Nov. 1, 2021, 53 pages.
Yang, et al., "Vaccinia virus E5 is a dominant inhibitor of the cytosolic DNA sensor cGAS." J. of Immunol., May 1, 2019, vol. 202, No. 1 Suppl., p. 197.8.
Alharbi, et al., "ChAdOx1 and MVA based vaccine candidates against MERS-CoV elicit neutralising antibodies and cellular immune responses in mice," Vaccine, vol. 35, pp. 3780-3788 (Jun. 27, 2017).
Angell et al., "From the immune contexture to the Immunoscore: the role of prognostic and predictive immune markers in cancer," Curr. Opin. Immunol., 25, pp. 261-267 (2013).
Antoine et al., "The complete genomic sequence of the modified vaccinia Ankara strain: comparison with other orthopoxviruses", Virology, 244, pp. 365-396 (1998).
Arsenio et al., "Antagonizing activity of vaccinia virus E3L against human interferons in Huh7 cells," Journal of Virology, vol. 377, No. 1, p. 124-132 (Jul. 20, 2008).
Backes et al., "Viral host-range factor C7 or K1 is essential for modified vaccinia virus Ankara late gene expression in human and murine cells, irrespective of their capacity to inhibit protein kinase R- mediated phosphorylation of eukaryotic translation initiation factor 2a," J. of General Virology, vol. 91, pp. 470-482 (Feb. 1, 2010).
Barber, "Innate immune DNA sensing pathways: STING, AIMII and the regulation of interferon production and inflammatory responses", Curr. Opin. Immunol., 23, pp. 10-20 (2011).
Benci et al., "Tumor Interferon Signaling Regulates a Multigenic Resistance Program to Immune Checkpoint Blockade." Cell. Dec. 1, 2016; 167(6): 1540-1554.e12.
Bisht et al., "Severe acute respiratory syndrome coronavirus spike protein expressed by attenuated vaccinia virus protectively immunizes mice," PNAS, vol. 101, pp. 6641-6646 (Apr. 27, 2004).
Bommareddy et al., "MEK inhibition enhances oncolytic virus immunotherapy through increased tumor cell killing and T cell activation," Science Translational Medicine, vol. 10, Issue 471 (Dec. 12, 2018).
Brandler et al., "Preclinical studies of a modified vaccinia virus Ankara-based HIV candidate vaccine: antigen presentation and antiviral effect", J. Virol., vol. 84, No. 10, pp. 5314-5328 (2010).
Brandt et al., "The N-terminal domain of the vaccinia virus E3L-protein is required for neurovirulence" Virology, vol. 333, No. 2, pp. 263-270 (Mar. 15, 2005).
Breitbach et al., "Targeted and armed oncolytic poxviruses for cancer: the lead example of JX-594," Current Pharmaceutical Biotechnology, 13, pp. 1768-1772 (2012).
Brinkman et al., "Fingolimod (FTY720): discovery and development of an oral drug to treat multiple sclerosis," Nature Reviews | Drug Discovery, vol. 9, pp. 883-897 (Nov. 2010).
Caisova et al., "Innate immunity based cancer immunotherapy: B16-F10 murine melanoma model," BMC Cancer, 16:940, 11 pages (2016).
Cao et al., "Innate immune response of human plasmacytoid dendritic cells to poxvirus infection is subverted by vaccinia E3 via its Z-DNA/RNA binding domain," PLOS ONE, vol. 7, No. 5, p. e36823 (May 14, 2012).

Carina Riediger et al:Fms-like tyrosine kinase 3 receptor ligand (Flt3L)-based vaccination administered with an adenoviral vector prevents tumor growth of colorectal cancer in a BALB/c mouse model 11, Journal of Cancer Research and Clinical Oncology., vol. 139, No. 12, Oct. 10, 2013 (Oct. 10, 2013), pp. 2097-2110, XP055672630, DE ISSN: 0171-5216, DOI: 10.1007/s00432-013-1532-z Figures 6, 8.
Castle et al., "Exploiting the mutanome for tumor vaccination", Cancer Res., 72, pp. 1081-1091 (2012).
Chafekar, et al., "MERS-CoV: Understanding the Latest Human Coronavirus Threat," Viruses, 10, 93, 22 pages (Feb. 24, 2018).
Chavan et al., "Expression of CCL20 and granulocyte-macrophage colony-stimulating factor, but not Flt3-L, from modified vaccinia virus Ankara enhances antiviral cellular and humoral immune responses," J. Virology, vol. 80, No. 15, pp. 7676-7687 (2006).
Chi et al., "DNA vaccine encoding Middle East respiratory syndrome coronavirus S1 protein induces protective immune responses in mice," Vaccine, vol. 35, pp. 2069-2075 (Apr. 11, 2017).
Coffey et al., "Reovirus therapy of tumors with activated Ras pathway," Science, 282, pp. 1332-1334 (1998).
Curran et al., Tumor Vaccines Expressing Flt2 Ligand Synergize with CTLA-4 Blockade to Reject Preimplanted Tumors, Cancer Research vol. 69 No. 19, Sep. 8, 2009, pp. 7747-7755.
Dai et al., "Abstract B031: Heat-inactivated modified vaccinia virus Ankara induces type I IFN and antitumor immunity via the cytosolic DNA-sensing pathway," retrieved from: http://www.cancerimmunolrres.aacrjournals.org/content/4/1_Supplement/B031 (Jun. 15, 2018).
Dai et al., "Intratumoral delivery of inactivated modified vaccinia virus Ankara (iMVA) induces systemic antitumor immunity via STING and Batf3-dependent dendritic cells" Science Immunology, vol. 2, No. 11, pp. 1-34 (May 19, 2017).
Dai, P et al., Modified Vaccinia Virus Ankara Triggers Type 1 IFN Production in Murine Conventional Dendritic Cells via a cGAS/STING-Mediated Cytosolic DNA-Sensing Pathway, PLOS Pathogens, Apr. 2014, vol. 10, pp. 1-13.
Dai, P et al., Myxoma Virus Induces Type 1 Interferon Production in Murine Plasmacytoid Dendritic Cells via a TLR9/MyD88-, IRF5/IRF7-, and IFNAR-Dependent Pathway. Journal of Virology, Oct. 2011, pp. 10814-10825.
Deng et al., "STING-Dependent Cytosolic DNA Sensing Promotes Radiation-Induced Type I Interferon-Dependent Antitumor Immunity in Immunogenic Tumors", Immunity, vol. 41, No. 5, pp. 843-852 (2014).
Deng et al., "Vaccinia virus infection attenuates innate immune responses and antigen presentation by epidermal dendritic cells", J Virol., 80, pp. 9977-9987 (2006).
Diamond et al., "Type I interferon is selectively required by dendritic cells for immune rejection of tumors", J Exp Med., vol. 208, No. 10, pp. 1989-2003 (2011).
Drexler et al., "Modified Vaccinia Virus Ankara for Delivery of Human Tyrosinase as Melanomaassociated Antigen: Induction of Tyrosinase- and Melanoma-specific Human Leukocyte Antigen A*0201-restricted Cytotoxic T Cells in Vitro and in Vivo1," Cancer Research, vol. 59, p. 4955-4963 (Oct. 1, 99).
Drillien et al, Modified vaccination virus Ankara induces moderate activation of human dendritic cells, Journal of General Virology, Society for General Microbiology, vol. 85, No. Pt 8, Aug. 1, 2004, pp. 2167-2175.
Du et al., "The spike protein of SARS-CoV—a target for vaccine and therapeutic development," Microbiology, vol. 7, pp. 226-236 (Mar. 2009).
Engelmayer et al., "Vaccinia virus inhibits the maturation of human dendritic cells: a novel mechanism of immune evasion", J Immunol., 163, pp. 6762-6768 (1999).
Espenschied J et al, "CTL-4 blockade enhances the therapeutic effect of an attenuated poxvirus vaccine targeting p53 in in established murine tumor model", Journal of Immunology, vol. 170, Issue 6, pp. 3401-3407.
Final Office Action on U.S. Appl. No. 15/565,609 DTD Jul. 17, 2019.

(56) References Cited

OTHER PUBLICATIONS

Fishcer et al., "Modified vaccinia virus Ankara protein F1L is a novel BH3-domain-binding protein and acts together with the early viral protein E3L to block virus-associated apoptosis" Cell Death Differ., 13, pp. 109-118 (2006).
Fuertes et al., "Host type I Ifn signals are required for antitumor CD8 T-cell responses through CD8{alpha} dendritic cells", J. Exp. Med., vol. 208, No. 10, 2005-2016 (2011).
Fuertes et al., "Type I interferon response and innate immune sensing of cancer," Trends Immunol., vol. 34, No. 2, pp. 67-73 (Feb. 2013).
Fung et al., "Human Coronavirus: Host-Pathogen Interaction," Annual Review of Microbiology, 73, pp. 529-557 (Jun. 21, 2019).
Gao et al., "Structure-function analysis of STING activation by c[G(2',5')pA(3',5')p] and targeting by antiviral DMXAA", Cell, 154, pp. 748-762 (2013).
Garcia et al., "Safety and immunogenicity of a modified pox vector-based HIV/AIDS vaccine candidate expressing Env, Gag, Pol and Nef proteins of HIV-1 subtype B (MVA-B) in healthy HIV-1-uninfected volunteers: A phase I clinical trial (RISVAC02)", Vaccine, 29, pp. 8309-8316 (2011).
Garrido et al., "The escape of cancer from T lymphocytes: immunoselection of MHC class I loss variants harboring structural-irreversible "hard" lesions," Cancer Immunol. Immunother., 59, pp. 1601-1606 (2010).
GenBank: U94848.1 "Vaccinia virus strain Ankara, complete genomic sequence" p. 1-3 (Apr. 13, 2003).
Gerlini et al., "Metastatic melanoma secreted IL-10 down-regulates CD1 molecules on dendritic cells in metastatic tumor lesions", Am J Pathol., 165, pp. 1853-1863 (2004).
Gitlin et al., "Essential role of mda-5 in type I IFN responses to polyriboinosinic: polyribocytidylic acid and encephalomyocarditis picornavirus", Proc. Natl. Acad. Sci. U S A., vol. 103, No. 22, pp. 8459-8464 (May 30, 2006).
Goepfert et al., "Phase 1 safety and immunogenicity testing of DNA and recombinant modified vaccinia Ankara vaccines expressing HIV-1 virus-like particles", J Infect Dis., 203, pp. 610-619 (2011).
Gomez et al., "MVA and NYVAC as vaccines against emergent infectious diseases and cancer," Current Gene Therapy, vol. 11, No. 3, p. 189-217 (6/11).
Gomez et al., "The poxvirus vectors MVA and NYVAC as gene delivery systems for vaccination against infectious diseases and cancer", Curr Gene Ther., 8, pp. 97-120 (2008).
Greiner et al. "The highly attenuated vaccinia virus strain modified virus Ankara induces apoptosis in melanoma cells and allows bystander dendritic cells to generate a potent anti tumoral immunity" Clinical and Experimental Immunology vol. 146. No. 2, Nov. 1, 2006 pp. 344-353.
Guerra et al., "Distinct gene expression profiling after infection of immature human monocyte- derived dendritic cells by the attenuated poxvirus vectors MVA and NYVAC," J. of Virology, vol. 61, No. 16, pp. 8701-8721 (May 30, 2007).
Guerra et al., "Host-Range Restriction in Vaccinia Virus E3L Deletion Mutant Can Be Overcome In Vitro, but Not In Vivo, by Expression of the Influenza Virus NS1 Protein," PLoS ONE. vol. 6 No. 12, p. e28677 (2011).
Haagmans, et al., "An orthopoxvirus-based vaccine reduces virus excretion after MERS-CoV infection in dromedary camels," Science, vol. 351, pp. 77-81 (Jan. 1, 2016).
Hamid et al., "Safety and Tumor Responses with Lambrolizumab (Anti-PD-1) in Melanoma", The New England journal of medicine, vol. 369, No. 2, pp. 134-144 (2013).
Hammerich et al., In situ vaccination for the treatment of cancer, Immunotherapy vol. 8, No. 3, Mar. 1, 2016, pp. 315-330.
Harrop et al., "Vaccination of Colorectal Cancer Patients with Modified Vaccinia Ankara Delivering the Tumor Antigen 5T4 (TroVax) Induces Immune Responses which Correlate with Disease Control: A Phase I/II Trial," Clinical Cancer Research, vol. 12, No. 11 Pt. 1, p. 3416-6424 (Jun. 1, 2006).
Hodge et al., "Modified Vaccinia Virus Ankara Recombinants Are as Potent as Vaccinia Recombinants in Diversified Prime and Boost Vaccine Regimens to Elicit Therapeutic Antitumor Responses," American Association for Cancer Research, vol. 63, No. 22, p. 7942-7949 (Nov. 15, 2003).
Hodi et al., "Improved survival with ipilimumab in patients with metastatic melanoma", The New England journal of medicine, 363, pp. 711-723 (2010).
Holshue et al., "First Case of 2019 Novel Coronavirus in the United States," New England Journal of Medicine, 9 pages (Jan. 31, 2020).
Hornemann et al., "Replication of Modified Vaccinia Virus Ankara in Primary Chicken Embryo Fibroblasts Requires Expression of the Interferon Resistance Gene E3L," Journal of Virology, vol. 77, No. 15, p. 8394-8407 (8/03).
Huber et al., "Regulation of effector and memory T-cell functions by type I interferon", Immunology, 132, pp. 466-474 (2011).
Inman, "Immunotherapy/Targeted Therapy Combinations Show Promise in BRAF-Mutated Melanoma," Targeted Oncology, retrieved from: https://www.targetedonc.com/conference/smr-esmo-melanoma/immunotherapytargeted-therapy-combinations-show-promise-in-brafmutated-melanoma (Oct. 20, 2017).
International Preliminary Report on Patentability on PCT/US2017/019549 dated Sep. 7, 2018 (13 pages).
International Search Report and Written Opinion on PCT/US2016/028184, dated Sep. 9, 2016, 17 pages.
International Search Report and Written Opinion on PCT/US2017/019548, dated Aug. 8, 2017, 17 pages.
International Search Report and Written Opinion on PCT/US2017/019549, dated Aug. 14, 2017 (17 pages).
International Search Report and Written Opinion on PCT/US2018/032451, dated Aug. 23, 2018, 16 pages.
International Search Report and Written Opinion on PCT/US2018/059476, dated Feb. 14, 2019, 9 pages.
International Search Report and Written Opinion, PCT/US2019/021853, Memorial Sloan Kettering Cancer Center (Jul. 16, 2019).
International Search Report and Written Opinion, PCT/US2019/051343 (Feb. 7, 2020).
Ishikawa et al., "STING is an endoplasmic reticulum adaptor that facilitates innate immune signaling", Nature, 455, pp. 674-678 (2008).
Jacobs et al., Vaccinia virus vaccines: Past, present and future, Antiviral Research, Elsevier BV, NL vol. 84, No. 1, Oct. 1, 2009 pp. 1-13.
Jenne et al., "Poxvirus as a vector to transduce human dendritic cells for immunotherapy: abortive infection but reduced APC function", Gene therapy, 7, pp. 1575-1583 (2000).
Jochems et al., "Tumor-infiltrating immune cells and prognosis: the potential link between conventional cancer therapy and immunity", Exp Biol Med. (Maywood), 236, pp. 567-579 (2011).
Kibler et al., "Double-stranded RNA is a trigger for apoptosis in vaccinia virus-infected cells", J. Virol., vol. 71, No. 3, pp. 1992-2003 (1997).
Kirkwood et al., "High-Dose Interferon Alfa-2b Significantly Prolongs Relapse-Free and Overall Survival Compared With the GM2-KLH/QS-21 Vaccine in Patients With Resected Stage IIB-III Melanoma: Results of Intergroup Trial E1694/S9512/C509801." Journal of Clinical Oncology 19:2370-2380, 2001, American Society of Clinical Oncology.
Kirn et al., "Replication-selective virotherapy for cancer: Biological principles, risk management and future directions," Nat. Med., 7, pp. 781-787 (2001).
Kirn et al., "Targeted and armed oncolytic poxviruses: a novel multi-mechanistic therapeutic class for cancer," Nature Reviews—Cancer, 9, pp. 64-71 (2009).
Kirn et al., "Targeting of interferon-beta to produce a specific, multi-mechanistic oncolytic vaccinia virus", PLoS Med., vol. 4, No. 12, pp. 2001-2012 (2007).
Kreiter et al., "Mutant MHC class II epitopes drive therapeutic immune responses to cancer." Nature. Apr. 22, 2015, vol. 520, No. 7549, pp. 692-696.
Kuzu et al., "Current State of Animal (Mouse) Modeling in Melanoma Research," Cancer Growth and Metastasis, 8(S1):81-94 (2015).

(56) References Cited

OTHER PUBLICATIONS

Lacy et al., "Immunotherapy for Melanoma," Expert Rev. Dermatol., 7, pp. 51-68 (2012).
Langland et al., "Inhibition of PKR by vaccinia virus: role of the N- and C-terminal domains of E3L," Journal of Virology, vol. 324, No. 2, p. 419-429 (Jul. 1, 04).
Leach et al., "Enhancement of antitumor immunity by CTLA-4 blockade," Science, 271, pp. 1734-1736 (1996).
Lee et al., "The interferon-induced double-stranded RNA-activated protein kinase induces apoptosis," Journal of Virology, vol. 199, No. 2, p. 491-496 (3/94).
Lee et al., "Effect of resveratrol on the metastasis of 4T1 mouse breast cancer cells in vitro and in vivo," Nutrition Res. and Practice, vol. 6, No. 4, pp. 294-300 (2012).
Li et al., "Angiotensin-converting enzyme 2 is a functional receptor for the SARS coronavirus," Nature, vol. 426, pp. 450-454 (Nov. 27, 2003).
Li et al., "Disruption of MHC class II-restricted antigen presentation by vaccinia virus," J. Immunol., 175, pp. 6481-6488 (2005).
Li et al., "Early Transmission Dynamics in Wuhan, China, of Novel Coronavirus—Infected Pneumonia," New England Journal of Medicine, 9 pages (Jan. 29, 2020).
Li et al., "Pivotal roles of cGAS-cGAMP signaling in antiviral defense and immune adjuvant effects", Science, 341, pp. 1390-1394 (2013).
Li et al., "Structure of SARS Coronavirus Spike Receptor-Binding Domain Complexed with Receptor," Science, vol. 309, pp. 1864-1868 (Sep. 16, 2005).
Liu et al., "Deletion of C7L and K1L genes leads to significantly decreased virulence of recombinant vaccinia cirus TianTian," PLoS One, vol. 8, No. 7:e68115, pp. 1-13 (Jul. 1, 2013).
Liu, "Cancer-killing virus plus PD-1 and MEK inhibitors make for a 3-pronged attack on melanoma," retrieved from: https://www.fiercebiotech.com/research/pd-1-mek-inhibitor-and-anti-cancer-virus-a-3-pronged-attack-melanoma, 2 pages (Dec. 12, 2018).
Ludwig et al., "Role of Viral Factor E3L in Modified Vaccinia Virus Ankara Infection of Human HeLa Cells: Regulation of the Virus Life Cycle and Identification of Differentially Expressed Host Genes," Journal of Virology, vol. 79, No. 4, p. 2584-2596 (2/05).
Mandl, SJ et al., Immunotherapy With MVA-BN-HER2 Induces HER-2-specific Th1 Immunity and Alters The Intratumoral Balance of Effector and Regulatory T cells. Cancer Immunol Immunother, 2012, vol. 61, pp. 19-29.
Mayr et al., English-language translation of Abstract of: "[The smallpox vaccination strain MVA: marker, genetic structure, experience gained with the parenteral vaccination and behavior in organisms with a debilitated defence mechanism (author's transl)]," Zentralbl Bakteriol, Orig. B, 167, pp. 375-390 (1978).
Mayr et al., English-language translation of Abstract of: "Passage history, properties, and applicability of the attenuated vaccinia virus strain MVA," Infection, 3, pp. 6-14 (1975).
McCart et al., "Systemic Cancer Therapy with a Tumor-selective Vaccinia Virus Mutant Lacking Thymidine Kinase and Vaccinia Growth Factor Genes.", Cancer Res., (2001), 61, [24], p. 8751-8757.
McIntyre et al., "Mouse models of colorectal cancer as preclinical models," Bioessays, 37(8), pp. 909-920 (Aug. 2015).
Medrano et al., "Immunomodulatory and antitumor effects of type I interferons and their application in cancer therapy." Oncotarget, 2017, vol. 8, (No. 41), pp. 71249-71284.
Melief CJ. Cancer immunotherapy by dendritic cells. Immunity. Sep. 19, 2008;29(3):372-83. doi: 10.1016/j.immuni.2008.08.004. PMID: 18799145 (Year: 2008).
Mellman et al., "Cancer immunotherapy comes of age", Nature, 480, pp. 480-489 (2011).
Meng et al., "C7L Family of Poxvirus Host Range Genes Inhibits Antiviral Activities Induced by Type I Interferons and Interferon Regulatory Factor 1", J. Virol., vol. 86, No. 8, pp. 538-4547 (2012).
Meng et al., "Vaccinia Virus K1L and C7L Inhibit Antiviral Activities Induced by Type I Interferons," Journal of Virology, vol. 83, No. 20, p. 10627-10636 (10/09).
Meyer et al., "Mapping of deletions in the genome of the highly attenuated vaccinia virus MVA and their influence on virulence", J. Gen. Virol., 72 ( Pt 5), pp. 1031-1038 (1991).
Mlecnik et al., "Tumor immunosurveillance in human cancers", Cancer Metastasis Rev, 30, pp. 5-12 (2011).
Morales et al., Genome comparison of a nonpathogenic myoxma virus field strain with its ancestor, the virulent Lausanne strain, J. Virol, vol. 83, No. 5, pp. 2397-2403 Mar. 2009.
Moss, "Poxviridae: The viruses and their replication," In Fields Virology (Lippincott Williams & Wilkins), pp. 2905-2946 (2007).
Nagaria et al., "Combined targeting of RAF and MEK synergistically inhibits tumorigenesis in triple negative breast cancer model systems," Oncotarget, vol. 8, No. 46, pp. 80804-80819 (Aug. 24, 2017).
Nagorsen et al., "Transcriptional analysis of tumor-specific T-cell responses in cancer patients," Crit. Rev. Immunol., 22, pp. 449-462 (2002).
Nakayama et al., "In vitro comparison between mouse B16 and human melanoma cell lines of the expression of ICAM-1 induced by cytokines and/or hyperthermia," J. Dermatol., 24(6), pp. 351-360 (Jun. 1997).
Nemunaitis, J., "Oncolytic viruses,". Invest. New Drugs, 17, pp. 375-386 (1999).
Notice of Allowance on U.S. Appl. No. 15/565,609 DTD Oct. 31, 2019.
Notice of Allowance on U.S. Appl. No. 15/565,609 DTD Nov. 8, 2019.
Notice of Allowance on U.S. Appl. No. 16/741,634 DTD Oct. 18, 2021.
Oble et al., "Focus on TILs: prognostic significance of tumor infiltrating lymphocytes in human melanoma", Cancer immunity, 9, pp. 1-20 (2009).
Pardoll, "The blockade of immune checkpoints in cancer immunotherapy," Nat. Rev. Cancer, 12(4), pp. 252-264 (Mar. 22, 2012).
Park et al., "Use of a targeted oncolytic poxvirus, JX-594, in patients with refractory primary or metastatic liver cancer: a phase I trial," Lancet Oncol., 9, pp. 533-542 (May 19, 2008).
Peggs et al., "Blockade of CTLA-4 on both effector and regulatory T-cell compartments contributes to the antitumor activity of anti-CTLA-4 antibodies", J Exp Med., 206, pp. 1717-1725 (2009).
Peihong et al., "Modified Vaccinia Virus Ankara Triggers Type I Ifn Production in Murine Conventional Dendritic Cells via a cGAS/STING-Mediated Cytosolic DNA-Sensing Pathway," PLOS Pathogens, vol. 10, No. 4, pg e1003989 (Apr. 17, 2014).
Peihong, "P339 Intratumoral delivery of modified vaccinia virus Ankara expressing human Flt3L as cancer immunotherapy," 31st Annual Meeting and Associated Programs of the Society for Immunotherapy of Cancer, Pt. 2, p. 1-241 (2016).
Peiris, et al., "The Severe Acute Respiratory Syndrome," New England Journal of Medicine, vol. 349, pp. 2431-2441 (Dec. 18, 2003).
Perkus et al., "Vaccinia virus host genes," Virology, 179(1), pp. 276-286 (1990).
Pramanick et al., "Excipient selection in parenteral formulation development", Pharma Times, vol. 45, No. 3, pp. 65-77 (2013).
Raj et al., "Dipeptidyl peptidase 4 is a functional receptor for the emerging human coronavirus—EMC," Nature, vol. 495, 6 pages (Mar. 13, 2013).
Reddy et al., "Influences of BRAF Inhibitors on the Immune Microenvironment and the Rationale for Combined Molecular and Immune Targeted Therapy," Curr. Oncol. Rep., 18(7)15 pages (Jul. 2016).
Rice et al. An H PV-E6/E7 immunotherapy plus PD-1 checkpoint inhibition results in tumor regression and reduction in PD-L 1 expression. Cancer Gene Therapy (2015) 22, 454-462.
Robert et al., "Ipilimumab plus dacarbazine for previously untreated metastatic melanoma", The New England journal of medicine, 364, pp. 2517-2526 (2011).

(56) References Cited

OTHER PUBLICATIONS

Sabbatino et al., "Antitumor activity of BRAF inhibitor and IFN combination in BRAF-mutant melanoma," J. Natl. Cancer Inst., 108(7), 11 pages (Feb. 5, 2016).
Sato et al., "Distinct and essential roles of transcription factors IRF-3 and IRF-7 in response to viruses for IFN-alpha/beta gene induction", Immunity, 13, pp. 539-548 (2000).
Sauer et al., "The N-ethyl-N-nitrosourea-induced Goldenticket mouse mutant reveals an essential function of Sting in the in vivo interferon response to Listeria monocytogenes and cyclic dinucleotides", Infection and immunity, vol. 79, No. 2, pp. 688-694 (2011).
Schaedler et al., "Sequential administration of a MVA-based MUC1 cancer vaccine and the TLR9 ligand Litenimod (Li28) improves local immune defense against tumors," Vaccine, vol. 35, No. 4, p. 577-585 (Jan. 23, 17).
Schumacher et al., "Neoantigens in cancer immunotherapy", Science, 348, pp. 69-74 (2015).
Sharma et al., "The future of immune checkpoint therapy", Science, 348, pp. 56-61 (2015).
Sivan et al., "Identification of Restriction Factors by Human Genome-Wide RNA Interference Screening of Viral Host Range Mutants Exemplified by Discovery of SAMD9 and WDR6 as Inhibitors of the Vaccinia Virus K1L- C7L- Mutant", mBio, vol. 6, No. 4, pp. 1-9 (2015).
Song, et al., "Middle East Respiratory Syndrome Coronavirus Spike Protein Delivered by Modified Vaccinia Virus Ankara Efficiently Induces Virus-Neutralizing Antibodies," Journal of Virology, vol. 87, pp. 11950-11954 (Nov. 2013).
Sun et al., "Cyclic GMP-AMP synthase is a cytosolic DNA sensor that activates the type I interferon pathway", Science, 339, pp. 786-791 (2013).
Sutter et al., "Vaccinia vectors as candidate vaccines: the development of modified vaccinia virus Ankara for antigen delivery," Current Drug Targets—Infectious Disorders 3, pp. 263-271 (2003).
Tagliamonte et al., "Antigen-specific vaccines for cancer treatment", Human vaccines & immunotherapeutics, 10, pp. 3332-3346 (2014).
Takaoka et al., "New aspects of IFN-alpha/beta signalling in immunity, oncogenesis and bone metabolism", Cancer Sci., vol. 94, No. 5, pp. 405-411 (2003).
Thorne et al., "Rational strain selection and engineering creates a broad-spectrum, systemically effective oncolytic poxvirus, JX-963", J Clin Invest., vol. 117, No. 11, pp. 3350-3358 (2007).
Topalian et al., "Immune checkpoint blockade: a common denominator approach to cancer therapy", Cancer Cell, vol. 27, No. 4, pp. 450-461 (2015).
Topalian et al., "Targeting the PD-1/B7-H1(PD-L1) pathway to activate anti-tumor immunity", Curr Opin Immunol., 24, pp. 207-212 (2012).
Tormo et al., "Targeted activation of innate immunity for therapeutic induction of autophagy and apoptosis in melanoma cells", Cancer Cell, vol. 16, No. 2, pp. 103-114 (2009).
Tumeh et al., "PD-1 blockade induces responses by inhibiting adaptive immune resistance", Nature, vol. 515, No. 7258, pp. 568-571 (2014).
US Office Action on U.S. Appl. No. 16/741,634 DTD Jun. 29, 2021.
Ventura et al Abstracts/Adaptive Immunity and Vaccination, Journal of Investigative Dermatology 2016 vol. 136 p. S6.
Verardi et al., "A vaccinia virus renaissance: new vaccine and immunotherapeutic uses after smallpox eradication," Human vaccines & immunotherapeutics, 8, pp. 961-970 (2012).
Verheust et al., "Biosafety aspects of modified vaccinia virus Ankara (MVA)-based vectors used for gene therapy or vaccination," Vaccine, 30, pp. 2623-2632 (2012).
Vijaysri et al., "Vaccinia Viruses with Mutations in the E3L Gene as Potential Replication- Competent, Attenuated Vaccines: Intra-Nasal Vaccination," Vaccine, vol. 26, No. 5, p. 664-676 (Jan. 30, 2008).

Volz, et al., "Protective Efficacy of Recombinant Modified Vaccinia Virus Ankara Delivering Middle East Respiratory Syndrome Coronavirus Spike Glycoprotein," Journal of Virology, vol. 89, pp. 8651-8656 (Aug. 2015).
Waibler et al., "Modified Vaccinia Virus Ankara Induces Toll-Like Receptor-Independent Type I Interferon Responses," Journal of Virology, vol. 81, No. 22, p. 12101-12110 (11/07).
Wang et al., "034 recombinant replication competent attenuated vaccinia virus expressing human Flt3L for cancer immunotherapy," J. Invest. Derm., vol. 136, No. 5, pg. S6 (May 2016).
Wang et al., Abstracts-Adaptive Immunity and Vaccination 034, Recombinant replication competent attenuated vaccinia virus expressing human Flt3L for cancer immunotherapy, Journal of Investigative Dermatology vol. 136, No. 5 May 2016 p. S6.
Weaver et al., "The identification and characterization of a monoclonal antibody to the vaccinia virus E3 protein", Virus Res., 130, pp. 269-274 (2007).
Wing et al., "CTLA-4 control over Foxp3 regulatory T-cell function", Science, 322, pp. 271-275 (2008).
Wolchok et al., "Ipilimumab monotherapy in patients with pretreated advanced melanoma: a randomised, double-blind, multicentre, phase 2, dose-ranging study," Lancet Oncol., 11, pp. 155-164 (2010).
Wolchok et al., "Nivolumab plus ipilimumab in advanced melanoma", The New England journal of medicine, 369, pp. 122-133 (2013).
Woo et al., "STING-dependent cytosolic DNA sensing mediates innate immune recognition of immunogenic tumors", Immunity, vol. 41, No. 5, pp. 830-842 (2014).
Wu et al., "Cyclic GMP-AMP is an endogenous second messenger in innate immune signaling by cytosolic DNA", Science, 339, pp. 826-830 (2013).
Wyatt et al., "Enhanced cell surface expression, immunogenicity and genetic stability resulting from a spontaneous truncation of HIV Env expressed by a recombinant MVA", Virology, 372, pp. 260-272 (2008).
Yong, et al., "Recent Advances in the Vaccine Development Against Middle East Respiratory Syndrome-Coronavirus," Frontiers in Microbiology, vol. 10, 18 pages (Aug. 2, 2019).
Zaki, et al., "Isolation of a Novel Coronavirus from a Man with Pneumonia in Saudi Arabia," The New England Journal of Medicine, vol. 367, pp. 1814-1820 (Nov. 8, 2012).
Zamarin et al., "Localized oncolytic virotherapy overcomes systemic tumor resistance to immune checkpoint blockade immunotherapy", Science translational medicine, vol. 6, No. 226, pp. 1-12 (2014).
Zhang, et al., "A Dna vaccine induces SARS coronavirus neutralization and protective immunity in mice," Nature, vol. 428, pp. 561-564 (Apr. 2004).
Zhou, et al., "A pneumonia outbreak associated with a new coronavirus of probable bat origin," Nature, 23 pages (Feb. 3, 2020).
Zurkova et al., "The expression of the soluble isoform of hFlt3 ligand by recombinant vaccinia virus enhances immunogenicity of the vector," vol. 21, No. 5, p. 1335-1343 (Apr. 6, 2009).
Lee SY et al. Intratumoral injection of therapeutic H PV vaccinia vaccine following cisplatin enhances H PV-specific anti tumor effects. Cancer Immunol Immunother (2013) 62: 1175-1185 (Year: 2013).
Reuschenbach M et al. High-risk human papillomavirus in non-melanoma skin lesions from renal allograft recipients and immunocompetent patients. British Journal of Cancer 2011 104, 1334-1341 (Year: 2011).
Foy et al., "Poxvirus immunotherapies in combination with immune checkpoint inhibitors synergize to eliminate tumors in a mouse tumor model." Journal for ImmunoTherapy of Cancer 2013, 1(Suppl 1):P72.
Wong et al. Oncolytic Viruses for Cancer Therapy: Overcoming the Obstacles. Viruses, 2010, 2: 78-106.
Dai P et al. Abstract B031: Heat-inactivated modified vaccinia virus ankara induces type I IFN and antitumor immunity via the cytosolic DNA-sensing pathway. (Cancer Immunol Res (2016) 4 (1_Supplement): B031) (Year: 2016).

(56) References Cited

OTHER PUBLICATIONS

Diao et al., "Vaccine Application and Safety Q&A." China Pharmaceutical Science and Technology Press, pp. 35-36, Apr. 30, 2017.
Wang Wei al. Abstract A007: Intratumoral delivery of inactivated vaccinia virus is more efficacious than live oncolytic vaccinia virus in murine bilateral tumor implantation models. (Cancer Immunol Res (2016) 4 (11_Supplement): A007) (Year: 2016).
Goldufsky et al. "Oncolytic virus therapy for cancer." Oncolytic Virotherapy. Sep. 23, 2023, No. 2, pp. 31-46.
Nemeckova et al. "Experimental therapy of HPV16 induced tumors with IL12 expressed by recombinant vaccinia virus in mice." International Journal of Molecular Medicine. 2003, No. 12, pp. 789-796.
O'Sullivan et al. "Cancer immunoediting by the innate immune system in the absence of adaptive immunity." J. Exp. Med. Sep. 24, 2012, vol. 209, No. 10, pp. 1869-1882.
Sobhani et al. "Implications of photodynamic cancer therapy: an overview of PDT mechanisms basically and practically." J. Egypt Natl. Canc. Inst. Web. Nov. 15, 2021, pp. 1-13.
Vu et al. "Cancer Resistance to Immunotherapy: Molecular Mechanisms and Tackling Strategies." Int. J. Mol. Sci. Sep. 18, 2022, pp. 1-22.
Yang et al. "Vaccinia E5 is a major inhibitor of the DNA sensor cGAS." Nature Communications. May 22, 2023. 16 pages.
Kwissa et al., "Adjuvanting a DNA vaccine with a TLR9 ligand plus Flt3 ligand results in enhanced cellular immunity against the simian immunodeficiency virus." J. Exp. Medicine. Oct. 29, 2007, vol. 204, No. 11, pp. 2733-2746.
Fang J et al: "Stable antibody expression at therapeutic levels using the 2A peptide", Nature Biotechnology, Nature Publishing Group US, New York, vol. 23, No. 5, Apr. 17, 2005 (Apr. 17, 2005), pp. 584-590.
T Du et al: "Tumor-specific oncolytic adenoviruses expressing granulocyte macrophage colony-stimulating factor or anti-CTLA4 antibody for the treatment of cancers", Cancer Gene Therapy, vol. 21, No. 8, Jul. 18, 2014 (Jul. 18, 2014), pp. 340-348.
Wang Weiyi et al: "LB-306: Oncolytic vaccinia virus expressing immune checkpoint blockade antibody as cancer immunotherapeutics", Cancer Research; Annual Meeting of the American-Association-For-Cancer-Research (AACR), American Association for Cancer Research, US; Chicago, IL, USA, vol. 78, No. 13, Suppl . S, Jun. 30, 2018 (Jun. 30, 2018), pp. LB-306.
Wu, et al., "Structure and function of vaccinia virus E3L protein." Journal of Biology, No. 2, pp. 64-83, (Apr. 13, 2013).
Gerdes et al. Emerging understanding of multiscale tumor heterogeneity, Front. Oneal. Dec. 18, 2014 doi: 10.3389/fonc.2014.00366, pp. 1-12 (Year: 2014).
Gura, T., Systems for Identifying New Drugs Are Often Faulty, Science, 1997, 278:1041-1042 (Year: 1997).
Kaiser, J., First pass at cancer genome reveals complex landscape, Science, 2006, 313:1370 (Year: 2006).

\* cited by examiner

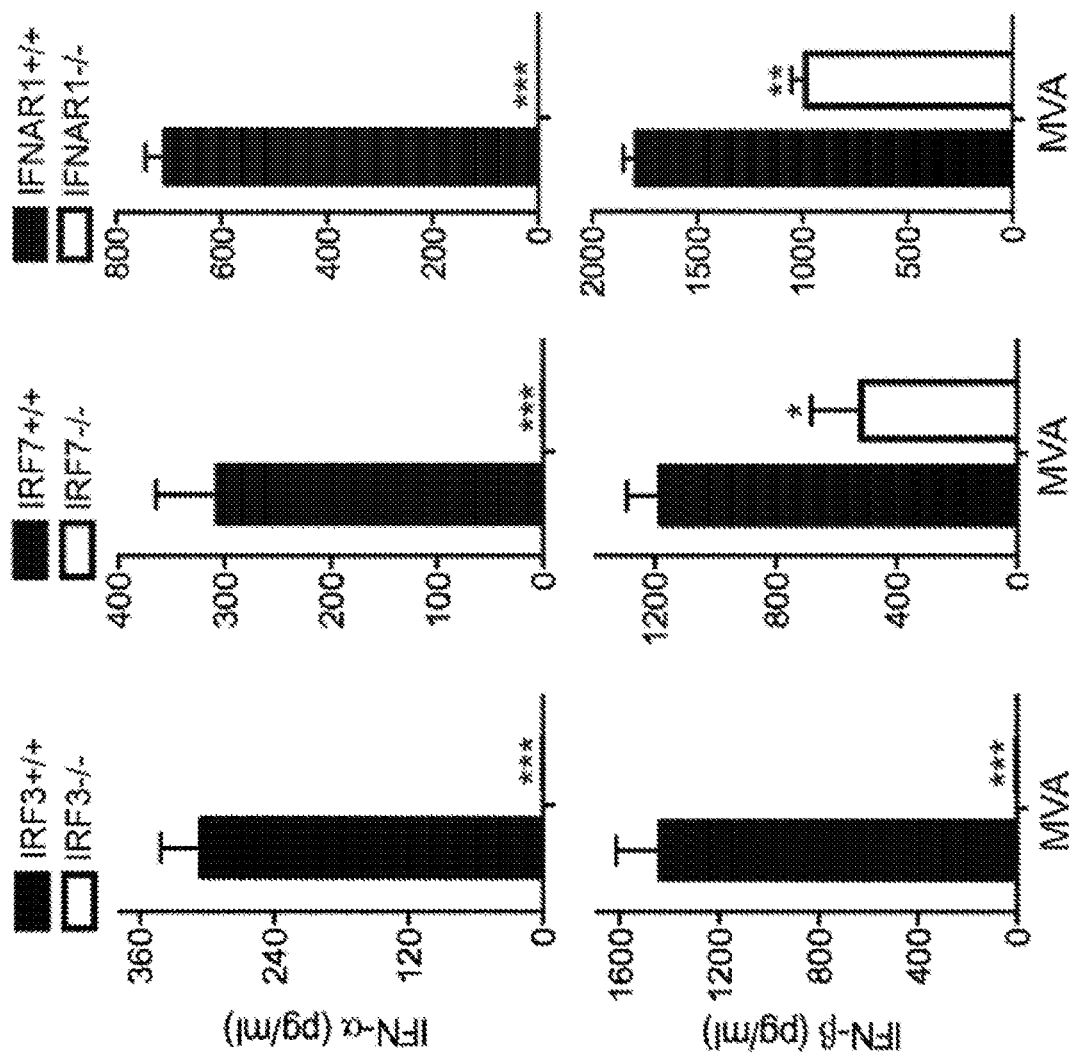

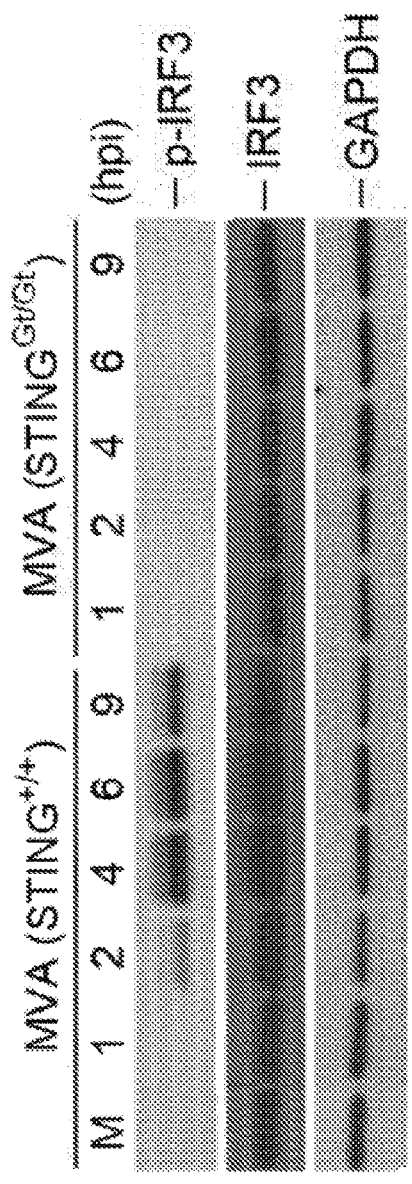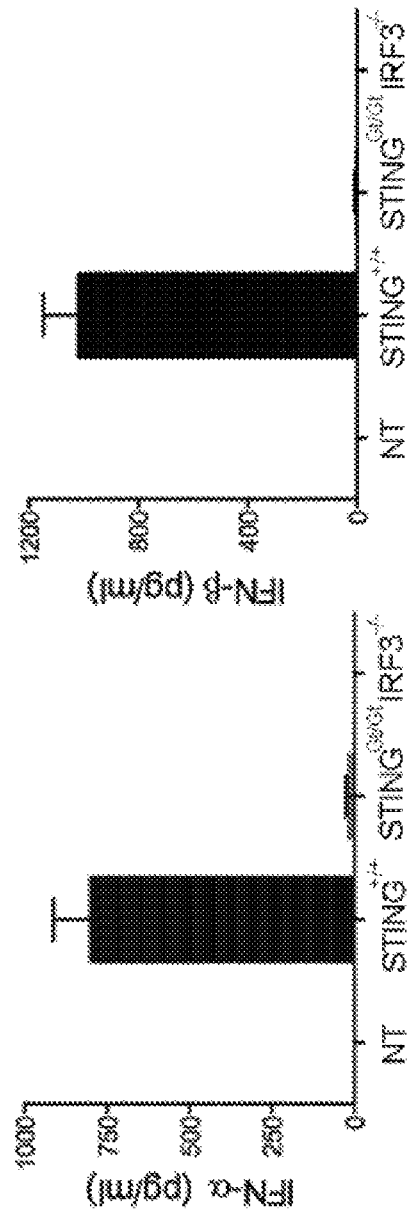
FIG. 3C
FIG. 3D

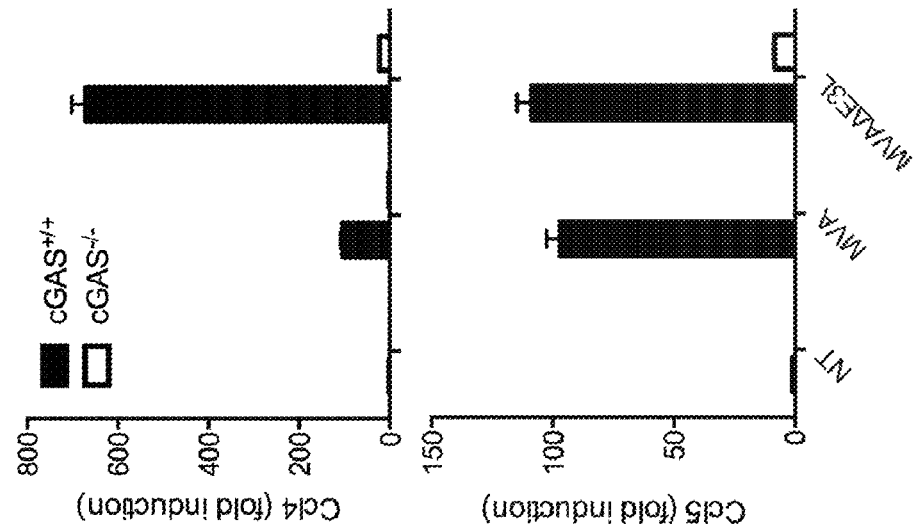
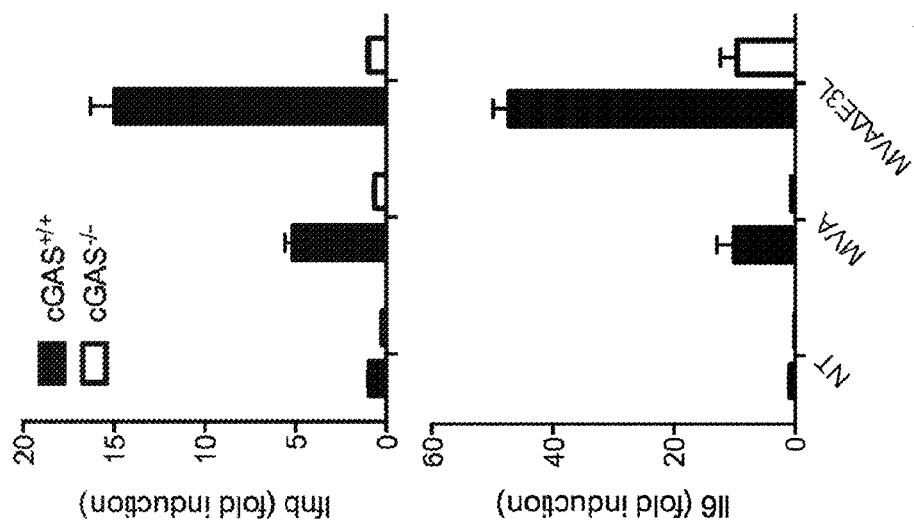

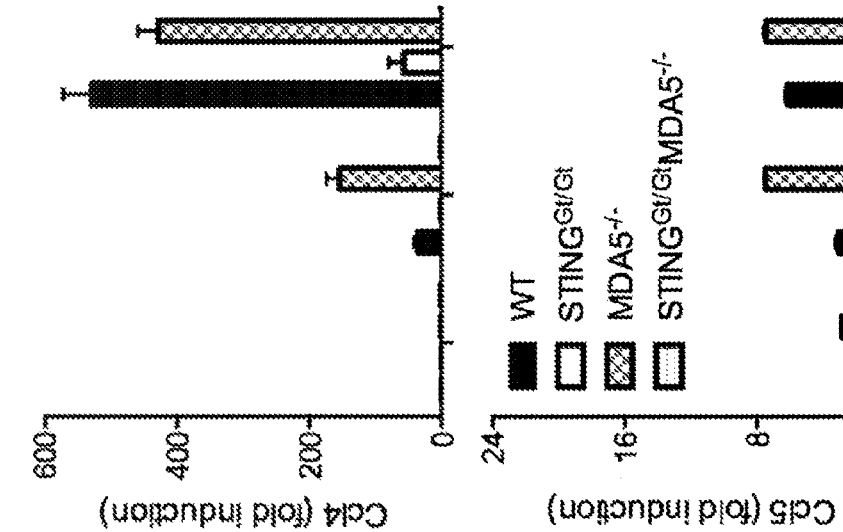
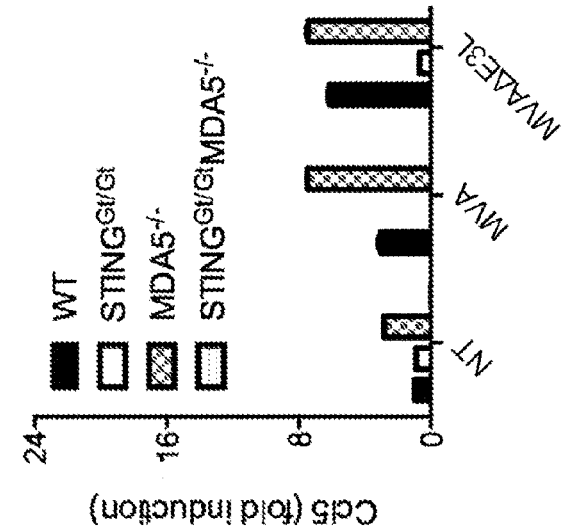
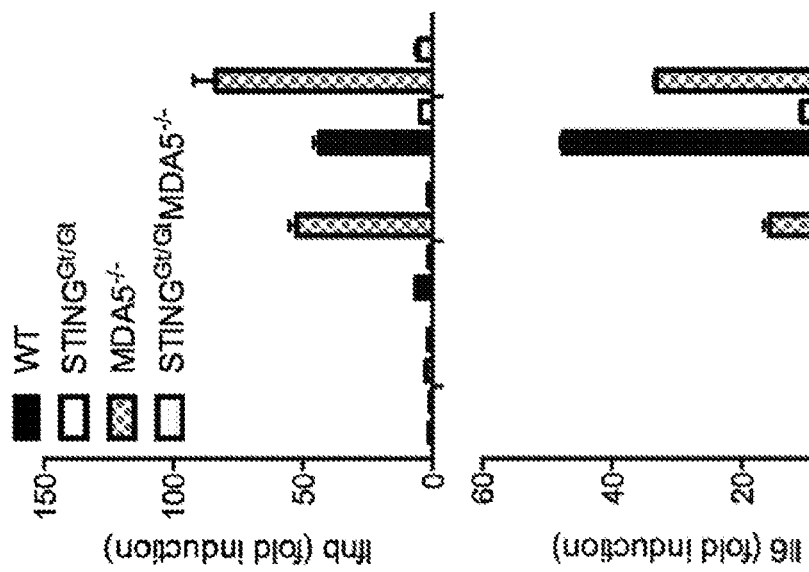
FIG. 8E
FIG. 8F
FIG. 8G
FIG. 8H

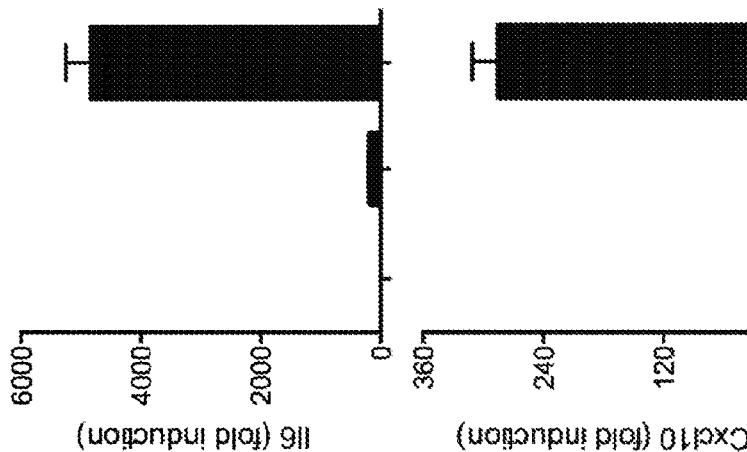
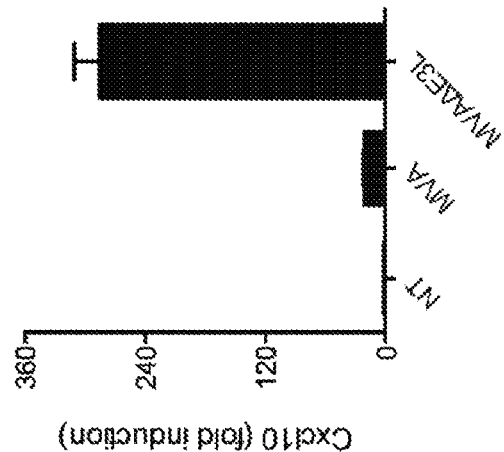
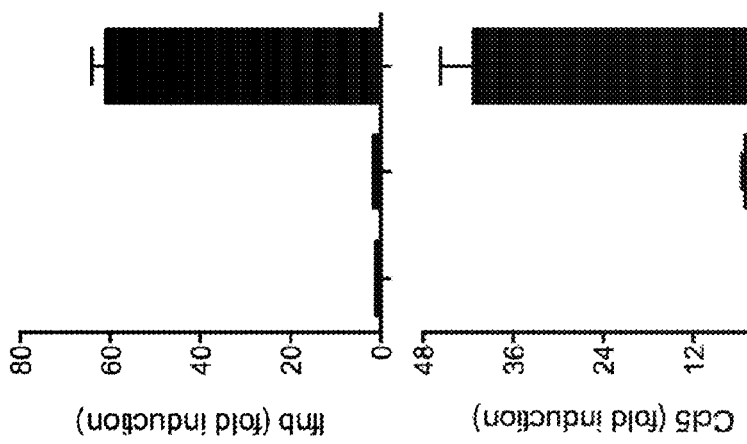
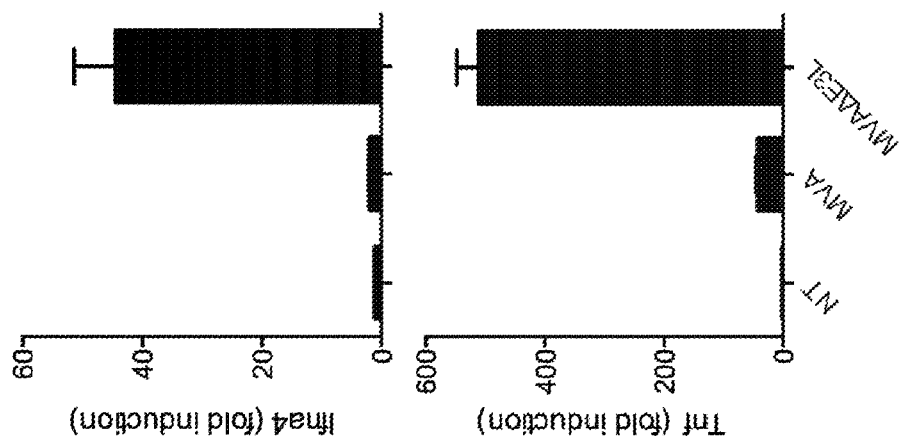

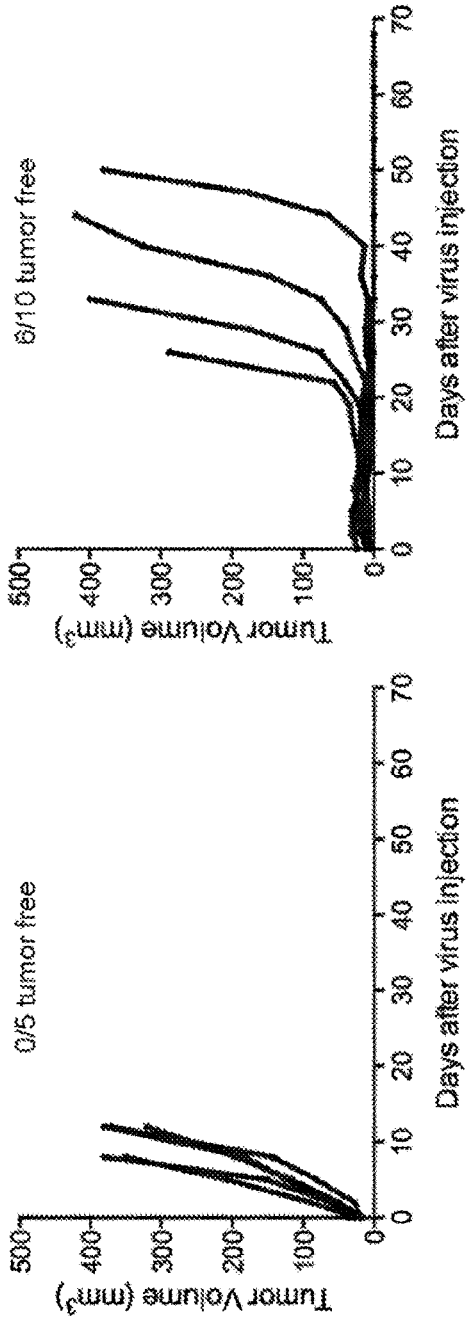
FIG. 12A
FIG. 12B
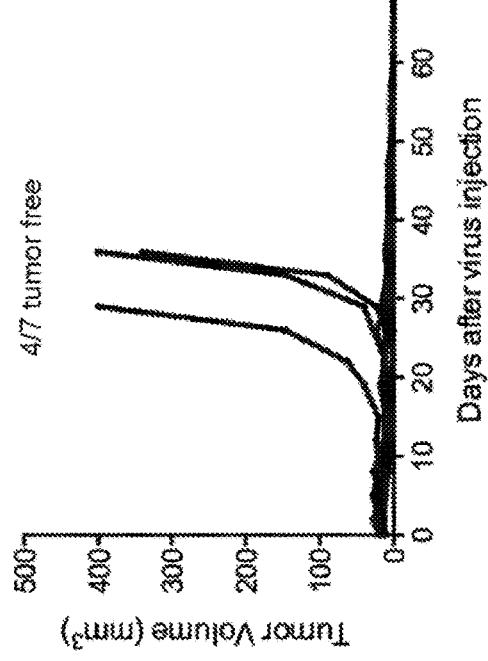
FIG. 12C

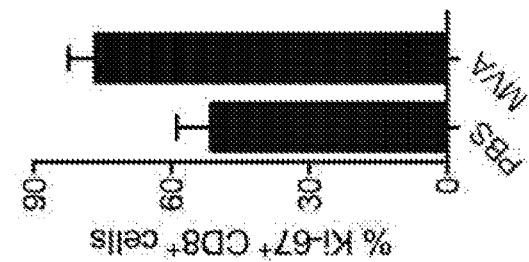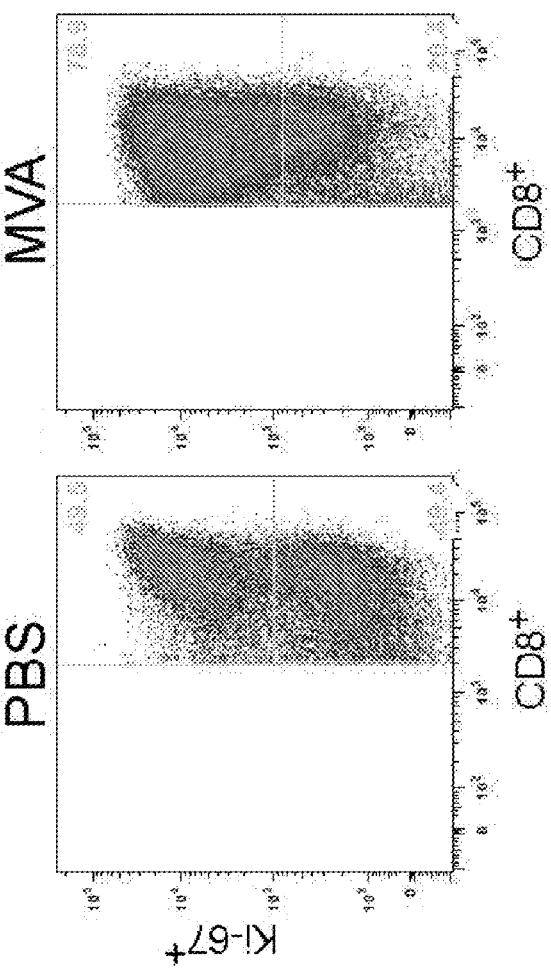

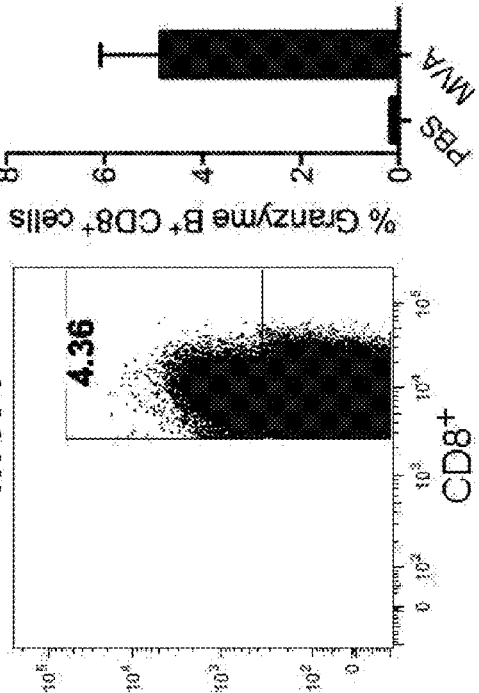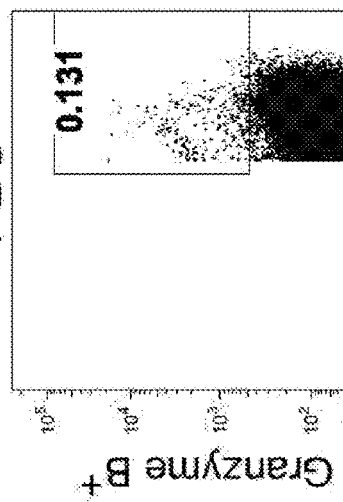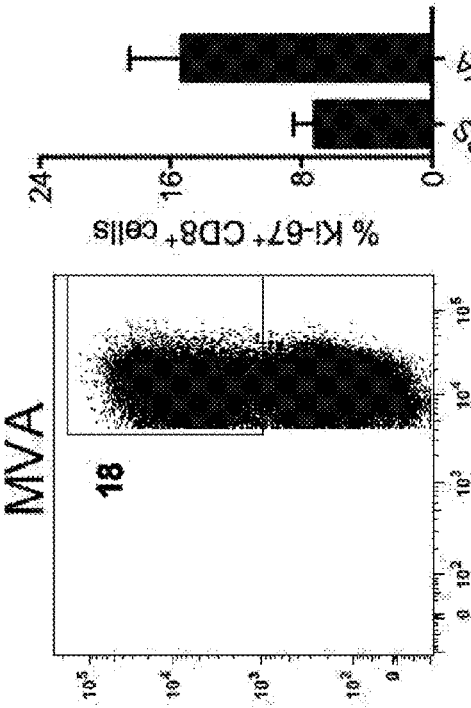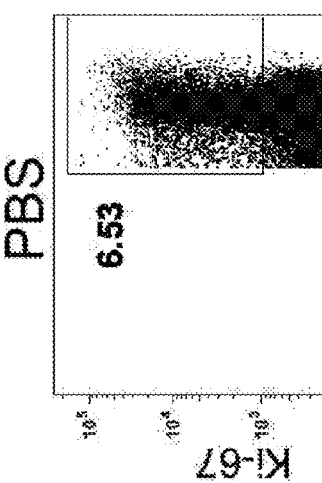

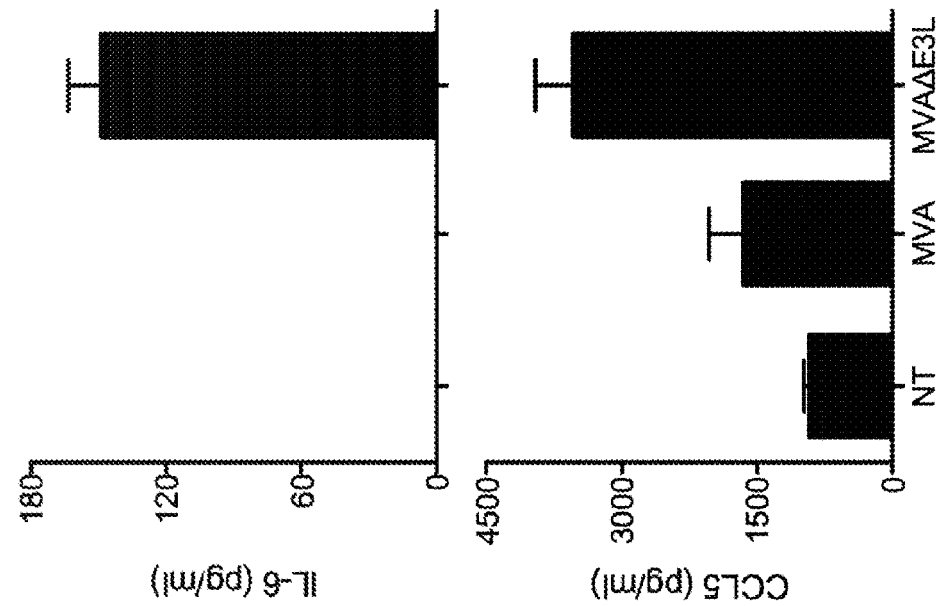
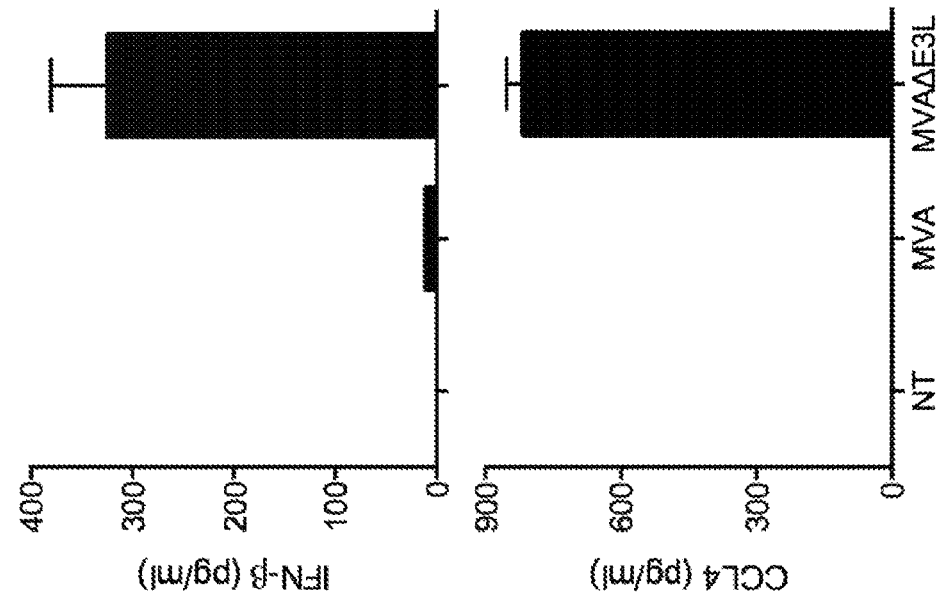
FIG. 15A
FIG. 15B
FIG. 15C
FIG. 15D

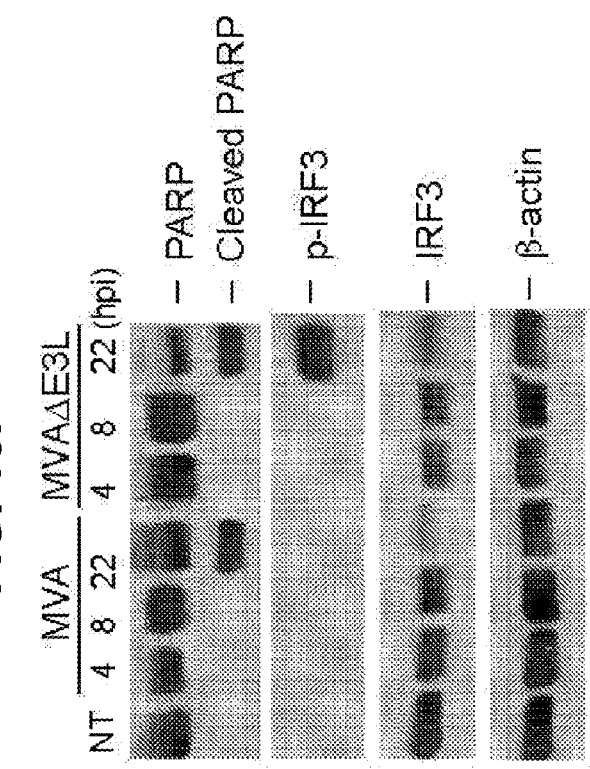
FIG. 15I
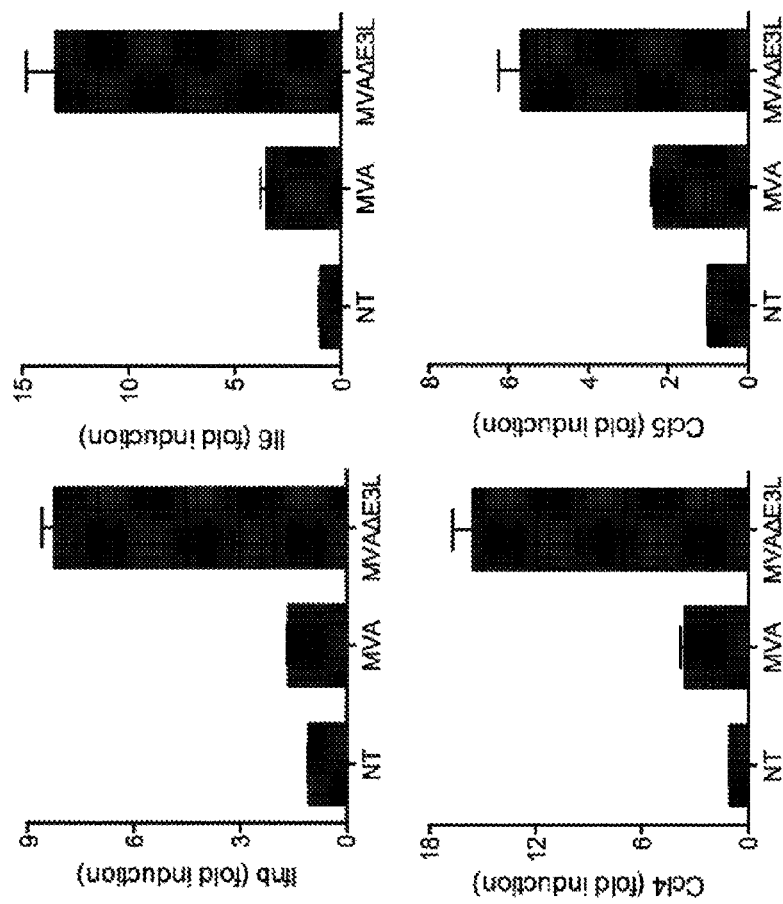
FIG. 15E
FIG. 15F
FIG. 15G
FIG. 15H

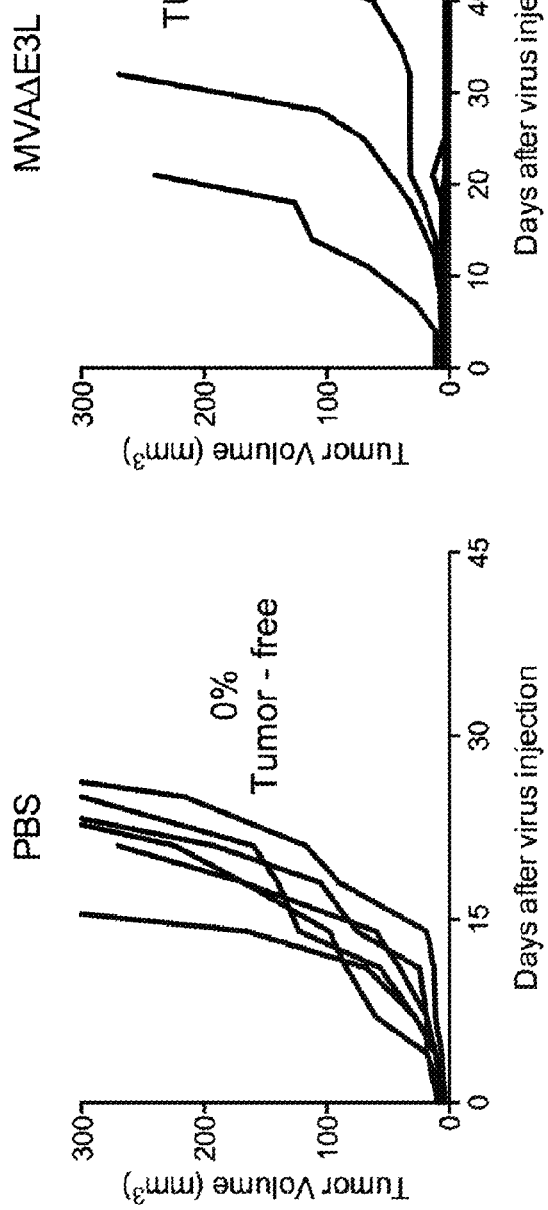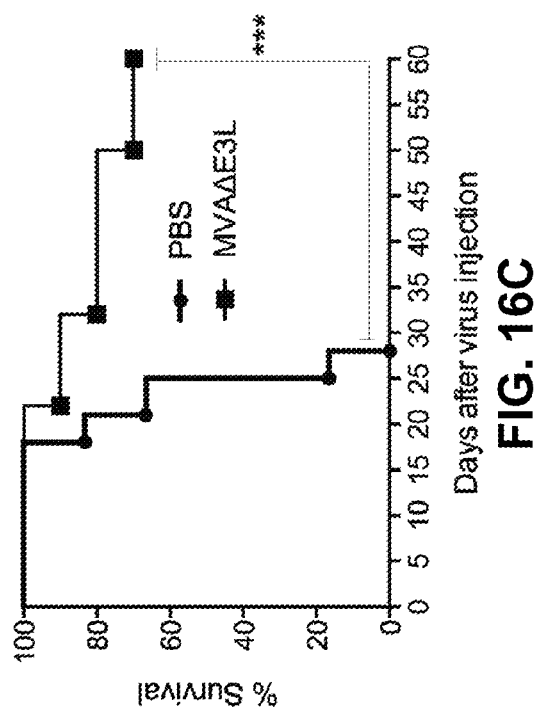

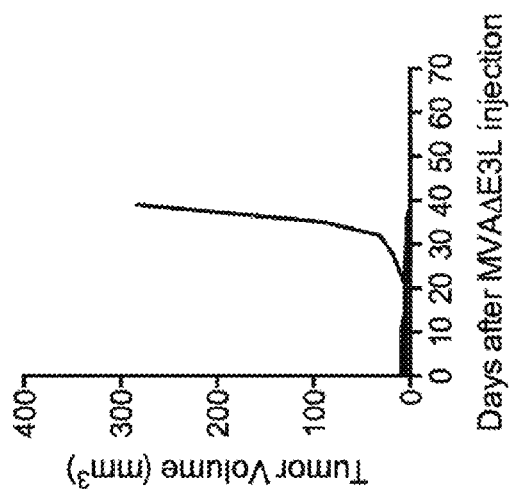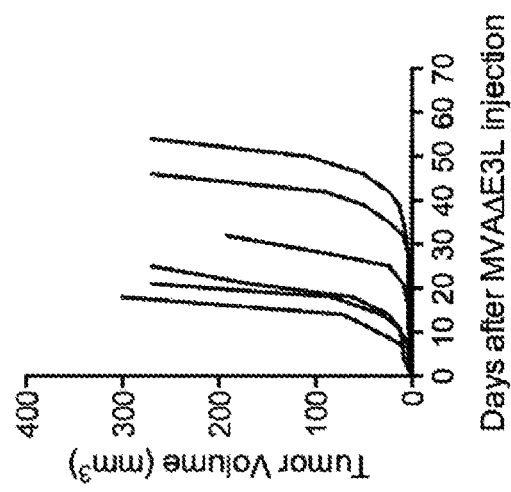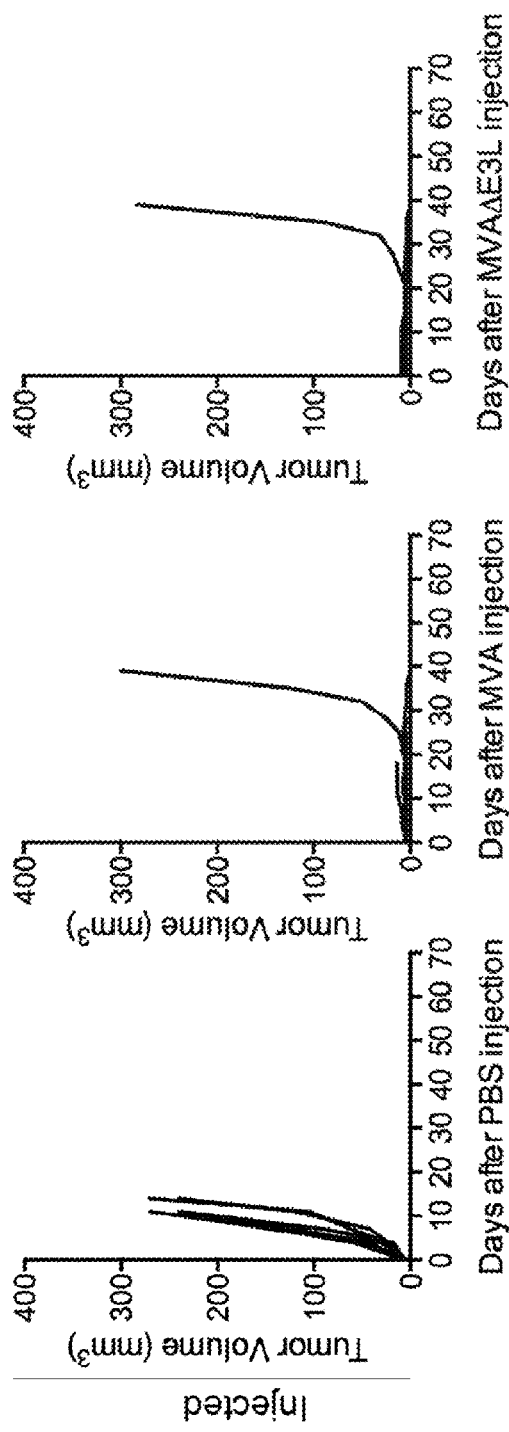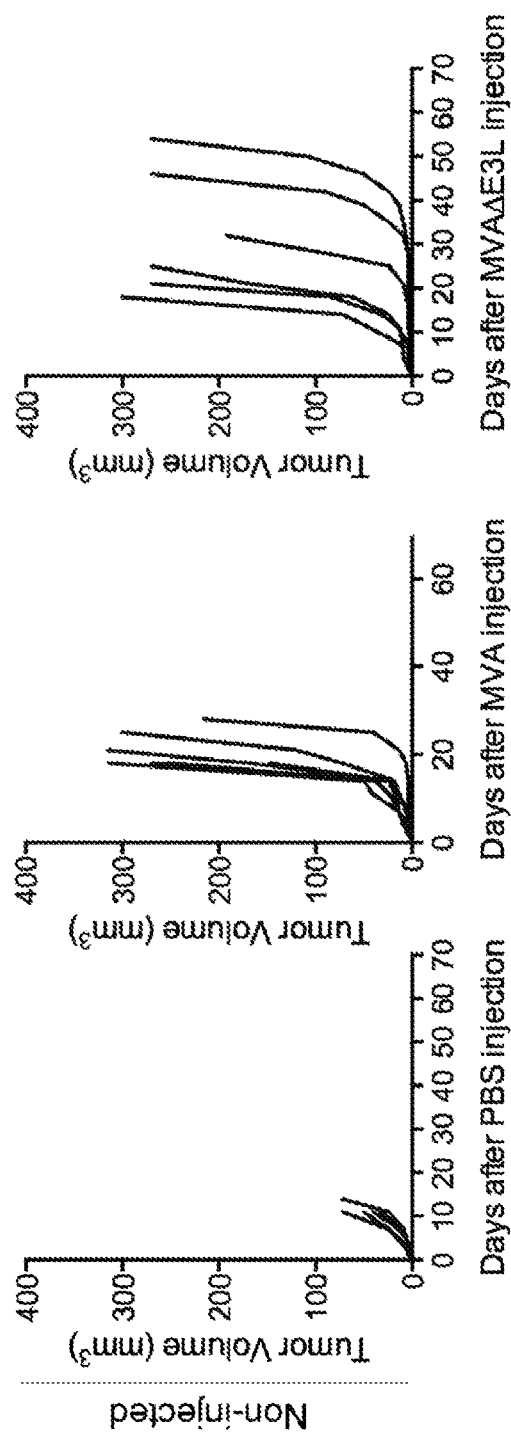

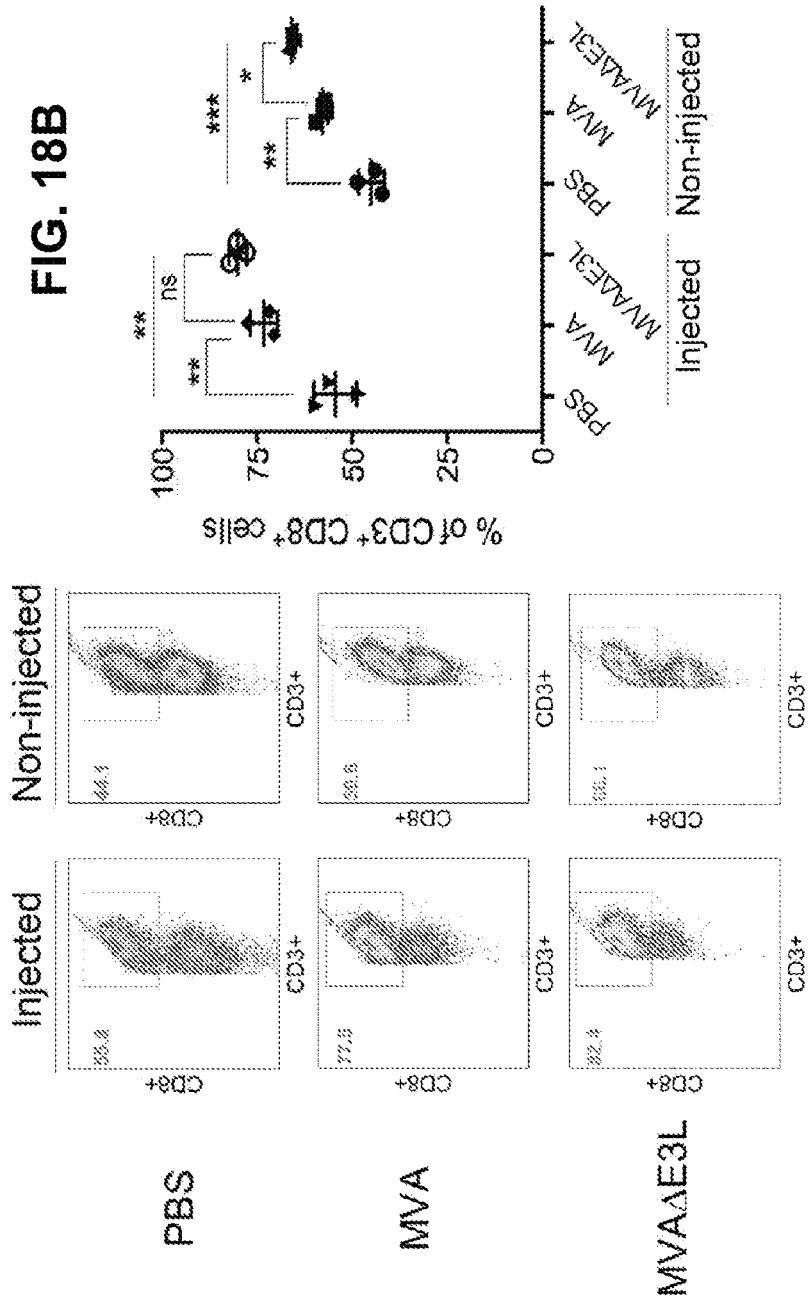

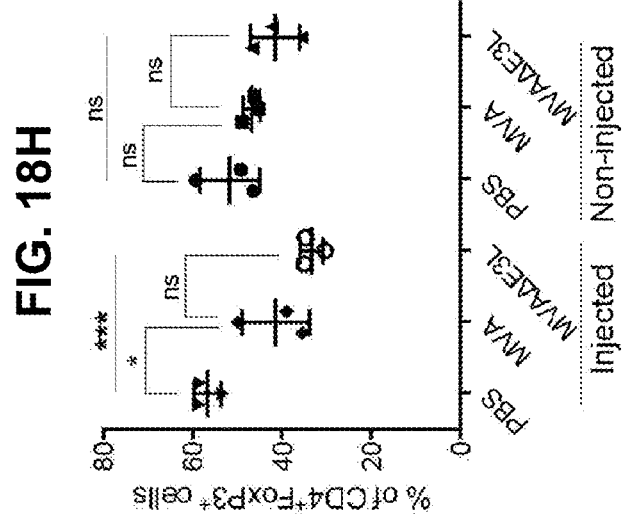
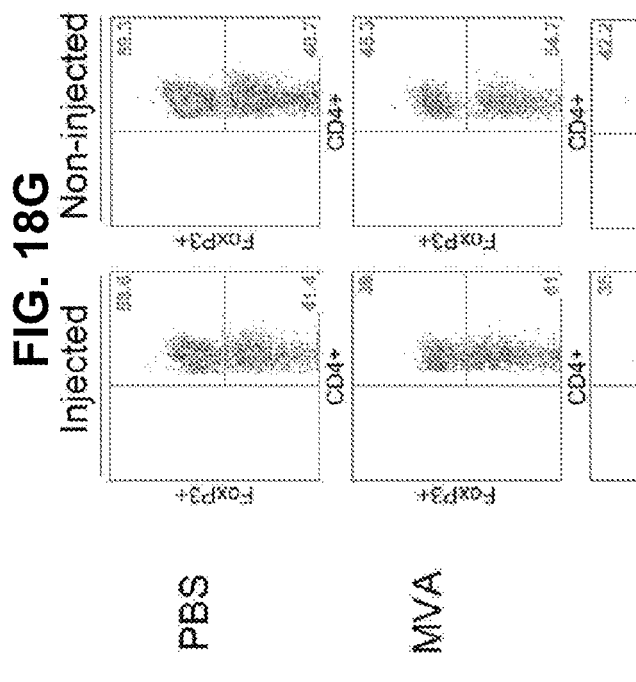

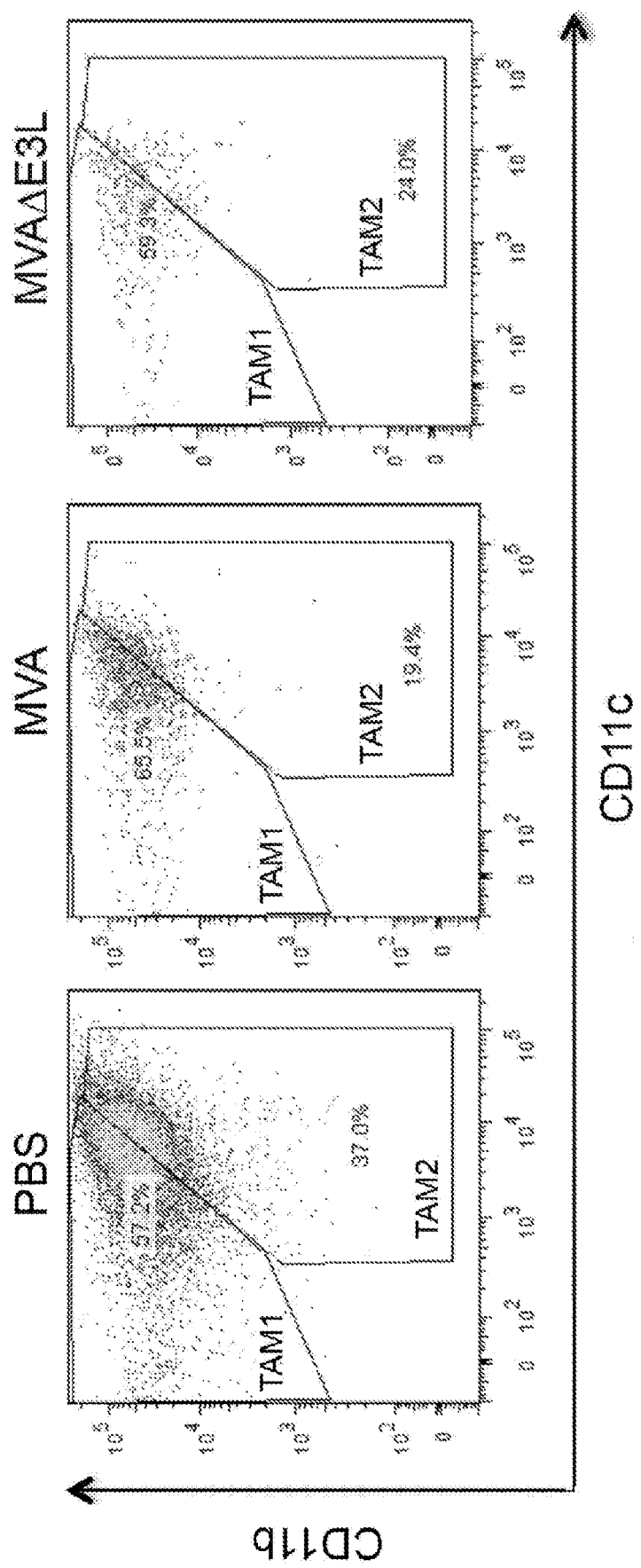

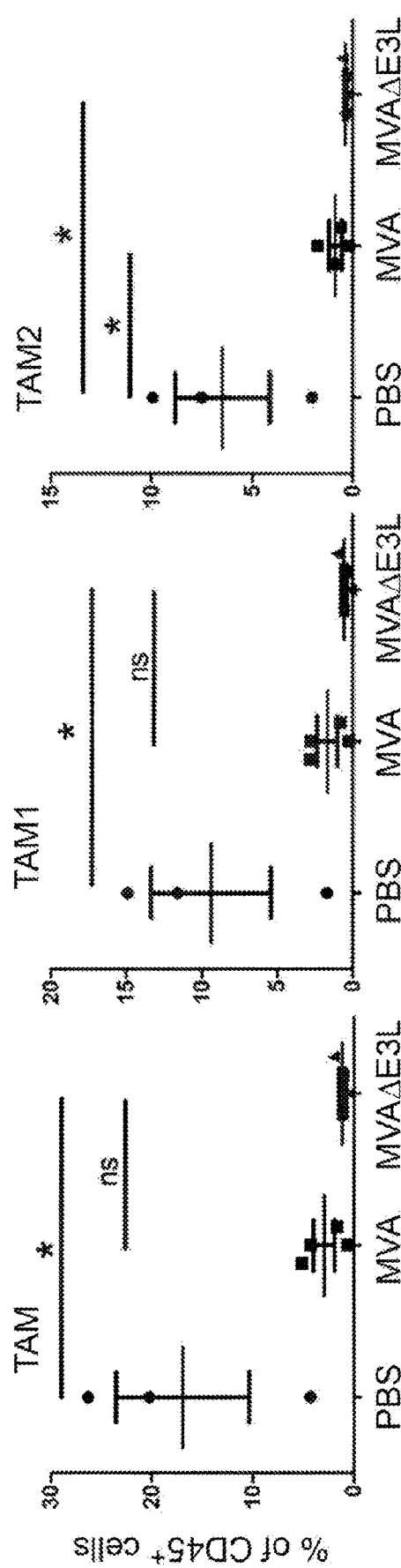

SEQUENCE LISTING

<160> NUMBER OF SEQ ID NOS: 14

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cctgtgtgat gcaggaacc                                                    19

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcacctccca ggcacaga                                                     18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tggagatgac ggagaagatg                                                   20

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttggatggca aaggcagt                                                     18

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcccacgtca aggagtattt cta                                               23

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acacacttgg cggttccttc                                                   20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aggcataacg cactaggttt                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agctggagtc acagaaggag                                              20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
attctttaag ggctggtctg a                                            21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cacctccaca tagcttacag t                                            21

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtcaggttgc ctctgtctca                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcagggaaga gtctggaaag                                              20

```
<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atcaagaagg tggtgaagca                                              20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agacaacctg gtcctcagtg t                                            21
```

USE OF MVA OR MVADELTAE3L AS IMMUNOTHERAPEUTIC AGENTS AGAINST SOLID TUMORS

CROSS-REFERENCE TO RELATED APPLICATIONS

This application is a continuation of U.S. patent application Ser. No. 16/741,634, filed Jan. 13, 2020, which is a continuation of U.S. patent application Ser. No. 15/565,609, filed Oct. 10, 2017 (now U.S. Pat. No. 10,548,930), which is a National Stage Application of PCT/US2016/028184, filed Apr. 18, 2016, which claims priority to U.S. Provisional Application No. 62/149,484, filed Apr. 17, 2015, each of which is incorporated herein by reference in its entirety.

GOVERNMENT SUPPORT

This invention was made with government support under AI073736 and AI095692 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 3, 2019, is named 115872-0732_SL.txt and is 3,526 bytes in size.

FIELD OF THE INVENTION

The present disclosure relates generally to the fields of oncology, virology and immunotherapy. It concerns the use of poxviruses, specifically the highly attenuated modified vaccinia virus Ankara (MVA), and a recombinant modified vaccinia Ankara virus with deletion of vaccinia virulence factor E3 (MVAΔE3L) as cancer immunotherapeutic agents as well as for the development of immunotherapeutic vectors. The foregoing poxviruses can also be used in combination with immune checkpoint blockade therapy.

BACKGROUND

Immune System and Cancer

Numerous studies support the importance of the differential presence of immune system components in cancer progression (1) (Jochems et al., *Exp Biol Med*, 236 (5): 567-579 (2011)). Clinical data suggest that high densities of tumor-infiltrating lymphocytes are linked to improved clinical outcome (2) (Mlecnik et al., *Cancer Metastasis Rev.;* 30: 5-12, (2011)). The correlation between a robust lymphocyte infiltration and patient survival has been reported in various types of cancer, including melanoma, ovarian, head and neck, breast, urothelial, colorectal, lung, hepatocellular, gallbladder, and esophageal cancer (3) (Angell et al., *Current Opinion in Immunology,* 25:1-7, (2013)). Tumor immune infiltrates include macrophages, dendritic cells (DC), mast cells, natural killer (NK) cells, naïve and memory lymphocytes, B cells and effector T cells (T lymphocytes), primarily responsible for the recognition of antigens expressed by tumor cells and subsequent destruction of the tumor cells by cytotoxic T cells.

Despite presentation of antigens by cancer cells and the presence of immune cells that could potentially react against tumor cells, in many cases the immune system does not get activated or is affirmatively suppressed. Key to this phenomenon is the ability of tumors to protect themselves from immune response by coercing cells of the immune system to inhibit other cells of the immune system. Tumors develop a number of immunomodulatory mechanisms to evade anti-tumor immune responses. For example, tumor cells secrete immune inhibitory cytokines (such as TGF-β) or induce immune cells, such as CD4$^+$ T regulatory cells and macrophages, in tumor lesions to secrete these cytokines. Tumors have also the ability to bias CD4$^+$ T cells to express the regulatory phenotype. The overall result is impaired T-cell responses and induction of apoptosis or reduced anti-tumor immune capacity of CD8$^+$ cytotoxic T cells. Additionally, tumor-associated altered expression of MEW class I on the surface of tumor cells makes them 'invisible' to the immune response (4) (Garrido et al. *Cancer Immunol. Immunother.* 59 (10), 1601-1606 (2010)). Inhibition of antigen-presenting functions and dendritic cell (DC) additionally contributes to the evasion of anti-tumor immunity (5) (Gerlini et al. *Am. J. Pathol.* 165 (6), 1853-1863 (2004)).

Moreover, the local immunosuppressive nature of the tumor microenvironment, along with immune editing, can lead to the escape of cancer cell subpopulations that do not express the target antigens. Thus, finding an approach that would promote the preservation and/or restoration of anti-tumor activities of the immune system would be of considerable therapeutic benefit.

Immune checkpoints have been implicated in the tumor-mediated downregulation of anti-tumor immunity and used as therapeutic targets. It has been demonstrated that T cell dysfunction occurs concurrently with an induced expression of the inhibitory receptors, CTLA-4 and programmed death 1 polypeptide (PD-1), members of the CD28 family receptors. PD-1 is an inhibitory member of the CD28 family of receptors that in addition to PD-1 includes CD28, CTLA-4, ICOS and BTLA. However, while promise regarding the use of immunotherapy in the treatment of melanoma has been underscored by the clinical use and even regulatory approval of anti-CTLA-4 (ipilimumab) and anti-PD-1 drugs (for example pembrolizumab and nivolumab) the response of patients to these immunotherapies has been limited. Recent clinical trials, focused on blocking these inhibitory signals in T cells (e.g., CTLA-4, PD-1, and the ligand of PD-1 PD-L1), have shown that reversing T cell suppression is critical for successful immunotherapy (6, 7) (Sharma et al., *Science* 348 (6230), 56-61 (2015); Topalian et al., *Curr Opin Immunol.* 24 (2), 202-217 (2012)). These observations highlight the need for development of novel therapeutic approaches for harnessing the immune system against cancer.

Poxviruses

Poxviruses, such as engineered vaccinia viruses, are in the forefront as oncolytic therapy for metastatic cancers (8) (Kirn et al., *Nature Review Cancer* 9, 64-71 (2009)). Vaccinia viruses are large DNA viruses, which have a rapid life cycle and efficient hematogenous spread to distant tissues (9) (Moss, In Fields Virology (Lippincott Williams & Wilkins, 2007), pp. 2905-2946). Poxviruses are well-suited as vectors to express multiple transgenes in cancer cells and thus to enhance therapeutic efficacy (10) (Breitbach et al., *Current pharmaceutical biotechnology* 13, 1768-1772 (2012)). Preclinical studies and clinical trials have demonstrated efficacy of using oncolytic vaccinia viruses and other poxviruses for treatment of advanced cancers refractory to conventional therapy (11-13) (Park et al., *Lacent Oncol* 9, 533-542 (2008); Kim et al., *PLoS Med* 4, e353 (2007); Thorne et al., *J Clin Invest* 117, 3350-3358 (2007)). Poxvirus-based oncolytic therapy has the advantage of killing cancer cells through the combination of cell lysis, apoptosis, and necrosis. It also triggers innate immune sensing pathway that facilitates the recruitment of immune cells to the tumors and the development of anti-tumor adaptive immune responses. The current oncolytic vaccinia strains in clinical trials (JX-594, for example) use wild-type vaccinia with deletion of thymidine kinase to enhance tumor selectivity, and with expression of transgenes such as granulocyte macrophage colony stimulating factor (GM-CSF) to stimulate immune responses (10) (Breitbach et al., Curr Pharm Biotechnol 13, 1768-1772 (2012)). Many studies have shown however that wild-type vaccinia has immune suppressive effects on antigen presenting cells (APCs) (14-17) (Engelmayer et al., J Immunol 163, 6762-6768 (1999); Jenne et al., Gene therapy 7, 1575-1583 (2000); P. Li et al., J Immunol 175, 6481-6488 (2005); Deng et al., J Virol 80, 9977-9987 (2006)), and thus adds to the immunosuppressive and immunoevasive effects of tumors themselves. By contrast, modified vaccinia virus Ankara (MVA), a highly attenuated vaccinia stain has moderate immune activating effects (18, 19) (Drillien et al., J Gen Virol 85, 2167-75 (2004); Dai et al., PLoS Pathog 10 (4), e1003989 (2014).

Modified vaccinia virus Ankara (MVA) is a highly attenuated vaccinia strain that is an important vaccine vector for infectious diseases and cancers. MVA was derived from vaccinia strain through more than 570 passages in chicken embryonic fibroblasts. MVA has a 31-kb deletion of the parental vaccinia genome and is non-replicative in most of mammalian cells. MVA was used in more than 120,000 people during WHO-sponsored smallpox vaccination, and was shown to be very safe for human use. Because of its safety and its ability to express foreign antigens, MVA has been investigated as a vaccine vector against HIV, tuberculosis, malaria, influenza, coronavirus, and CMV, as well as cancers (20-25) (Sutter et al., Current drug targets. Infectious disorders 3, 263-271 (2003); Gomez et al., Curr Gene Ther 8, 97-120 (2008); Gomez et al., Curr Gene Ther 11, 189-217 (2011); Goepfert et al., J Infect Dis 203, 610-619 (2011); Wyatt et al., Virology 372, 260-272 (2008); Garcia et al., Vaccine 29, 8309-8316 (2011)).

The investigation of MVA as cancer therapeutics has so far been limited to its use as a vaccine vector to express tumor antigens (26, 27) (Tagliamonte et al. Hum Vaccin Immunother 10, 3332-3346 (2014); Verardi et al., Hum Vaccin Immunother 8, 961-970 (2012)). Various tumor antigens have been expressed by MVA-based vectors, and some recombinant viruses are in various stages of clinical trials. For example, MVA-PSA-PAP expresses both prostate specific antigen (PSA) and prostate acid phosphatase (PAP) is in clinical trials for patients with metastatic prostate cancer. The recombinant virus MVA-brachyury-TRICOM expressing tumor antigen brachyury and T cell co-stimulatory molecules is also in clinical trials for patients with metastatic cancers. The recombinant virus MVA-p53 expressing p53 tumor suppressor, also in clinical trials, has been shown to be safe. Other tumor antigens that have been targeted include Her2, hMUC-1, TWIST, etc.

Although MVA is highly attenuated and moderately immunostimulatory, it retains multiple immune suppressive viral genes, including a key virulence factor, E3. MVAΔE3L, a recombinant MVA virus further attenuated by deletion of the vaccinia virulent factor E3, is unable to replicate in primary chicken embryo fibroblasts (CEFs), but retains its replication capacity in baby hamster kidney BHK-21 cells (28) (Hornemann et al., J Virol 77 (15), 8394-07 (2003). MVAΔF3L is capable of replicating viral DNA genomes in CEFs and is deficient in viral late protein synthesis (28) (Hornemann et al., J Virol 77(15), 8394-07 (2003). It also induces apoptosis in CEF (28) (Hornemann et al., J Virol 77(15), 8394-07 (2003)). MVAΔE3L infection of HeLa cells had similar effects, with impaired viral replication, viral late gene transcription and translation (29) (Ludwig et al., J Virol 79(4), 2584-2596 (2005)). MVAΔE3L also induces apoptosis in HeLa cells, possibly through activating the mitochondrial pathway (29) (Ludwig et al., J Virol 79 (4), 2584-2596 (2005)). dsRNA are produced during intermediate gene transcription, which can lead to the activation of 2'-5'-oligoadenylate synthase/RNase L and Protein Kinase R (PKR). In PKR-deficient MEFs, MVAΔE3L gains its ability to express intermediate and late proteins ((29) (Ludwig et al., J Virol 79(4), 2584-2596 (2005)).

One study suggests that pro-apoptotic protein Noxa plays a role in MVAΔE3L apoptosis induction (30) (Fischer et al., Cell Death Differ 13, 109-118 (2006)). Although an early study showed that MVAΔF3L induces higher levels of type I IFN in CEFs than MVA, the exact mechanism was not fully elucidated (28) (Hornemann et al., J Virol 77 (15), 8394-07 (2003).

One MVAΔE3L has been described in U.S. Pat. No. 7,049,145 incorporated by reference. It is infection competent but nonreplicative in most mammalian cells including mouse and human.

This disclosure focuses on the intratumoral delivery of MVA or MVAΔE3L as anticancer immunotherapeutic agents. It was hoped that intratumoral delivery of MVA or MVAΔE3L would elicit innate immune responses from tumor infiltrating immune cells (e.g. leukocytes), tumor cells, and tumor associated stromal cells, and lead to induction of type I IFN and proinflammatory cytokines and chemokines, which would result in the alteration of the tumor immune suppressive microenvironment.

The recent discovery of tumor neoantigens in various solid tumors indicates that solid tumors harbor unique neoantigens that usually differ from person to person (31, 32) (Castle et al., Cancer Res 72, 1081-1091 (2012); Schumacher et al., Science 348, 69-74 (2015) The recombinant viruses disclosed in this invention do not work by expressing tumor antigens. Intratumoral delivery of the present recombinant MVA viruses allows efficient cross-presentation of tumor neoantigens and generation of anti-tumor adaptive immunity within the tumors (and also extending systemically), and therefore lead to "in situ cancer vaccination" utilizing tumor differentiation antigens and neoantigens expressed by the tumor cells in mounting an immune response against the tumor.

Despite the presence of neoantigens generated by somatic mutations within tumors, the functions of tumor antigen-specific T cells are often held in check by multiple inhibitory mechanisms (33) (Mellman et al., Nature 480, 480-489 (2011)). For example, the up-regulation of cytotoxic T lymphocyte antigen 4 (CTLA-4) on activated T cells can compete with T cell co-stimulator CD28 to interact with CD80 (B71)/CD86 (B7.2) on dendritic cells (DCs), and thereby inhibit T cell activation and proliferation. CTLA-4 is also expressed on regulatory T (Treg) cells and plays an important role in mediating the inhibitory function of Tregs (34, 35) (Wing et al., Science 322, 271-275 (2008); Peggs, et al., J Exp Med 206, 1717-1725 (2009)). In addition, the expression of PD-L/PD-L2 on tumor cells can lead to the activation of the inhibitory receptor of the CD28 family, PD-1, leading to T cell exhaustion. Immunotherapy utilizing antibodies against inhibitory receptors, such as CTLA-4 and programmed death 1 polypeptide (PD-1), have shown remarkable preclinical activities in animal studies and clinical responses in patients with metastatic cancers, and have been approved by the FDA for the treatment of metastatic melanoma, non-small cell lung cancer, as well as renal cell carcinoma (6, 36-39) (Leach et al., *Science* 271, 1734-1746 (1996); Hodi et al., *NEJM* 363, 711-723 (2010); Robert et al., *NEJM* 364, 2517-2526 (2011); Topalian et al., *Cancer Cell* 27, 450-461 (2012); Sharma et al., *Science* 348 (6230), 56-61 (2015))

Melanoma

Melanoma, one of the deadliest cancers, is the fastest growing cancer in the US and worldwide. Its incidence has increased by 50% among young Caucasian women since 1980, primarily due to excess sun exposure and the use of tanning beds. According to the American Cancer Society, approximately 78,000 people in the US will be diagnosed with melanoma in 2015 and almost 10,000 people (or one person per hour) will die from melanoma. In most cases, advanced melanoma is resistant to conventional therapies, including chemotherapy and radiation. As a result, people with metastatic melanoma have a very poor prognosis, with a life expectancy of only 6 to 10 months. The discovery that about 50% of melanomas have mutations in BRAF (a key tumor-promoting gene) opened the door for targeted therapy in this disease. Early clinical trials with BRAF inhibitors showed remarkable, but unfortunately not sustainable, responses in patients with melanomas with BRAF mutations. Therefore, alternative treatment strategies for these patients, as well as others with melanoma without BRAF mutations, are urgently needed.

Human pathological data indicate that the presence of T-cell infiltrates within melanoma lesions correlates positively with longer patient survival (40) (Oble et al. *Cancer Immun.* 9, 3 (2009)). The importance of the immune system in protection against melanoma is further supported by partial success of immunotherapies, such as the immune activators IFN-α2b and IL-2 (41) (Lacy et al. *Expert Rev Dermatol* 7 (1):51-68 (2012)) as well as the unprecedented clinical responses of patients with metastatic melanoma to immune checkpoint therapy, including anti-CTLA-4 and anti-PD-1/PD-L1 either agent alone or in combination therapy (6, 7, 37, 42-45) (Sharma and Allison, Science 348(6230), 56-61 (2015); Hodi et al., NEJM 363 (8), 711-723 (2010); Wolchok et al., Lancet Oncol. 11 (6), 155-164 (2010); Topalian et al., NEJM 366 (26), 2443-2454 (2012); Wolchok et al., NEJM 369 (2), 122-133 (2013); Hamid et al., NEJM 369 (2), 134-144 (2013); Tumeh et al., Nature 515 (7528), 568-571 (2014). However, many patients fail to respond to immune checkpoint blockade therapy alone. The addition of virotherapy might overcome resistance to immune checkpoint blockade, which is supported by animal tumor models (46) (Zamarin et al., Sci Transl Med 6(226), 2014).

Type I IFN and the Cytosolic DNA-Sensing Pathway in Tumor Immunity

Type I IFN plays important roles in host antitumor immunity (47) (Fuertes et al., *Trends Immunol* 34, 67-73 (2013)). IFNAR1-deficent mice are more susceptible to develop tumors after implantation of tumor cells; Spontaneous tumor-specific T cell priming is also defective in IFNAR1-deficient mice (48, 49) (Diamond et al., *J Exp Med* 208, 1989-2003 (2011); Fuertes et al., *J Exp Med* 208, 2005-2016 (2011)). More recent studies have shown that the cytosolic DNA-sensing pathway is important in the innate immune sensing of tumor-derived DNA, which leads to the development of antitumor CD8$^+$ T cell immunity (50) (Woo et al., *Immunity* 41, 830-842 (2014)). This pathway also plays a role in radiation-induced antitumor immunity (51) (Deng et al., *Immunity* 41, 843-852 (2014)). Although spontaneous anti-tumor T cell responses can be detected in patients with cancers, cancers eventually overcome host antitumor immunity in most patients. Novel strategies to alter the tumor immune suppressive microenvironment would be beneficial for cancer therapy.

SUMMARY

The present disclosure relates to the discovery that both MVA and MVAΔE3L have properties that can be used effectively in developing immunotherapies against cancers. Intratumoral injection of MVA or MVAΔE3L leads to tumor regression and even eradication, and to the generation of systemic antitumoral immunity. Therefore, both MVA and MVAΔE3L can be used as immunotherapy for the treatment of solid tumors. Moreover, the combination of intratumoral delivery of MVA-based virotherapy and immune checkpoint blockade (or checkpoint agonist therapy), delivered either systemically or intratumorally, is anticipated to lead to enhanced antitumoral activities in injected tumors as well as non-injected distant tumors.

The present inventors observed that MVA infection of conventional dendritic cells (cDCs) triggers type I IFN via the cytosolic DNA-sensing pathway mediated by the newly discovered cytosolic DNA sensor cGAS (cyclic GMP-AMP synthase) and its adaptor STING (stimulator of IFN genes). By contrast, wild-type vaccinia infection of cDCs fails to induce type I IFN. They also observed that a recombinant MVA virus with deletion of vaccinia virulence factor E3 (MVAΔF3L) infection of cDCs induces higher levels of type I IFN than MVA. It also activates the innate immune-sensing pathways for MVAΔE3L virus in cDCs, and induces type I IFN, inflammatory cytokines and chemokines, and apoptosis in cancer cells by MVA and MVAΔE3L.

These observations lead to the possibility of using these highly attenuated modified vaccinia viruses as immune activators to alter the tumor-induced immune suppressive microenvironment through induction of type I IFN and other inflammatory cytokines and chemokines in tumor cells as well as in immune cells (in other words, to induce antitumor immune responses in the host or to enhance antitumor responses that may already be ongoing and to reverse their suppression). This in turn leads to more efficient tumor antigen presentation, and to the generation and activation of anti-tumor cytotoxic CD8$^+$ T cells, effector CD4$^+$ T cells, as well as the reduction of immune suppressive CD4$^+$ regulatory T cells and tumor-associated macrophages. Because MVA and MVAΔE3L are safe vaccine vectors the use of such viral vectors within the tumor allows tumor antigen release, efficient presentation, and the generation of antitumor effector and memory T cell responses and antitumor antibody production. Indeed, the inventors observed that MVA and MVAΔE3L used intratumorally lead to activation of dendritic cells and improved presentation of tumor antigens (including oncogenic viral antigens, tumor differentiation antigens, and tumor neoantigens).

The localized (e.g., intratumoral) injection of MVA and MVAΔE3L can be used for various stages of tumors. For early stage cancer, virotherapy can be used 2-3 weeks prior to surgical removal of the tumor. During that time frame, the host would have developed systemic anti-tumor adaptive immunity. For advanced cancer, virotherapy can be used in combination with other treatment modalities, including surgery, chemotherapy, targeted therapy, radiation, and immune checkpoint therapy, which will be detailed below.

Based on results obtained by the present inventors with inactivated MVA and described in PCT US2016/019663 filed Feb. 25, 2016, incorporated by reference in its entirety for all purposes, the present inventors hypothesize that intratumoral injection of MVA or MVAΔE3L would provide additional beneficial effects to a PD-1 or CTLA-4 targeting approach, through induction of type I IFN in immune cells and cancer cells, altering the tumor immune suppressive environment via the activation of immune cells including dendritic cells as well as facilitating tumor antigen presentation.

In one aspect, the disclosure is directed to a method for treating a solid malignant tumor in a subject comprising delivering to tumor cells of the subject an amount of MVA or MVAΔE3L effective to induce the immune system of the subject to mount an immune response against the tumor, for example as set forth above in this Summary so as to accomplish one or more of the following (regardless of order): reduce the size of the tumor, eradicate the tumor, inhibit growth of the tumor, or inhibit metastasis or metastatic growth of the tumor.

In another aspect, the disclosure is directed to a method for treating a malignant tumor comprising:
  delivering to tumor cells of the subject an amount of MVA or MVAΔE3L effective to induce the immune system of the subject to mount an immune response against the tumor.

In some embodiments one or more of the following specific features are also present:
  the recruitment and activation of effector T cells is accompanied by a reduction of regulatory $CD4^+$ cells in the tumor;
  the tumor is melanoma or colon carcinoma;
  a regimen of periodic delivery of MVA or MVAΔE3L is continued until it induces tumor regression or eradication;
  a regimen of periodic delivery of the MVA or MVAΔE3L is continued for several weeks, months or years or indefinitely as long as benefits persist;
  a regimen of periodic delivery of the MVA or MVAΔE3L is continued indefinitely until the maximum tolerated dose is reached;
  delivery of the MVA or MVAΔE3L is by parenteral injection;
  delivery of the MVA or MVAΔE3L is by intratumoral injection;
  delivery of the MVA or MVAΔE3L is by intravenous injection;
  the subject is a human;
  the MVA or MVAΔE3L is delivered at a dosage per administration within the range of about $10^5$-$10^{10}$ plaque-forming units (pfu);
  the MVA or MVAΔE3L is delivered at a dosage per administration within the range of about $10^6$ to about $10^9$ plaque-forming units (pfu);
  the amount delivered is sufficient to infect all tumor cells;
  the delivery is repeated with a frequency within the range from once per month to two times per week;
  the treatment continues for a period of weeks, months or years;
  the delivery is repeated with a frequency within the range from once per month to two times per week;
  the melanoma is metastatic melanoma.

Delivery of MVA or MVAΔE3L in the locale of the tumor induces the immune system of a subject afflicted with a malignant solid tumor to mount an immune response against the tumor. Stimulation of the subject's immune system against the tumor can be manifest (and may indeed be tested) by one or more of the following immunological effects:
  an increase in antitumor cytotoxic $CD8^+$ and effector $CD4^+$ T cells within the tumor and/or in tumor-draining lymph nodes;
  induction of maturation of dendritic cells infiltrating said tumor through induction of type I IFN;
  induction of activated antitumor effector T cells in the subject recognizing tumor cells within the tumor and/or in tumor draining lymph nodes;
  reduction of immune suppressive (regulatory) $CD4^+$ T cells within the tumor; and
  induction of cells of the tumor to express MHC Class I on their surface and to produce Type I IFN.

More particularly, in one aspect, the present disclosure is directed to a method for treating a subject afflicted with a malignant solid tumor r, the method comprising delivering to the cells of the tumor a modified vaccinia virus selected from the group of MVA and MVAΔE3Land combinations thereof and thereby treating the tumor.

In some embodiments, the amount of said virus is effective to bring about one or more of the following:
  a. induce the immune system of the subject to mount an immune response against the tumor or enhance an ongoing response by the immune system against the tumor;
  b. reduce the size of the tumor;
  c. eradicate the tumor;
  d. inhibit growth of the tumor;
  e. inhibit metastasis of the tumor; and
  f. reduce or eradicate metastatic tumor.

In another aspect the disclosure provides a method for treating a solid malignant tumor in a subject comprising delivering to tumor cells of the subject an amount of MVA or MVAΔE3L or a combination thereof effective to induce the immune system of the subject to mount an immune response against the tumor or to enhance an ongoing immune response of said subject against the tumor, so as to accomplish one or more of the following: reduce the size of the tumor, eradicate the tumor, inhibit growth of the tumor, inhibit metastatic growth of the tumor, induce apoptosis of tumor cells or prolong survival of the subject.

In another aspect, the present disclosure is directed to A method for treating a solid malignant tumor in a subject comprising delivering to a tumor of the subject an amount of modified vaccinia virus Ankara (MVA) or MVAΔE3L or a combination of both effective to bring about at least one of the following immunologic effects:
  a. increase at least one of effector $CD8^+$ T cells and effector $CD4^+$ T cells within the tumor and/or in tumor-draining lymph nodes;
  b. induce maturation of dendritic cells infiltrating said tumor through induction of type I IFN;
  c. reduce immune suppressive (regulatory) $CD4^+$ T cells within the tumor;
  d. reduce immune suppressive tumor-associated macrophages (TAM) within the tumor;
  e. induce type I IFN, inflammatory cytokine and chemokine production in immune cells and stromal fibroblasts.

In some embodiments of each of the foregoing aspects:
  the MVA or MVAΔE3L is not harboring nucleic acid encoding or expressing a tumor antigen;
  the tumor includes tumor located at the site of MVA or MVAΔE3L or tumor located elsewhere in the body of the subject;

the recruitment and activation of CD4+ effector T cells is accompanied by a reduction of regulatory CD4+ cells in said tumor.

the tumor is melanoma or colon carcinoma or another solid tumor;

delivery of the MVA or MVAΔE3L is continued until it induces tumor regression or eradication;

delivery of the MVA or MVAΔE3L is continued for several weeks, months or years or indefinitely as long as benefits persist or a maximum tolerated dose is reached;

delivery of the MVA or MVAΔE3L is continued indefinitely until the maximum tolerated dose is reached;

delivery of the MVA or MVAΔE3L is by parenteral, e.g., intratumoral or intravenous injection;

the subject is a human;

MVA or MVAΔE3L is delivered at a dosage per administration within the range of about $10^5$-$10^{10}$ plaque-forming units (pfu);

the MVA or MVAΔE3L is delivered at a dosage per administration within the range of about $10^6$ to about $10^9$ plaque-forming units (pfu);

the amount delivered is sufficient to infect all tumor cells;

the delivery is repeated with a frequency within the range from once per month to two times per week;

the delivery is repeated once weekly;

the melanoma is metastatic melanoma;

the MVA is MVAΔE3L;

In still another aspect, the present disclosure provides a method for treating a malignant tumor in a subject, the method comprising delivering to tumor cells of the subject a virus selected from the group consisting of modified vaccinia Ankara (MVA), MVAΔE3L and a combination thereof in an amount effective to induce the immune system of the subject to ount an immune response against the tumor or to enhance an ongoing immune response f said subject against the tumor and conjointly administering to the subject a second amount of an immune checkpoint blocking agent or an immune checkpoint agonist effective to block immune suppressive mechanisms within the tumor.

In more specific embodiments:

the immune suppressive mechanisms are elicited by tumor cells, stromal cells, or tumor infiltrating immune cells;

the administration is by parenteral route;

the delivery is by intratumoral injection and the administration is by intravenous route;

both the delivery and the administration are by intravenous route;

both the delivery and the administration are by intratumoral injection; the immune checkpoint blocking agent is selected from the group consisting of PD-1 inhibitors, PD-L1 inhibitors, CTLA4 inhibitors, inhibitory antibodies against LAG-3 (lymphocyte activation gene 3), TIM3 (T cell Immunoglobulin and Mucin-3), B7-H3, and TIGIT (T-cell immunoreceptor with Ig and ITIM domains); and the immune checkpoint agonist is selected from the group consisting of anti-ICOS antibody anti-OX40 antibody agonist antibody against 4-1BB (CD137) and against GITR;

any one of said inhibitors or agonists is an antibody;

the tumor is primary or metastatic melanoma or primary or metastatic colon carcinoma or another solid tumor.

the virus is delivered and the immune checkpoint blocking agent is administered each according to its own administration schedule of spaced apart intervals;

a first dose of the virus is delivered first and after a lapse of time a first dose of the immune checkpoint blocking agent is administered;

the delivery and administration occur in parallel during the same overall period of time;

one or both of the virus and the immune checkpoint blocking agent are respectively delivered and administered during a period of time of several weeks, months or years, or indefinitely as long as benefits persist and a maximum tolerated dose is not reached;

the virus is delivered at a dosage per administration within the range of about $10^5$-$10^{10}$ plaque-forming units (pfu);

the virus is delivered at a dosage per administration within the range of about $10^6$ to about $10^9$ plaque-forming units (pfu);

the virus delivery is repeated with a frequency within the range from once per month to two times per week;

the virus delivery is repeated once weekly;

the virus is MVAΔE3L;

the subject is a human;

the virus is MVA;

the virus and the immune checkpoint blocking agent or agonist are administered simultaneously;

the virus and the immune checkpoint blocking agent or agonist are administered in the same composition;

the MVA and the immune checkpoint blocking agent are delivered intratumorally;

the virus and the immune checkpoint blocking agent are administered sequentially;

the inactivated MVA and the immune checkpoint blocking agent are delivered intratumorally.

In an additional aspect, the present disclosure provides a composition for use in treating a solid tumor comprising an amount of a modified vaccinia virus selected from the group consisting of MVA and MVAΔE3L and combinations thereof effective to induce the immune system of a host to whom said composition will be administered to mount an immune response against the tumor or to enhance an ongoing immune response of the host against the tumor; and a pharmaceutically acceptable carrier or diluent.

In more specific embodiments of the composition the effective amount is within the range of about $10^5$-$10^{10}$ plaque-forming units (pfu) in a unit dosage form; or the effective amount is within the range of $10^6$ to $10^9$ pfu.

BRIEF DESCRIPTION OF THE DRAWINGS

FIG. 1A are graphs showing secretion levels of IFN-α and IFN-β in GM-CSF-BMDCs at 1, 4, 8, 14, and 22 hours post infection with WT VAC or MVA. FIG. 1B are bar graphs showing mRNA levels of IFNA4 and IFNB in GM-CSF-BMDCs at 6 hours post infection with WT VAC or MVA.

FIGS. 2A-2C are a series of bar graphs showing that transcription factors IRF3/IRF7 and the type I IFN positive feedback loop mediated by IFNAR1 are required for the induction of type I IFN in murine cDCs by MVA. FIGS. 2A-2C are bar graphs of IFN-α and IFN-β concentrations in GM-CSF-BMDCs generated from IRF3$^{-/-}$ (2A), IRF7–/– (2B), IFNAR1$^{-/-}$(2C) mice, or their age-matched WT controls. Data are means±SEM (n=3). A representative experiment is shown, repeated twice. *, p<0.05; , p<0.01; *, p<0.001.

FIGS. 3A-3D are a series of graphical representations showing that STING is required for the induction of type I IFN and IRF3 phosphorylation by MVA in BMDCs. FIG. 3A shows bar graphs of IFN-α and IFN-β secretion levels in GM-CSF-BMDCs cell generated from Sting$^{+/+}$ and Sting$^{Gt/Gt}$ mice, stimulated with LPS or infected with MVA. FIG. 3B shows mRNA expression levels of IFNA4 and IFNB in GM-CSF-BMDCs cell generated from Sting$^{+/+}$ and Sting$^{Gt/Gt}$ mice and infected with MVA. FIG. 3C is a scanned image of immunoblot showing the proteins levels of phospho-TBK1, TBK1, phosphoserine-396 of IRF3, IRF3, and GAPDH. "hpi", hours post infection, "M", mock infection control. FIG. 3D are bar graphs showing the secretion levels of IFN-α and IFN-β in Sting$^{Gt/Gt}$, IRF3$^{-/-}$ and age-matched WT C57B/6 control mice infected with MVA. Data are means±SD. Results shown are representative of two independent experiments.

FIG. 4A are bar graphs showing IFN-α and IFN-β secretion levels in GM-CSF-BMDCs generated from cGAS$^{-/-}$ mice and its age-matched WT controls, and infected with MVA. Data are means±SEM (n=3). A representative experiment is shown, repeated twice (*, p<0.001). FIG. 4B are bar graphs showing mRNA expression levels of IFNA4 and IFNB in GM-CSF-BMDCs cell generated from cGAS$^{-/-}$ mice and its age-matched WT controls, and infected with MVA. Data are means±SEM (n=3). A representative experiment is shown, repeated twice (*, p<0.001). FIG. 4C is a scanned image of immunoblot showing the protein levels of phospho-TBK1, TBK1, phosphoserine-396 of IRF3, IRF3, and GAPDH in cGAS$^{+/+}$ and cGAS$^{-/-}$ cDCs infected with MVA. "hpi", hours post infection.

FIG. 5A is a scanned image of an immunoblot showing protein levels of E3 and β-actin in GM-CSF-BMDCs infected with WT VAC, MVA, or MVAΔE3L. "hpi," hours post infection, "M", mock infection control. FIG. 5B are bar graphs showing mRNA levels of IFNA4 and IFNB in GM-CSF-BMDCs infected with MVA or with MVAΔE3L. Data are means±SEM (n=3). A representative experiment is shown, repeated twice. *, p<0.001; comparisons were made between MVA and MVAΔE3L infected cells. FIG. 5C are bar graphs showing mRNA levels of IFNA4 and IFNB in GM-CSF-BMDCs generated from IRF3$^{-/-}$ mice and age-matched WT C57B/6 mice and infected with MVA or with MVAΔE3L. Data are means±SEM (n=3). A representative experiment is shown, repeated twice. *, p<0.001; comparisons were made between MVA and MVAΔE3L infected cells. FIG. 5D is a scanned image of an immunoblot showing protein levels of p-IRF3 and β-actin in GM-CSF-BMDCs infected with MVA or with MVAΔE3L.

FIG. 6A includes bar graphs showing mRNA levels of IFNA4 and IFNB in cGAS$^{+/+}$ and cGAS$^{-/-}$ cDCs infected with MVAΔE3L. FIG. 6B includes bar graphs showing IFN-α and IFN-β secretion levels in cGAS$^{+/+}$ and cGAS$^{-/-}$ cDCs infected with MVAΔE3L or treated with cGAMP, an agonist for STING. FIG. 6C is a scanned image of an immunoblot showing protein levels of p-IRF3 and GAPDH in cGAS$^{+/+}$ and cGAS$^{-/-}$ cDCs infected with MVAΔE3L.

FIG. 7A shows protein levels of p-IRF3 and β-actin in cDCs generated from WT, STING$^{Gt/Gt}$, or MAVS$^{-/-}$ mice, and infected with MVAΔE3L or not treated (NT). "hpi", hours post infection. FIG. 7B shows protein levels of phospho-TBK1, TBK1, phosphoserine-396 of IRF3, IRF3, and GAPDH in cDCs generated from WT or STING$^{Gt/Gt}$/MDA5$^{-/-}$ (DKO) mice, and infected with MVAΔE3L or MVA. "hpi", hours post infection.

FIGS. 8A-8H are a series of bar graphs showing that MVA and MVAΔE3L infection of murine primary fibroblasts leads to induction of gene expression of Ifnb (FIG. 8A), Cc14 (FIG. 8B), Il6 (FIG. 8C), and Cc15 (FIG. 8D), which is largely dependent on cGAS. "NT", not treated. MVAΔE3L-induced expression of Ifnb (FIG. 8E), Cc14 (FIG. 8F), Il6 (FIG. 8G), and Cc15 (FIG. 8H) is completely abolished in STING and MDA5-double deficient murine primary fibroblasts.

FIGS. 10A-10F are a series of bar graphs showing that MVAΔE3L infection leads to higher secretion levels of Ifna4 (FIG. 10A), Ifnb (FIG. 10B), Il6 (FIG. 10C), Tnf (FIG. 10D), Cc14 (FIG. 10E), and Cc15 (FIG. 10F) than MVA in B16-F10 melanoma cells. "NT", not treated.

FIG. 11A shows protein levels of PARP, cleaved PARP, and β-actin in B16-F10 melanoma cells infected with MVA or MVAΔE3L. FIG. 11B shows protein levels of MCL-1, and β-actin in B16-F10 melanoma cells infected with MVA or MVAΔE3L. "hpi", hours post infection. FIG. 11C shows levels of phosphorylated IRF3 and GAPDH in B16-F10 melanoma cells infected with MVA or MVAΔE3L. "hpi", hours post infection.

FIGS. 12A-12E are a series of graphs showing that intratumoral injection of MVA and MVAΔE3L leads to prolonged survival of tumor-bearing mice and eradication of tumors in some mice. FIGS. 12A-12C are graphs of tumor volume over time in individual mice injected with PBS (A), MVA (B), and MVAΔE3L (C). FIG. 12D is a Kaplan-Meier survival curve of tumor-bearing mice injected with PBS, MVA, or MVAΔE3L. **, p<0.0001 (MVA vs. PBS group); *, p<0.001 (MVAΔE3L vs. PBS group). FIG. 12E is a Kaplan-Meier survival curve of tumor-free mice after successful treatment with MVA or MVAΔE3L, and challenged with B16-F10 melanoma cells at the contralateral side. Naïve mice have never received any tumor cells or viruses in the past.

FIGS. 13A-13I are a series of graphical representations of data showing that intratumoral injection with MVA leads to immunological changes in the tumor microenvironment. FIG. 13A-13B are dot-plots of flow cytometric analysis of CD4$^+$ cells expressing FoxP3 in tumors treated with either PBS (13A) or MVA (13B). FIGS. 13D-13E are dot-plots of flow cytometric analysis of CD8$^+$ cells expressing Granzyme B in tumors treated with either PBS (13D) or MVA (13E). FIGS. 13G-13H are scatterplots of flow cytometric analysis of CD8$^+$ cells expressing Ki-67 in tumors treated with either PBS (13G) or MVA (13H). FIG. 13C is a graph depicting percentages of CD4$^+$ Foxp3$^+$ in tumors treated with PBS or MVA. FIG. 13F is a graph depicting percentages of Granzyme B$^+$ CD8$^+$ cells in tumors treated with PBS or MVA. FIG. 13I is a graph depicting percentages of CD8$^+$ Ki-67$^+$ in tumors treated with PBS or MVA.

FIGS. 14A-14F are a series of graphical representations of data showing that intratumoral injection with MVA induces immunological changes in the tumor draining lymph nodes (TDLNs). FIGS. 14A-14B are dot-plots of flow cytometric analysis of Granzyme B$^+$ CD8$^+$ cells in TDLNs of PBS (14A) or MVA (14B) treated mice. FIGS. 14C-14D are dot-plots of flow cytometric analysis of Ki-67$^+$ CD8$^+$ cells in TDLNs of PBS (14D) or MVA (14E) treated mice. FIG. 14C is a graph depicting percentages of Granzyme B$^+$ CD8$^+$ cells in TDLNs from mice treated with PBS or MVA. FIG. 14F is a graph depicting percentages of CD8$^+$ Ki-67$^+$ in TDLNs from mice treated with PBS or MVA.

FIGS. 15A-15I are a series of graphic representations showing that MVAΔE3L induces type I IFN and inflammatory cytokines/chemokines production in MC38 colon cancer cells. FIGS. 15A-15D are bar graphs showing protein levels of IFN-β (15A), IL-6 (15B), CCL4 (15C), and CCL5 (15D) in the supernatants of MC38 colon cancer cells infected with MVA or MVAΔE3L. FIGS. 15E-15H are bar graphs showing the mRNA levels of Ifnb (15E), Il6 (15F), Ccl4 (15G), and Ccl5 (15H) in MC38 colon cancer cells at 6 h post infection with MVA or MVAΔE3L. FIG. 15I is a scanned image of a Western blot showing protein levels of PARP, cleaved-PARP, phosphor-IRF-3, IRF3, and β-actin. "hpi", hours post infection.

FIGS. 16A-16C are a series of graphs showing that MVAΔE3L inhibits tumorigenesis in murine model of colon carcinoma. FIGS. 16A and 16B are plots of tumor volume v. time from injection of PBS or virus in mice showing that intratumoral injection of MVAΔE3L is effective for the treatment of murine colon adenocarcinoma (MC38 cells) implanted unilaterally in mice (C57B/6). The tumor volumes of mice treated with PBS or MVAΔE3L groups prior to treatment (day 0) and up to 45 days post-treatment are shown. FIG. 16C is a Kaplan-Meier survival curve for the treated mice (MVAΔE3L) versus control mice (PBS). ***, p<0.001 (MVAΔE3L vs. PBS group).

FIGS. 17A-17G are a series of graphical representations of data showing that intratumoral injection of MVA or MVAΔE3L induced antitumor effects in non-injected distant tumors in a murine B16-F10 melanoma bilateral implantation model. FIG. 17A-17F are graphs of injected (17A, 17C, 17E) and non-injected (17B, 17D, 17F) tumor volume plotted against time (days) after PBS, MVA, or MVAΔE3L injection respectively. FIG. 17G is a Kaplan-Meier survival curve of tumor-bearing mice (B16-F10 cells) injected with PBS (filled circles), MVA (filled squares), or MVAΔE3L (filled triangles). **, p<0.0001 (MVAΔE3L vs. PBS group); *, p<0.001 (MVA vs. PBS group).

FIGS. 18A-18L are a series of graphical representations of data showing that intratumoral injection of MVA or MVAΔE3L induces activated effector CD8$^+$ and CD4$^+$ T cells and reduces regulator CD4$^+$ T cells in both injected and non-injected tumors in a murine B16-F10 melanoma bilateral implantation model. FIG. 18A is dot-plots of flow cytometric analysis of CD3$^+$ CD8$^+$ T cells in both injected and non-injected tumors treated with PBS, MVA or MVAΔE3L. FIG. 18B is a graph of % CD3$^+$ CD8$^+$ T cells in both injected and non-injected tumors treated with PBS, MVA or MVAΔE3L. FIGS. 18C and 18E are dot-plots of flow cytometric analysis of CD8$^+$ cells expressing Granzyme (18C) or Ki-67 (18E). FIGS. 18D and 18F are graphs of % CD8$^+$Granzyme B$^+$ (18D), CD8$^+$Ki-67$^+$ (18F) T cells in both injected and non-injected tumors treated with PBS, MVA or MVAΔE3L. FIG. 18G are dot-plots of flow cytometric analysis of CD4$^+$Foxp3$^+$ T cells in both injected and non-injected tumors treated with PBS, MVA or MVAΔE3L. FIG. 18H is a graph of % CD4$^+$Foxp3$^+$ T cells in both injected and non-injected tumors treated with PBS, MVA or MVAΔE3L. FIGS. 18I and 18K are dot-plots of flow cytometric analysis of CD4$^+$ cells expressing Granzyme B$^+$ (18I) or Ki-67 (18K). FIGS. 18J and 18L are graphs of % CD4$^+$ Granzyme B$^+$ (18J), CD8$^+$Ki-67$^+$ (18L) T cells in both injected and non-injected tumors treated with PBS, MVA or MVAΔE3L. (*, p<0.05; , p<0.01; *, p<0.001; ****, p<0.0001).

FIGS. 19A-19D is a series of graphical representations of data showing that intratumoral injection of MVA or MVAΔE3L reduces tumor-associated macrophages (TAMs) in a murine B16-F10 melanoma model. FIG. 19A are dot-plots of flow cytometric analysis of TAM cells (CD45$^+$ Ly6C$^-$MHCII$^+$CD24$^{lo}$F4/80$^+$CD11b$^+$CD11c$^+$) in tumors treated with PBS, MVA or MVAΔE3L. FIG. 19B-19D are graphs of % TAM, TAM1 (CD11C$^{lo}$CD11b$^{hi}$), and TAM2 (CD11C$^{hi}$CD11b$^{lo}$) in CD45$^+$ cells in tumors treated with PBS, MVA or MVAΔE3L. (*, p<0.05; ns: non-significant).

DETAILED DESCRIPTION

Definitions

Figure 1A:
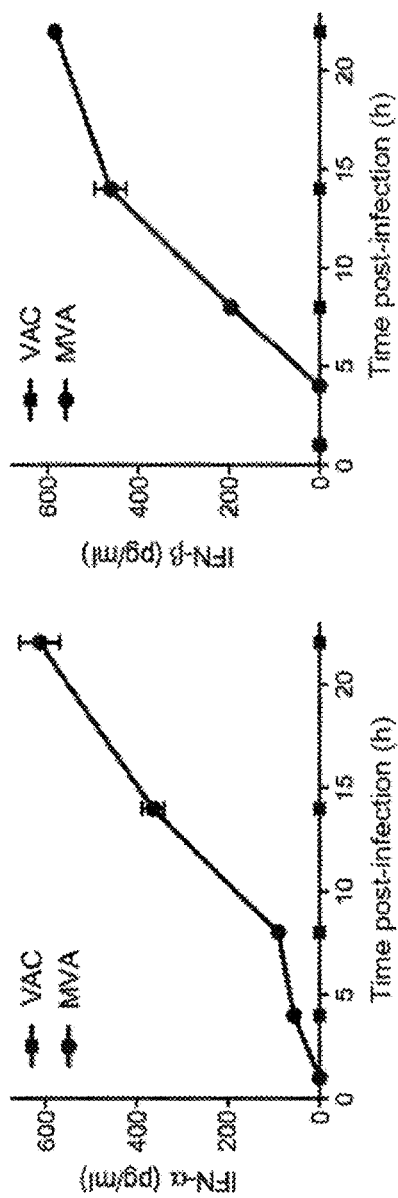
FIGS. 1A-1B are a series of graphical representations of data showing that MVA induces type I IFN production in murine cDCs.

As used herein the following terms shall have the meanings ascribed to them below unless the context clearly indicates otherwise:

"Cancer" refers to a class of diseases of humans and animals characterized by uncontrolled cellular growth. Unless otherwise explicitly indicated, the term "cancer" may be used herein interchangeably with the terms "tumor," "malignancy," "hyperproliferation" and "neoplasm(s);" the term "cancer cell(s)" is interchangeable with the terms "tumor cell(s)," "malignant cell(s)," "hyperproliferative cell(s)," and "neoplastic cell(s)".

"Melanoma" refers to a malignant neoplasm originating from cells that are capable of producing melanin. The term melanoma is synonymous with "malignant melanoma". Melanoma metastasizes widely, involving a patient's lymph nodes, skin, liver, lungs and brain tissues.

"Solid tumor" refers to all neoplastic cell growth and proliferation, and all pre-cancerous and cancerous cells and tissues, except for hematologic cancers such as lymphomas, leukemias and multiple myeloma. Examples of solid tumors include, but are not limited to: soft tissue sarcoma, such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor and other bone tumors (e.g., osteosarcoma, malignant fibrous histiocytoma), leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, brain/CNS tumors (e.g., astrocytoma, glioma, glioblastoma, childhood tumors, such as atypical teratoid/rhabdoid tumor, germ cell tumor, embryonal tumor, ependymoma) medulloblastoma, craniopharyngioma, ependymoma, pinealoma, hemangioblastoma, acoustic neuroma, oligodendroglioma, meningioma, melanoma, neuroblastoma, and retinoblastoma. Some of the most common solid tumors for which the compositions and methods of the present disclosure would be useful include: head-and-neck cancer, rectal adenocarcinoma, glioma, medulloblastoma, urothelial carcinoma, pancreatic adenocarcinoma, uterine (e.g., endometrial cancer, fallopian tube cancer,) ovarian cancer, cervical cancer prostate adenocarcinoma, non-small cell lung cancer (squamous and adenocarcinoma), small cell lung cancer, melanoma, breast carcinoma, ductal carcinoma in situ, renal cell carcinoma, and hepatocellular carcinoma. adrenal tumors (e.g., adrenocortical carcinoma), esophageal, eye (e.g., melanoma, retinoblastoma), gallbladder, gastrointestinal, Wilms' tumor, heart, head and neck, laryngeal and hypopharyngeal, oral (e.g., lip, mouth, salivary gland), nasopharyngeal, neuroblastoma, peritoneal, pituitary, Kaposi's sarcoma, small intestine, stomach, testicular, thymus, thyroid, parathyroid, vaginal tumor and the metastases of any of the foregoing.

"Metastasis" refers to the spread of cancer from its primary site to neighboring tissues or distal locations in the body. Cancer cells can break away from a primary tumor, penetrate into lymphatic and blood vessels, circulate through the bloodstream, and grow in in normal tissues elsewhere in the body. Metastasis is a sequential process, contingent on tumor cells (or cancer stem cells) breaking off from the primary tumor, traveling through the bloodstream or lymphatics, and stopping at a distant site. Once at another site, cancer cells re-penetrate through the blood vessels or lymphatic walls, continue to multiply, and eventually form a new tumor (metastatic tumor). In some embodiments, this new tumor is referred to as a metastatic (or secondary) tumor.

"Immune response" refers to the action of one or more of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, etc. An immune response may include a cellular response, such as a T cell response that is an alteration (modulation, e.g., significant enhancement, stimulation, activation, impairment, or inhibition) of cellular function that is a T cell function. A T cell response may include generation, proliferation or expansion, or stimulation of a particular type of T cell, or subset of T cells, for example, effector CD4+, CD4$^+$ helper, effector CD8+, CD8$^+$ cytotoxic, or natural killer (NK) cells. Such T cell subsets may be identified by detecting one or more cell receptors or cell surface molecules (e.g., CD or cluster of differentiation molecules). A T cell response may also include altered expression (statistically significant increase or decrease) of a cellular factor, such as a soluble mediator (e.g., a cytokine, lymphokine, cytokine binding protein, or interleukin) that influences the differentiation or proliferation of other cells. For example, Type I interferon (IFN-α/β) is a critical regulator of the innate immunity (52) (Huber et al. *Immunology* 132 (4):466-474 (2011)). Animal and human studies have shown a role for IFN-α/β in directly influencing the fate of both CD4$^+$ and CD8$^+$ T cells during the initial phases of antigen recognition anti-tumor immune response. IFN Type I is induced in response to activation of dendritic cells, in turn a sentinel of the innate immune system.

"Tumor immunity" refers to one or more processes by which tumors evade recognition and clearance by the immune system. Thus, as a therapeutic concept, tumor immunity is "treated" when such evasion is attenuated or eliminated, and the tumors are recognized and attacked by the immune system (the latter being termed herein "anti-tumor immunity"). An example of tumor recognition is tumor binding, and examples of tumor attack are tumor reduction (in number, size or both) and tumor clearance.

"T cell" refers to a thymus derived lymphocyte that participates in a variety of cell-mediated adaptive immune reactions.

"Helper T cell" refers to a CD4$^+$ T cell; helper T cells recognize antigen bound to MHC Class II molecules. There are at least two types of helper T cells, Th1 and Th2, which produce different cytokines.

"Cytotoxic T cell" refers to a T cell that usually bears CD8 molecular markers on its surface (CD8+) and that functions in cell-mediated immunity by destroying a target cell having a specific antigenic molecule on its surface. Cytotoxic T cells also release Granzyme, a serine protease that can enter target cells via the perforin-formed pore and induce apoptosis (cell death). Granzyme serves as a marker of cytotoxic phenotype. Other names for cytotoxic T cell include CTL, cytolytic T cell, cytolytic T lymphocyte, killer T cell, or killer T lymphocyte. Targets of cytotoxic T cells may include virus-infected cells, cells infected with bacterial or protozoal parasites, or cancer cells. Most cytotoxic T cells have the protein CD8 present on their cell surfaces. CD8 is attracted to portions of the Class I MHC molecule. Typically, a cytotoxic T cell is a CD8+ cell.

"Tumor-infiltrating leukocytes" refers to white blood cells of a subject afflicted with a cancer (such as melanoma), that are resident in or otherwise have left the circulation (blood or lymphatic fluid) and have migrated into a tumor.

"Immune checkpoint inhibitor" or "immune checkpoint blocking agent" refers to molecules that completely or partially reduce, inhibit, interfere with or modulate the activity of one or more checkpoint proteins. Checkpoint proteins regulate T-cell activation or function. Checkpoint proteins include, but are not limited to CD28 receptor family members, CTLA-4 and its ligands CD80 and CD86; PD-1 and its ligands PDL1 and PDL2; LAG3, B7-H3, B7-H4, TIM3, ICOS, and BTLA (53).

"Parenteral" when used in the context of administration of a therapeutic substance includes any route of administration other than administration through the alimentary tract. Particularly relevant for the methods disclosed herein are intravenous (including for example through the hepatic portal vein), intratumoral or intrathecal administration.

"Antibody" refers to an immunoglobulin molecule which specifically binds to an antigen or to an antigen-binding fragment of such a molecule. Thus, antibodies can be intact immunoglobulins derived from natural sources or from recombinant sources and can be immunoreactive (antigen-binding) fragments or portions of intact immunoglobulins. The antibodies may exist in a variety of forms including, for example, polyclonal antibodies, monoclonal antibodies, Fv, Fab and F(ab)2, as well as single chain antibodies (scFv) humanized antibodies, chimeric antibodies, human recombinant antibodies and bi- and tri-specific antibodies.

"Oncolytic virus" refers to a virus that preferentially infects cancer cells, replicates in such cells, and induces lysis of the cancer cells through its replication process. Nonlimiting examples of naturally occurring oncolytic viruses include vesicular stomatitis virus, reovirus, as well as viruses engineered to be oncoselective such as adenovirus, Newcastle disease virus and herpes simplex virus (See, e.g., Nemunaitis, J. *Invest New Drugs.* 17 (4):375-86 (1999); Kim, D H et al. *Nat Rev Cancer.* 9 (1):64-71 (2009); Kim et al. *Nat. Med.* 7:781 (2001); Coffey et al. *Science* 282:1332 (1998)) (8, 54-56). Vaccinia virus infects many types of cells but replicates preferentially in tumor cells due to the fact that tumor cells have a metabolism that favors replication, exhibit activation of certain pathways that also favor replication and create an environment that evades the innate immune system, which also favors viral replication. In the context of the present disclosure, MVA and MVAΔE3L do not fit the definition of oncolytic viruses as they do not produce an antitumor effect primarily by replicating inside tumor cells and causing apoptosis. (Nor do they fit the classic definition of vaccines as these viruses do not express tumor antigens. It can be said however, that they act as immunostimulatory molecules, akin to adjuvants, as they serve to enhance the host's immune response against the tumor.)

"MVA" means "modified vaccinia Ankara" and refers to a highly attenuated strain of vaccinia derived from the Ankara strain and developed for use as a vaccine and vaccine adjuvant. The original MVA was isolated from the wild-type Ankara strain by successive passage through chicken embryonic cells, Treated thus, it lost about 15% of the genome of wild-type vaccinia including its ability to replicate efficiently in primate (including human) cells. (57) (Mayr et al., *Zentralbl Bakteriol B* 167, 375-390 (1978)). The smallpox vaccination strain MVA: marker, genetic structure, experience gained with the parenteral vaccination and behavior in organisms with a debilitated defense mechanism. MVA is considered an appropriate candidate for development as a recombinant vector for gene or vaccination delivery against infectious diseases or tumors. (58) (Verheust et al., *Vaccine* 30 (16), 2623-2632 (2012)). MVA has a genome of 178 kb in length and a sequence first disclosed in (59) (Antoine et al., *Virol.* 244 (2): 365-396 (1998)). Sequences are also disclosed in Genbank U94848.1. Clinical grade MVA is commercially and publicly available from Bavarian Nordic A/S Kvistgaard, Denmark. Additionally, MVA is available from ATCC, Rockville, MD and from CMCN (Institut Pasteur Collection Nationale des Microorganismes) Paris, France.

"MVAΔE3L" means a deletion mutant of MVA which lacks a functional E3L gene and is infective but non replicative and it is further impaired in its ability to evade the host's immune system. It can be used as a vaccine vector. This mutant MVA E3L knockout and its preparation have been described for example in U.S. Pat. No. 7,049,145.

"Subject" means any animal (mammalian, human or other) patient that can be afflicted with cancer and when thus afflicted is in need of treatment.

"Therapeutically effective amount" or "effective amount" refers to a sufficient amount of an agent when administered at one or more dosages and for a period of time sufficient to provide a desired biological result in alleviating, curing or palliating a disease. In the present disclosure, an effective amount respectively of the MVA or MVAΔE3L is an amount that (administered for a suitable period of time and at a suitable frequency) reduces the number of cancer cells; or reduces the tumor size or eradicates the tumor; or inhibits (i.e., slows down or stops) cancer cell infiltration into peripheral organs; inhibits (i.e., slows down or stops) metastatic growth; inhibits (stabilizes or arrests) tumor growth; allows for treatment of the tumor, and/or induces an immune response against the tumor. An appropriate therapeutic amount in any individual case may be determined by one of ordinary skill in the art using routine experimentation in light of the present disclosure. Such determination will begin with amounts found effective in vitro and amounts found effective in animals. The therapeutically effective amount will be initially determined based on the concentration or concentrations found to confer a benefit to cells in culture. Effective amounts can be extrapolated from data within the cell culture and can be adjusted up or down based on factors such as detailed herein. An example of an effective amount range is from $10^5$ viral particles to about $10^{12}$ viral particles per administration.

With particular reference to the viral-based immunostimulatory agents disclosed herein, "therapeutically effective amount" or "effective amount" refers to an amount of a composition comprising MVA or MVAΔE3L sufficient to reduce, inhibit, or abrogate tumor cell growth, thereby reducing or eliminating the tumor, or sufficient to inhibit, reduce or abrogate metastatic spread either in vitro, ex vivo or in a subject or to elicit an immune response against the tumor that will eventually result in one or more of metastatic spread reduction, inhibition and/or abrogation as the case may be. The reduction, inhibition, or eradication of tumor cell growth may be the result of necrosis, apoptosis, or an immune response or a combination of two or more of the foregoing (however, the precipitation of apoptosis for example may not be due to the same factors as observed with oncolytic viruses). The amount that is therapeutically effective may vary depending on such factors as the particular MVA used in the composition, the age and condition of the subject being treated, the extent of tumor formation, the presence or absence of other therapeutic modalities, and the like. Similarly, the dosage of the composition to be administered and the frequency of its administration will depend on a variety of factors, such as the potency of the active ingredient, the duration of its activity once administered, the route of administration, the size, age, sex and physical condition of the subject, the risk of adverse reactions and the judgment of the medical practitioner. The compositions are administered in a variety of dosage forms, such as injectable solutions.

With particular reference to combination therapy with an immune checkpoint inhibitor, "therapeutically effective amount" for an immune checkpoint blocking agent" shall mean an amount of an immune checkpoint blocking agent sufficient to reverse or reduce immune suppression in the tumor microenvironment and to activate or enhance host immunity in the subject being treated. There are several immune checkpoint blocking agents approved, in clinical trials or still otherwise under development including inhibitory antibodies against CD28 inhibitor such as CTLA-4 (cytotoxic T lymphocyte antigen 4) (e.g., ipilimumab), anti-PD-1 (programmed Death 1) inhibitory antibodies (e.g., nivolumab, pembrolizumab, pidilizumab, lambrolizumab), and anti-PD-L1 (Programmed death ligand 1) inhibitory antibodies (MPDL3280A, BMS-936559, MEDI4736, MSB 00107180), as well as inhibitory antibodies against LAG-3 (lymphocyte activation gene 3), TIM3 (T cell Immunoglobulin and Mucin-3), B7-H3, and TIGIT (T-cell immunoreceptor with Ig and ITIM domains). Dosage ranges of the foregoing are known in or readily within the skill in the art as several dosing clinical trials have been completed, making extrapolation to other agents possible.

Preferably, the tumor expresses the particular checkpoint but this is not strictly necessary as immune checkpoint blocking agents block more generally immune suppressive mechanisms within the tumors, elicited by tumor cells, stromal cells, and tumor-infiltrating immune cells.

For example, the CTLA4 inhibitor ipilimumab, when administered as adjuvant therapy after surgery in melanoma is administered at 1-2 mg/mL over 90 minutes for a total infusion amount of 3 mg/kg every three weeks for a total of 4 doses. This therapy is often accompanied by severe even life-threatening immune-mediated adverse reactions, which limits the tolerated dose as well as the cumulative amount that can be administered. It is anticipated that it will be possible to reduce the dose and/or cumulative amount of ipilimumab when it is administered conjointly with MVA or MVAΔE3L. In particular, in light of the experimental results set forth below, it is anticipated that it will be further possible to reduce the CTLA4 inhibitor's dose if it is administered directly to the tumor simultaneously or sequentially with one or both the foregoing MVA viruses. Accordingly, the amounts provided above for ipilimumab will be a starting point for determining the particular dosage and cumulative amount to be given to a patient in conjoint administration but dosing studies will be required to determine optimum amounts.

Pembrolizumab is prescribed for administration as adjuvant therapy in melanoma diluted to 25 mg/mL. It is administered at a dosage of 2 mg/kg over 30 minutes every three weeks. Again, this would be a starting point for determining dosage and administration in the conjoint administration with MVA or MVAΔE3L.

Nivolumab is prescribed for administration at 3 mg/kg as an intravenous infusion over 60 minutes every two weeks, providing a similar starting point in determining dosage and administration of this checkpoint inhibitor conjointly with MVA or MVAΔE3L.

Immune stimulating agents such as agonist antibodies have also been explored as immunotherapy for cancers. For example, anti-ICOS antibody binds to the extracellular domain of ICOS leading to the activation of ICOS signaling and T cell activation. Anti-OX40 antibody can bind to OX40 and potentiate T cell receptor signaling leading to T cell activation, proliferation and survival. Other examples include agonist antibodies against 4-1BB (CD137), GITR. All of these agents are at various stages of clinical trials.

The immune stimulating agonist antibodies can be used systemically in combination with intratumoral injection of MVA or MVAΔE3L. Alternatively, the immune stimulating agonist antibodies can be used conjointly with MVA or MVAΔE3L via intratumorally delivery either simultaneously or sequentially.

"Pharmaceutically acceptable carrier and/or diluent" or "pharmaceutically acceptable excipient" includes without limitation any and all solvents, dispersion media, coatings, antibacterial and antifungal agents, isotonic and absorption delaying agents and the like. The use of such media and agents for biologically active substances is well known in the art. Further details of excipients are provided below. Supplementary active ingredients, such as antimicrobials, for example antifungal agents, can also be incorporated into the compositions.

"Delivering" used in connection with depositing the MVA or MVAΔE3L of the present disclosure in the tumor microenvironment whether this is done by local administration to the tumor or by for example intravenous route. The term focuses on MVA or MVAΔE3L that reaches the tumor itself "Conjoint administration" herein refers to administration of a second therapeutic modality in combination with MVA or MVAΔE3L for example an immune checkpoint blocking agent administered and in close temporal proximity with MVA or MVAΔE3L. For example, a PD-1/PDL-1 inhibitor and/or a CTLA4 inhibitor (in more specific embodiments, an antibody) can be administered simultaneously with MVA or MVAΔE3L (by intravenous or intratumoral injection when the MVA or MVAΔE3L is administered intratumorally or systemically as stated above) or before or after the MVA or MVAΔE3L administration. If the MVA or MVAΔE3L administration and the immune checkpoint blocking agent are administered 1-7 days apart or even up to three weeks apart, this would be within "close temporal proximity" as stated herein.

In one embodiment, the present disclosure relates to a method for eliciting an antitumor immune response in subjects afflicted with tumors comprising delivering to the tumor an effective amount of MVA or MVAΔE3L. Stimulation of the immune system may be manifest by one or more of the following immunological effects:

an increase in at least one of effector $CD8^+$ T cells and effector CD4+ T cells within the tumor and/or in tumor-draining lymph nodes;

induction of maturation of dendritic cells infiltrating said tumor through induction of type I IFN;

induction of effector $CD4^+$ T cells in the subject recognizing tumor cells within the tumor and/or in tumor draining lymph nodes;

reduction of immune suppressive (regulatory) $CD4^+$ T cells within the tumor;

induction of cells of the tumor to produce one or more of Type I IFN or other inflammatory cytokines or chemokines;

reduction of immune suppressive tumor-associated macrophages within the tumor.

The foregoing one or more immunological effects may serve as early indicators of response of the subject to the treatment and may serve as monitors of the continued effectiveness of same. Observation of these effects illustrates that the manner in which the present viruses treat tumor is different from that of vaccine vectors harboring tumor antigens (which are not delivered intratumorally but by intramuscular, subcutaneous or, rarely, intravenous route) and also different from that of oncolytic viruses (which cause cytopathy primarily due to viral replication in tumor cells). If apoptosis results pursuant to the present treatment, it is not due to the same mechanism as apoptosis that results or may result from these different modes of action.

The present inventors have explored the mechanism of the immune response and concluded that it is initiated by the cytosolic DNA-sensing pathway mediated by cGAS/STING which mediates production of Type 1 IFN. Further insights into the mechanism and the immune cells that are recruited are provided in the Examples. The conclusions presented therein are not confined to the specific experimental milieu where these mechanisms are being elucidated.

In one embodiment, the present disclosure provides a method of treating a subject diagnosed with a solid tumor comprising delivering to the tumor a therapeutic effective amount of the MVA or MVAΔE3L.

In one embodiment, the present disclosure provides a method for inducing anti-tumor immunity in a subject diagnosed with cancer comprising administering to the subject a therapeutically effective amount of MVA or MVAΔE3L. The methods of the present disclosure include induction of anti-tumor immunity that can reduce the size of the tumor, eradicate the tumor, inhibit growth of the tumor, inhibit metastasis or reduce metastatic growth of the tumor or eradicate metastatic growth of the tumor, induce apoptosis of tumor cells or prolong survival of the subject (compared to untreated or conventionally treated subjects).

In another embodiment, the present disclosure provides a method for enhancing, stimulating, or eliciting, in a subject diagnosed with a solid malignant tumor, an anti-tumor immune response that may include an innate immune response and/or an adaptive immune response such as a T cell response by exposing the tumor to MVA or MVAΔE3L in a therapeutically effective amount.

In specific embodiments, the present disclosure provides methods of eliciting an immune response that mediates adaptive immune responses both in terms of T-cell cytotoxicity directed against tumor cells and in terms of eliciting effector T cells also directed against tumor cells. The methods comprise administering to a subject afflicted with a solid tumor intratumorally or (as the present inventors anticipate) intravenously a composition comprising MVA or MVAΔE3L wherein administration of said composition results in a tumor-specific immune response against the tumor and, eventually, in reduction, inhibition or eradication of tumor growth, inhibition of metastatic growth, apoptosis of tumor cells and/or prolongation of the subject's survival. Indeed the present inventors have shown that cancer cells are being killed and that the immune response can migrate to remote locations, as would be the case with metastases.

In some embodiments, the present disclosure provides methods of eliciting an immune response that mediates adaptive immune responses both in terms of T-cell cytotoxicity directed against tumor cells and in terms of eliciting effector T cells also directed against tumor cells. The methods comprise administering to a subject parenterally a composition comprising MVA or MVAΔE3L wherein administration of said composition results in a tumor-specific immune response against the tumor and, eventually, in reduction, inhibition or eradication of tumor growth and/or in inhibition reduction or elimination of metastatic growth, apoptosis of tumor cells and/or prolongation of survival of the treated subject compared to conventional therapy or no treatment. For intraperitoneal metastases, the virus can be injected intraperitoneally.

Indeed the present inventors have shown that cancer cells are being killed and that the immune response can migrate to remote locations, as would be the case with metastases, and still exert an anti-tumor effect.

Because MVA and MVAΔE3L are substantially not replication competent in most mammalian cells, it does not exert its effect on the immune system the same way as replication competent vaccines or vectors. Thus, while it is believed that stimulation of the immune system is a barrier to efficacy for oncolysis (8) (Kirn et al., *Nat Rev Cancer*. (1), 64-71 (2009)), MVA and MVAΔE3L is able to harness the innate immune system to stimulate adaptive immunity, both in terms of cytotoxicity and more broadly in terms of effector T cell activation against the tumor.

The present disclosure thus provides a method for treating a solid malignant tumor, comprising delivering to a tumor of the subject an amount of MVA or MVAΔE3L effective to induce an immune response against the tumor in a subject diagnosed with solid tumor.

The present disclosure also provides a method for generating antitumor systemic immunity in a subject afflicted with a solid malignant tumor, comprising delivering to a tumor of the subject an amount of MVA or MVAΔE3L effective to bring about one or both of rejection of non-injected tumors in said subject and inhibition of tumor metastasis (which the present inventors test by tumor rechallenge).

As is shown herein, MVA induces type I IFN induction in conventional dendritic cells (cDCs) via a cytosolic DNA-sensing pathway mediated by cGAS/STING. Intravenous delivery of MVA in C57B/6 mice induced type I IFN in wild-type mice, but not in mice lacking STING or IRF3. It is also shown that MVAΔE3L induces higher levels of type I IFN gene expression and phosphorylation of IRF3 than MVA in cDCs. MVAΔE3L is detected by both the cytosolic DNA-sensing pathway mediated by cGAS/STING, and the dsRNA-sensing pathway mediated by MDA5/MAVS. In addition, MVAΔE3L infection of B16 melanoma cells and MC38 colon adenocarcinoma cells induces type I IFN and proinflammatory cytokines and chemokines, as well as activation of phosphorylation of IRF3. Both MVA and MVAΔE3L induce apoptosis in B16 and MC38 cells as demonstrated by the cleavage of PARP and Caspase-3. According to the present disclosure MVA or MVAΔE3L virus is used as direct anti-cancer therapy. Intratumoral injection of MVA or MVAΔE3L in a murine B16 melanoma model leads to apoptosis, prolonged survival and tumor eradication, as well as the generation of systemic anti-tumor immunity.

Based on current literature, and without wishing to be bound by theory, the following mechanisms are believed to contribute to anti-tumor effects of MVA and MVAΔE3L: (i) induction of type I IFN responses in immune cells including conventional dendritic cells and macrophages; (ii) induction of type I IFN and proinflammatory cytokines and chemokines in cancer cells; (iii) induction of apoptosis in cancer cells; and (iv) alteration of tumor immune suppressive environment to an immune activating one.

Modified Vaccinia Ankara (MVA)

Modified Vaccinia Ankara (MVA) virus is a member of the genera Orthopoxvirus in the family of Poxviridae. MVA was generated by approximately 570 serial passages on chicken embryo fibroblasts (CEF) of the Ankara strain of vaccinia virus (CVA) (60) (Mayr et al., *Infection* 3, 6-14 (1975)). As a consequence of these long-term passages, the resulting MVA virus contains extensive genome deletions and is highly host cell restricted to avian cells (61) (Meyer et al., *J. Gen. Virol.* 72, 1031-1038 (1991)). It was shown in a variety of animal models that the resulting MVA is significantly avirulent (57) (Mayr et al., *Dev. Biol. Stand.* 41, 225-34 (1978)).

The safety and immunogenicity of MVA has been extensively tested and documented in clinical trials, particularly against the human smallpox disease. These studies included over 120,000 individuals and have demonstrated excellent efficacy and safety in humans. Moreover, compared to other vaccinia based vaccines, MVA has weakened virulence (infectiousness) while it triggers a good specific immune response. Thus, MVA has been established as a safe vaccine vector, with the ability to induce a specific immune response.

Due to the above mentioned characteristics, MVA became an attractive candidate for the development of engineered MVA vectors, used for recombinant gene expression and vaccines. As a vaccine vector, MVA has been investigated against numerous pathological conditions, including HIV, tuberculosis and malaria, as well as cancer (20, 21) (Sutter et al., *Curr Drug Targets Infect Disord* 3: 263-271 (2003); Gomez et al., *Curr Gene Ther* 8: 97-120 (2008)).

It has been demonstrated that MVA infection of human monocyte-derived dendritic cells (DC) causes DC activation, characterized by the upregulation of co-stimulatory molecules and secretion of proinflammatory cytokines (18) (Drillien et al., *J Gen Virol* 85: 2167-2175 (2004)). In this respect, MVA differs from standard wild type Vaccinia virus (WT-VAC), which fails to activate DCs. Dendritic cells can be classified into two main subtypes: conventional dendritic cells (cDCs) and plasmacytoid dendritic cells (pDCs). The former, especially the CD103+/CD8$\alpha^+$ subtype, are particularly adapted to cross-presenting antigens to T cells; the latter are strong producers of Type I IFN.

Viral infection of human cells results in activation of an innate immune response (the first line of defense) mediated by type I interferons, notably interferon-alpha ($\alpha$). This normally leads to activation of an immunological "cascade," with recruitment and proliferation of activated T cells (both CTL and helper) and eventually with antibody production. However viruses express factors that dampen immune responses of the host. MVA is a better immunogen than WT-VAC and replicates poorly in mammalian cells. (See, e.g., Brandler et al., *J. Virol.* 84, 5314-5328 (2010)) (62).

However, MVA is not entirely nonreplicative and as the present inventors show contains some residual immunosuppressive activity. Nevertheless, as shown herein MVA significantly prolonged survival of treated subjects. An implication of these findings is that by injecting a tumor with or systemically delivering MVA (or MVA$\Delta$E3L) it is possible to enhance a host's innate and adaptive immune responses and thereby overcome the tumor's ability to evade immune responses and to restore the ability of the host to mount an immune response against the tumor whether the response is native or induced or enhanced by another immunotherapeutic agent, such as a checkpoint inhibitor.

Modified Vaccinia Ankara with Deletion of E3 (MVA$\Delta$E3L)

The antitumor effects of MVA described in the immediately preceding section are also observed with MVA$\Delta$E3L. The latter is less immunosuppressive than MVA and even less replicative in most mammalian cells, and from that point of view preferred. In addition, the effects of MVA$\Delta$E3L have generally been qualitatively better than those with MVA as seen in the experiments described herein.

Immune Response

In addition to induction of the immune response by up-regulation of particular immune system activities (such as antibody and/or cytokine production, or activation of cell mediated immunity), immune responses may also include suppression, attenuation, or any other down-regulation of detectable immunity, so as to reestablish homeostasis and prevent excessive damage to the host's own organs and tissues. In some embodiments, an immune response that is induced according to the methods of the present disclosure generates effector CD8$^+$ (antitumor cytotoxic CD8$^+$) T cells or activated T helper cells or both that can bring about directly or indirectly the death, or loss of the ability to propagate, of a tumor cell.

Induction of an immune response by the methods of the present disclosure may be determined by detecting any of a variety of well-known immunological parameters (63, 64) (Takaoka et al., *Cancer Sci.* 94:405-11 (2003); Nagorsen et al., *Crit. Rev. Immunol.* 22:449-62 (2002)). Induction of an immune response may therefore be established by any of a number of well-known assays, including immunological assays, Such assays include, but need not be limited to, in vivo, ex vivo, or in vitro determination of soluble immunoglobulins or antibodies; soluble mediators such as cytokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, altered intracellular cation gradient or concentration (such as calcium); phosphorylation or dephosphorylation of cellular polypeptides; induction of specialized activities such as specific gene expression or cytolytic behavior; cellular differentiation by cells of the immune system, including altered surface antigen expression profiles, or the onset of apoptosis (programmed cell death); or any other criterion by which the presence of an immune response may be detected. For example, cell surface markers that distinguish immune cell types may be detected by specific antibodies that bind to CD4+, CD8+, or NK cells. Other markers and cellular components that can be detected include but are not limited to interferon $\gamma$ (IFN-$\gamma$), tumor necrosis factor (TNF), IFN-$\alpha$, IFN-$\beta$, IL-6, and CCL5. Common methods for detecting the immune response include, but are not limited to flow cytometry, ELISA, immunohistochemistry. Procedures for performing these and similar assays are widely known and may be found, for example in Letkovits (Immunology Methods Manual: The Comprehensive Sourcebook of Techniques, Current Protocols in Immunology, 1998).

Pharmaceutical Compositions and Preparations

Pharmaceutical compositions comprising MVA or MVA$\Delta$E3L may contain a carrier or diluent, which can be a solvent or dispersion medium containing, for example, water, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be effected by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin. In general, excipients suitable for injectable preparations can be included as apparent to those skilled in the art.

Pharmaceutical compositions and preparations comprising MVA or MVA$\Delta$E3L may be manufactured by means of conventional mixing, dissolving, granulating, emulsifying, encapsulating, entrapping or lyophilizing processes. Pharmaceutical viral compositions may be formulated in conventional manner using one or more physiologically acceptable carriers, diluents, excipients or auxiliaries that facilitate formulating virus preparations suitable for in vitro, in vivo, or ex vivo use. The compositions can be combined with one or more additional biologically active agents (for example parallel administration of GM-CSF) and may be formulated with a pharmaceutically acceptable carrier, diluent or excipient to generate pharmaceutical (including biologic) or veterinary compositions of the instant disclosure suitable for parenteral or intra-tumoral administration.

Many types of formulation are possible as is appreciated by those skilled in the art. The particular type chosen is dependent upon the route of administration chosen, as is well-recognized in the art. For example, systemic formulations will generally be designed for administration by injection, e.g., intravenous, as well as those designed for intratumoral delivery. Preferably, the systemic or intratumoral formulation is sterile.

Sterile injectable solutions are prepared by incorporating MVA or MVAΔE3L in the required amount of the appropriate solvent with various other ingredients enumerated herein, as required, followed by suitable sterilization means. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the preferred methods of preparation are vacuum drying and freeze-drying techniques, which yield a powder of the virus plus any additional desired ingredient from a previously sterile-filtered solution thereof.

In some embodiments, the MVA and MVAΔE3L compositions of the present disclosure may be formulated in aqueous solutions, or in physiologically compatible solutions or buffers such as Hanks's solution, Ringer's solution, mannitol solutions or physiological saline buffer. In certain embodiments, any of the MVA and MVAΔE3L compositions may contain formulator agents, such as suspending, stabilizing, penetrating or dispersing agents, buffers, lyoprotectants or preservatives such as polyethylene glycol, polysorbate 80, 1-dodecylhexahydro-2H-azepin-2-one (laurocapran), oleic acid, sodium citrate, Tris HCl, dextrose, propylene glycol, mannitol, polysorbate polyethylenesorbitan monolaurate (Tween®-20), isopropyl myristate, benzyl alcohol, isopropyl alcohol, ethanol sucrose, trehalose and other such generally known in the art may be used in any of the compositions of the instant disclosure. (Pramanick et al., *Pharma Times* 45 (3), 65-76 (2013))(65).

The biologic or pharmaceutical compositions of the present disclosure can be formulated to allow the virus contained therein to be available to infect tumor cells upon administration of the composition to a subject. The level of virus in serum, tumors, and if desired other tissues after administration can be monitored by various well-established techniques, such as antibody-based assays (e.g., ELISA, immunohistochemistry, etc.).

Dosage of MVA and MVAΔE3L

In general, the subject is administered a dosage of MVA and MVAΔE3L in the range of about $10^5$ to about $10^{10}$ plaque forming units (pfu), although a lower or higher dose may be administered. In a preferred embodiment, dosage is about $10^6$-$10^9$ pfu. The equivalence of pfu to virus particles can differ according to the specific pfu titration method used. Generally, pfu is equal to about 5 to 100 virus particles. A therapeutically effective amount of MVA or MVAΔE3L can be administered in one or more divided doses for a prescribed period of time and at a prescribed frequency of administration.

For example, as is apparent to those skilled in the art, a therapeutically effective amount of MVA or MVAΔE3L in accordance with the present disclosure may vary according to factors such as the disease state, age, sex, weight, and general condition of the subject, and the ability of MVA or MVAΔE3L to elicit a desired immunological response in the particular subject (the subject's response to therapy). In delivering MVA or MVAΔE3L to a subject, the dosage will also vary depending upon such factors as the general medical condition, previous medical history, disease progression, tumor burden and the like.

In some embodiments, it may be advantageous to formulate compositions of present disclosure in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutically or veterinary acceptable carrier.

Administration and Therapeutic Regimen of MVA and MVAΔE3L

Administration of MVA and MVAΔE3L can be achieved using more than one route, including parenteral, for example intratumoral or intravenous, administration. In one embodiment, MVA or MVAΔE3L is administered directly into the tumor, e.g. by intratumoral injection, where a direct local reaction is desired. Additionally, administration routes of MVA and MVAΔE3L can vary, e.g., first administration using an intratumoral injection, and subsequent administration via an intravenous injection, or any combination thereof. A therapeutically effective amount of MVA or MVAΔE3L injection can be administered for a prescribed period of time and at a prescribed frequency of administration. In certain embodiments, MVA and MVAΔE3L can be used in conjunction with other therapeutic treatments. For example, MVA and MVAΔE3L can be administered in a neoadjuvant (preoperative) or adjuvant (postoperative) setting for subjects inflicted with bulky primary tumors. It is anticipated that such optimized therapeutic regimen will induce an immune response against the tumor, and reduce the tumor burden in a subject before or after primary therapy, such as surgery. Furthermore, MVA or MVAΔE3L can be administered in conjunction with other therapeutic treatments such as chemotherapy or radiation.

In certain embodiments, the MVA or MVAΔE3L virus is administered at least once weekly or monthly but can be administered more often if needed, such as two times weekly for several weeks, months, years or even indefinitely as long as benefits persist. More frequent administrations are contemplated if tolerated and if they result in sustained or increased benefits. Benefits of the present methods include but are not limited to the following: reduction of the number of cancer cells, reduction of the tumor size, eradication of tumor, inhibition of cancer cell infiltration into peripheral organs, inhibition or stabilization or eradication of metastatic growth, inhibition or stabilization of tumor growth, and stabilization or improvement of quality of life. Furthermore, the benefits may include induction of an immune response against the tumor, activation of effector $CD4^+$ T cells, an increase of effector $CD8^+$ T cells, or reduction of regulatory $CD4^+$ cells. For example, in the context of melanoma or, a benefit may be a lack of recurrences or metastasis within one, two, three, four, five or more years of the initial diagnosis of melanoma. Similar assessments can be made for colon cancer and other solid tumors.

In certain other embodiments, the tumor mass or tumor cells are treated with MVA or MVAΔE3L in vivo, ex vivo, or in vitro.

EXAMPLES

Materials and Methods

Viruses and Cell Lines

MVA and MVAΔE3L viruses were kindly provided by Gerd Sutter (University of Munich), and propagated in BHK-21 (baby hamster kidney cell, ATCC CCL-10) cells. MVA is commercially and/or publicly available. The method of generation of MVAΔE3L Viruses was described (28) (Hornemann et al., *J Virol* 77, 8394-8407 (2003)). The viruses were purified through a 36% sucrose cushion. BHK-21 were cultured in Eagle's Minimal Essential Medium (Eagle's MEM, can be purchased from Life Technologies, Cat #11095-080) containing 10% FBS, 0.1 mM nonessential amino acids (NEAA), and 50 mg/ml gentamycin. The murine melanoma cell line B16-F10 was originally obtained from I. Fidler (MD Anderson Cancer Center). B16-F10 cells were maintained in RPMI 1640 medium supplemented with 10% FBS, 100 Units/ml penicillin, 100 µg/ml streptomycin, 0.1 mM NEAA, 2 mM L-glutamine, 1 mM sodium pyruvate, and 10 mM HEPES buffer. The MC38 colon adenocarcinoma cancer cells were maintained in Dulbecco's modified Eagle medium (DMEM, Invitrogen). All cells were grown at 3TC in a 5% $CO_2$ incubator.

Cells and cell lines used herein are commercially or publicly available unless otherwise indicated.

Mice

Female C57BL/6J mice between 6 and 10 weeks of age were purchased from the Jackson Laboratory and were used for the preparation of bone marrow-derived dendritic cells and as control mice for in vivo experiments. These mice were maintained in the animal facility at the Sloan Kettering Institute. All procedures were performed in strict accordance with the recommendations in the Guide for the Care and Use of Laboratory Animals of the National Institute of Health. The protocol was approved by the Committee on the Ethics of Animal Experiments of Sloan-Kettering Cancer Institute. $cGAS^{-/-}$, $IRF3^{-/-}$, $IRF7^{-/-}$, $MAVS^{-/-}$, $MDA5^{-/-}$, and $STING^{Gt/Gt}$ mice were generated in the laboratories of Drs. Zhijian Chen (University of Texas Southwestern Medical Center; $cGAS^{-/-}$ and $MAVS^{-/-}$), Tadatsugu Taniguchi (University of Tokyo; $IRF3^{-/-}$ and $IRF7^{-/-}$), Marco Colonna (Washington University, $MDA5^{-/-}$), and Russell Vance (University of California, Berkeley; $STING^{Gt/Gt}$).

Commercial sources for these or comparable animals are as follows:

| Mice | Source | Commercial Source |
| --- | --- | --- |
| $cGAS^{-/-}$ | Zhijian Chen | Jackson Stock# 026554 |
| $MAVS^{-/-}$ | Zhijian Chen | Jackson stock# 008634 |
| $MDA5^{-/-}$ | Marco Colonna | Jackson stock# 015812 |
| $STING^{Gt/Gt}$ | Russell Vance | Jackson stock# 017537 |
| $IRF3^{-/-}$ | T. Taniguchi | Taniguchi lab www2.brc.riken.jp/lab/animal/detail.php?reg_no=RBRC00858 |
| $IRF7^{-/-}$ | T. Taniguchi | Taniguchi lab www2.brc.riken.jp/lab/animal/detail.php?brc_no=RBRC01420 |

Generation of Bone Marrow-Derived Dendritic Cells

The bone marrow cells from the tibia and femur of mice were collected by first removing muscles from the bones, and then flushing the cells out using 0.5 cc U-100 insulin syringes (Becton Dickinson) with RPMI with 10% FCS. After centrifugation, cells were re-suspended in ACK Lysing Buffer (Lonza) for red blood cells lysis by incubating the cells on ice for 1-3 min. Cells were then collected, re-suspended in fresh medium, and filtered through a 40-μm cell strainer (BD Biosciences). The number of cells was counted. For the generation of GM-CSF-BMDCs, the bone marrow cells (5 million cells in each 15 cm cell culture dish) were cultured in CM in the presence of GM-CSF (30 ng/ml, produced by the Monoclonal Antibody Core facility at the Sloan Kettering Institute) for 10-12 days. CM is RPMI 1640 medium supplemented with 10% fetal bovine serum (FBS), 100 Units/ml penicillin, 100 μg/ml streptomycin, 0.1 mM essential and nonessential amino acids, 2 mM L-glutamine, 1 mM sodium pyruvate, and 10 mM HEPES buffer. Cells were fed every 2 days by replacing 50% of the old medium with fresh medium and re-plated every 3-4 days to remove adherent cells. Only non-adherent cells were used for experiments.

RNA Isolation and Real-Time PCR

RNA was extracted from whole-cell lystates with an RNeasy Mini kit (Qiagen) and was reverse transcribed with a First Strand cDNA synthesis kit (Fermentas). Quantitative real-time PCR was performed in triplicate with SYBR Green PCR Mater Mix (Life Technologies) and Applied Biosystems 7500 Real-time PCR Instrument (Life Technologies) using gene-specific primers. Relative expression was normalized to the levels of glyceraldehyde-3-phosphate dehydrogenase (GAPDH).

The following primers were used for real-time PCR:

```
IFNA4 forward:
                                       (SEQ ID NO: 1)
5'-CCTGTGTGATGCAGGAACC-3', IFNA4 reverse:
                                       (SEQ ID NO: 2)
5'-TCACCTCCCAGGCACAGA-3';

IFNB forward:
                                       (SEQ ID NO: 3)
5'-TGGAGATGACGGAGAAGATG-3', IFNB reverse:
                                       (SEQ ID NO: 4)
5'-TTGGATGGCAAAGGCAGT-3';

CCL5 forward:
                                       (SEQ ID NO: 5)
5'-GCCCACGTCAAGGAGTATTTCTA-3', CCL5 reverse:
                                       (SEQ ID NO: 6)
5'-ACACACTTGGCGGTTCCTTC-3';

IL-6 forward:
                                       (SEQ ID NO: 7)
5'-AGGCATAACGCACTAGGTTT-3', IL-6 reverse:
                                       (SEQ ID NO: 8)
5'-AGCTGGAGTCACAGAAGGAG-3';

CXCL10 forward:
                                       (SEQ ID NO: 9)
5'ATTCTTTAAGGGCTGGTCTGA 3', CXCL10 reverse:
                                      (SEQ ID NO: 10)
5'CACCTCCACATAGCTTACAGT 3';

TNF forward:
                                      (SEQ ID NO: 11)
5' GTCAGGTTGCCTCTGTCTCA 3', TNF reverse:
                                      (SEQ ID NO: 12)
5'TCAGGGAAGAGTCTGGAAAG 3';

GAPDH forward:
                                      (SEQ ID NO: 13)
5'-ATCAAGAAGGTGGTGAAGCA-3', GAPDH reverse:
                                      (SEQ ID NO: 14)
5'-AGACAACCTGGTCCTCAGTGT-3'.
```

Relative expression was normalized to the levels of glyceraldehyde-3-phosphate dehydrogenase (GADPH).

Cytokine Assays

Cells were infected with various viruses at a MOI of 10 for 1 h or mock infected. The inoculum was removed and the cells were washed with PBS twice and incubated with fresh medium. Supernatants were collected at various times post infection. Cytokine levels were measured by using enzyme-linked immunosorbent assay (ELISA) kits for IFN-α/β (PBL Biomedical Laboratories), IL-6, CCL4, and CCL5 (R & D systems).

Western Blot Analysis

BMDCs, B16-F10, or MC38 cells ($1 \times 10^6$) were infected with MVA at a MOI (multiplicity of infection) of 10 or an equivalent amount of MVA or MVAΔE3L. At various times post-infection, the medium was removed and cells were collected. Whole-cell lysates were prepared. Equal amounts of proteins were subjected to sodium dodecyl sulfate-polyacrylamide gel electrophoresis and the polypeptides were transferred to a nitrocellulose membrane. Phosphorylation of IRF3 was determined using a rabbit polyclonal antibody specific for phosphoserine-396 of IRF3 (Cell Signaling). The level of IRF3 was determined using a rabbit polyclonal antibody against IRF3 (Cell Signaling). Anti-STING antibodies were purchased from Cell Signaling. Vaccinia E3 protein level was determined by using anti-E3 monoclonal antibody (MAb 3015B2) kindly provided by Dr. Stuart N. Isaacs (University of Pennsylvania) (66) (Weaver et al. *Virus Res* 130: 269-274 (2007)). Anti-PARP and anti-MCL-1 antibodies (Cell Signaling) were used to determine PARP cleavage and MCL-1 protein degradation. Anti-glyceraldehyde-3-phosphate dehydrogenase (GADPH) or anti-β-actin antibodies (Cell Signaling) were used as loading controls.

Tumor Implantation and Intratumoral Injection with Viruses

B16-F10 melanoma cells ($1 \times 10^5$) were implanted intradermally into the shaved skin on the right flank C57BL/6J mice. After 10 to 12 days post implantation, tumor sizes were measured and tumors that were 3 mm in diameter or larger were injected with MVA or MVAΔE3L ($2 \times 10^7$ pfu) or PBS when the mice were under anesthesia. Viruses were injected weekly or as specified in each experiment. Mice were monitored daily and tumor sizes were measured twice a week. Tumor volumes were calculated according to the following formula: l (length)×w (width)×h(height)/2. Mice were euthanized for signs of distress or when the diameter of the tumor reached 10 mm. Serum was collected when the mice were euthanized.

MC38 murine colon adenocarcinoma cells ($2 \times 10^5$) were implanted intradermally into the shave skin on the right flank of C57BL/6J mice. After 7 days post implantation, tumor sizes were measured and tumors that are 2-3 mm in diameter were injected with PBS or MVAΔE3L ($2×10^7$ pfu) when the mice were under anesthesia. Tumor sizes were measured at various days post viral injection.

Bilateral Tumor Implantation Model and Intratumoral Injection with MVA or MVAΔE3L Briefly, B16-F10 melanoma cells were implanted intradermally to the left and right flanks of C57B/6 mice ($5×10^5$ to the right flank and $1×10^5$ to the left flank). 8 days after tumor implantation, the larger tumors on the right flank were intratumorally injected with $2×10^7$ pfu of MVA or an equivalent amount of MVAΔE3L. The tumor sizes were measured and the tumors were re-injected twice a week. The survival of mice was monitored.

In some experiments, MC38 colon adenocarcinoma cells were implanted intradermally to the left and right flanks of C57B/6 mice ($5×10^5$ to the right flank and $1×10^5$ to the left flank).

Flow Cytometry

To analyze immune cell phenotypes and characteristics in the tumors or tumor draining lymph nodes, we generated cell suspensions prior to FACS analysis according to the following protocol (46) (Zamarin et al., *Science Translational Medicine* 6, 226-232 (2014)). First we isolated tumors using forceps and surgical scissors three days post treatment with MVA or PBS. The tumors were then weighed. Tumors or tumor draining lymph nodes were minced prior to incubation with Liberase (1.67 Wunsch U/ml) and DNase (0.2 mg/ml) for 30 minutes at 37° C. Cell suspensions were generated by repeated pipetting, filtered through a 70-μm nylon filter, and then washed with complete RPMI prior to Ficoll purification to remove dead cells. Cells were processed for surface labeling with anti-CD3, CD45, CD4, and CD8 antibodies. Live cells are distinguished from dead cells by using fixable dye eFluor506 (eBioscience). They were further permeabilized using FoxP3 fixation and permeabilization kit (eBioscience), and stained for Ki-67, FoxP3, and Granzyme B. For the staining of the myeloid cell population, Fluorochromeconjugated antibodies against CD45.2 (104), CD11b (M1/70), Ly-6C (HK1.4), MHC II (M5/114.15.2), CD24 (M1/69), F4/80 (BM8), CD103 (2E7) and CD11c (N418) were purchased from eBioscience. All antibodies were tested with their respective isotype controls. Data were acquired using the LSRII Flow cytometer (BD Biosciences). Data were analyzed with FlowJo software (Treestar).

Reagents

The commercial sources for reagents were as follows: CpG oligodeoxynucleotide ODN2216 (Invitrogen); cGAMP was purchased from InvivoGen. Anti-PARP, anti-Mcl1 antibodies were obtained from Cell Signaling. Antibodies used for flow cytometry were purchased from eBioscience (CD45.2 Alexa Fluor 700, CD3 PE-Cy7, CD4 APC-efluor780, CD8 PerCP-efluor710, FOXP3 Alexa Fluor 700, CD45.2 eFluor 450, CD11b APC-eFluor 780, Ly-6C PE, MI-IC II PE-eFluor 610, CD24 APC, F4/80 PerCP-Cy5.5, CD103 FITC, CD11c Alexa Fluor 700). Invitrogen (CD4 QDot 605, Granzyme B PE-Texas Red, Granzyme B APC), BD Pharmingen (Ki-67-Alexa Fluor 488). Anti-phospho-erine-396 of IRF3 and anti-IRF3 antibodies were purchased from Cell signaling.

Statistics

Two-tailed unpaired Student's t test was used for comparisons of two groups in the studies. Survival data were analyzed by log-rank (Mantel-Cox) test. The p values deemed significant are indicated in the figures as follows: *, P<0.05; , P<0.01; *, P<0.001; ****, P <0.0001.

Tumor Infiltrating Lymphocytes (TIL) Preparation

Tumors were dissociated from mice and the total weight of tumor was evaluated before grinded with scissors. Tumors were then digested with 1.7 U/ml Liberase (Roche) and 100 μg/ml DNAse (Sigma) in RPMI 1640 and incubated at 37° C. shaker for 30 min. After digestion, the cell samples were diluted in RPMI 1640 and passed through a cell strainer. Next Cells were washed with RPMI 1640 and resuspended in FACS buffer. Single cells were kept on ice before staining for flow cytometric analysis.

Flow Cytometry of TIL

TILs were pre-incubated with 2.4G2 mAb to block FcγR binding, and stained with panels of antibodies for 30 min on ice. Fluorochrome-conjugated antibodies against CD45.2 (104), CD11b (M1/70), Ly-6C (HK1.4), MHC II (M5/114.15.2), CD24 (M1/69), F4/80 (BM8), CD103 (2E7) and CD11c (N418) were purchased from eBioscience. All antibodies were tested with their respective isotype controls. Viability was assessed by staining with LIVE/DEAD kit (Invitrogen). All samples were acquired with a LSRII flow cytometer (Becton Dickinson) and analyzed with FlowJo software (Tree Star).

Protocol for the Generation of Primary Fibroblasts from Mouse Skin

Mice were euthanized by $CO_2$ inhalation, shaved, and chemically depilated. They were submerged in 70% ethanol for 1-2 min. Truncal skins were cut out, and placed in PBS on the lid of a 100-mm tissue culture dish and spread it out with the epidermal side down. After removal of the subcutaneous tissue by scraping the dermal side using two pairs of forceps, skin samples were incubated with 500 μl dispase (0.5 U/ml)/PBS for 45 min at 37° C. Skin samples were placed on the lid of a 100-mm tissue culture dish with the epidermal side up, and the epidermis was removed mechanically using two pairs of forceps. The dermal sheets were washed with PBS four times before they were digested in type I collagenase (4 mg/ml in PBS with 1% BSA) for three hours at 37° C. Cells were cultured in DME medium with 20% FBS for 1-2 weeks.

Example 1

MVA Induces Type I IFN Production in Murine cDCs

To test whether MVA can induce type I IFN induction, bone marrow-derived dendritic cells were cultured in the presence of GM-CSF (GM-CSF-BMDCs or cDCs) and infected with either WT VAC or MVA at a multiplicity of infection (MOI) of 10. Supernatants were collected at various time points post infection (1, 4, 8, 14, and 22 hours) and IFN-α and IFN-β protein levels evaluated by ELISA. As shown in FIG. 1A, both IFN-α and IFN-β were detected at 8 h post-infection with MVA and continued to accumulate up to 24 h post-infection.

Figure 1B:
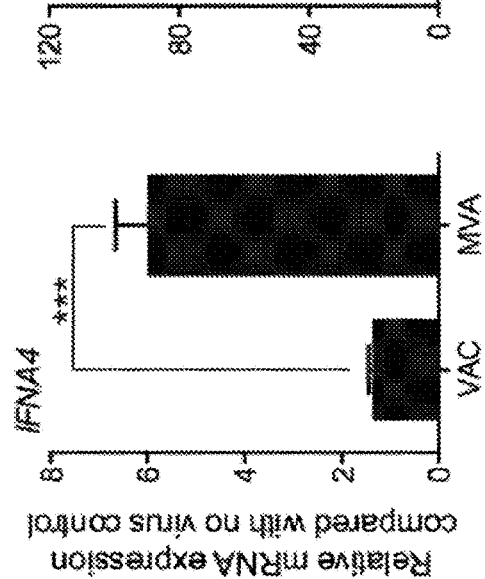

To test whether WT VAC or MVA infection of cDCs affects type I IFN gene expression, quantitative real-time PCR analysis was performed using RNA isolated from GM-CSF-cultured cDCs infected with WT VAC or MVA at 6 h post-infection. Mock-infection controls were also included in the experiment. As demonstrated in FIG. 1B, MVA infection of cDCs increased IFNA4 and IFNB mRNA levels by 6-fold and 105-fold, respectively, when compared with untreated cells. By contrast, infection with WT VAC increased IFNA4 and IFNB mRNA levels by 2-fold and 6-fold, respectively (FIG. 1B). These results indicate that MVA is a substantially stronger inducer of IFNA4 and IFNB gene expression than WT VAC (p<0.001). This experiment illustrates that WT VAC and MVA have different effects on the host's immune system (here assessed by the effect on dendritic cells) starting with the ability of MVA but not WT VAC to induce expression of Type I interferons represented by IFN-α and IFN-β.

Example 2

MVA-Induced Type I IFN Production in Murine cDCs is Dependent on IRF3/IRF7/IFNAR1

Transcription factors IRF3 and IRF7 are key regulators of type I IFN induction and are critical for host defense against virus infections (67) (Sato et al., *Immunity* 13: 539-548, 2000). To test whether in MVA-induction of type I IFN requires IRF3 and IRF7, cDC were generated from IRF3$^{-/-}$, IRF7$^{-/-}$ and WT mice (age-matched), and infected with MVA. MVA-induced IFN-α/β secretion was abolished in IRF3 deficient cDCs (FIG. 2A). IRF7$^{-/-}$ cells fail to produce IFN-α in response to MVA infection, while IFN-β induction was reduced by 57% in MVA-infected IRF7$^{-/-}$ cells (FIG. 2B).

To assess whether the type I IFN positive feedback loop mediated by IFNAR1 is required for the induction of IFN, IFNAR1$^{-/-}$ cDCs and WT controls were infected with MVA at a MOI of 10 and IFN-α/β secretions levels evaluated by ELISA. IFN-α induction by MVA was abolished in IFNAR1$^{-/-}$ cells, whereas IFN-β induction by MVA was reduced by 45% in IFNAR1$^{-/-}$ cells compared with WT controls (FIG. 2C). Collectively, these results indicate that: (i) IRF3 is the critical transcription factor for MVA-induced type I IFN production, and (ii) IRF7 and IFNAR1 play roles in amplifying type I IFN signaling induced by MVA infection. These results therefore confirm the ability of MVA to induce type I IFN via a mechanism relevant in the activation of the immune system.

Example 3

MVA-Induced Type I IFN Induction is Dependent on STING

Figure 3A:
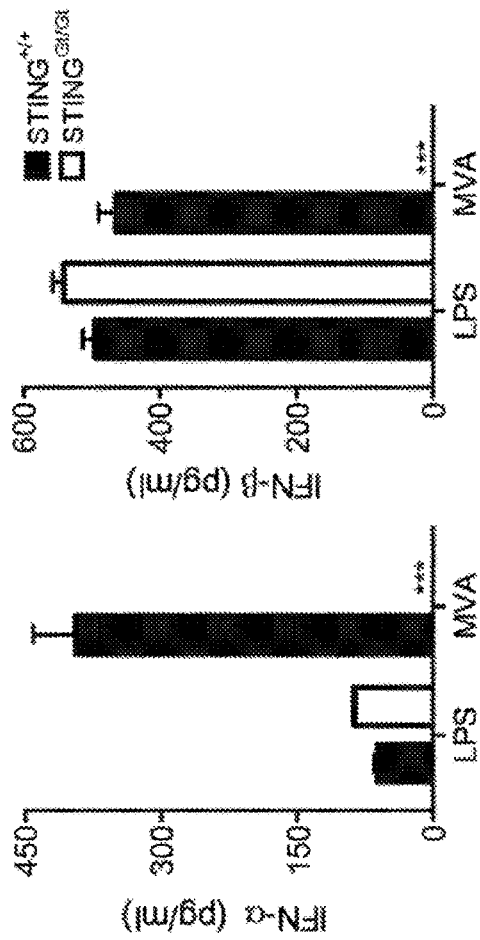
Figure 3B:
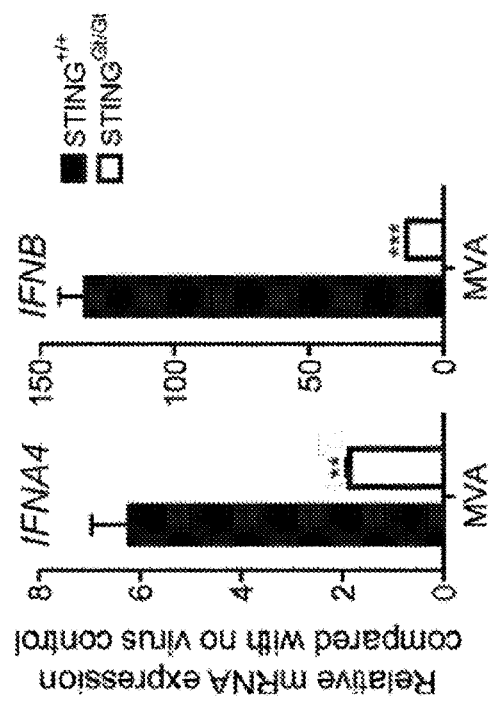

STING is an endoplasmic reticulum-associated protein essential for type I IFN induction in response to intracellular DNA or DNA pathogens including bacteria and DNA viruses (68, 69) (Ishikawa et al. Nature 455: 674-678 (2008); Barber et al. *Curr Opin Immunol* 23: 10-20 (2011). To test whether STING is required for type I IFN induction in cDCs by MVA, cDCs were generated from the N-ethyl-N-nitrosourea (ENU)-induced Goldenticket (Gt) mutant mice (Sting$^{Gt/Gt}$) harboring a single nucleotide variant of Sting resulting in a functionally null allele (70) (Sauer et al. *Infect Immun* 79: 688-694 (2011)). cDCs from age-matched WT mice were used as a control. Cells were either infected with MVA at a MOI of 10 or treated with lipopolysaccharide (LPS). MVA induction of IFN-α/β was abolished in Sting$^{Gt/Gt}$ cells, whereas LPS-induced IFN-α/β production was not affected (FIG. 3A). Induction of IFNA4 mRNA by MVA was reduced from 6-fold in WT cells to 2-fold in Sting$^{Gt/Gt}$ cells, whereas induction of IFNB mRNA by MVA was reduced from 133 fold in WT cells to 14 fold in Sting$^{Gt/Gt}$ cells (FIG. 3B). Furthermore, Western blot analysis demonstrated that MVA-induced IRF3 phosphorylation peaked at 4 and 6 h post infection in WT cDCs and was absent in Sting$^{Gt/Gt}$ cDCs (FIG. 3C). Together, these results demonstrate that STING is essential for MVA-induced type I IFN production and IRF3 phosphorylation in cDCs.

The ability of MVA to activate STING and its downstream signaling pathway including transcription factor IRF3 makes it different from replication competent WT VAC, which is unable to activate STING/IRF3. The inventors infer that the mechanism of MVA-mediated antitumor immunity would be different from the mechanism of oncolytic effects mediated by WT VAC or recombinant replication competent VAC with deletion of thymidine kinase.

Example 4

MVA Triggers Type I IFN Production in vivo in a STING/IRF3-Dependent Manner

To test whether MVA triggers type I IFN production in vivo in a STING/IRF3-dependent manner, Sting$^{+/+}$, Sting$^{Gt/Gt}$, and IRF3$^{-/-}$ were infected with 2×10$^7$ pfu via tail vein injection. Serum was collected at 6 h post-infection. MVA infection of Sting$^{+/+}$ mice induced IFN-α and IFN-β production to the levels of 798 pg/ml and 1017 pg/ml, respectively, which was abolished in Sting$^{Gt/Gt}$, and IRF3$^{-/-}$ mice (FIG. 3D). These results indicate that MVA-induced type I IFN production in vivo is also dependent on STING and transcription factor IRF3.

The ability of MVA to induce type I IFN production in a STING/IRF3-dependent manner, through intravenous delivery, also points to IFN-dependent therapeutic effects mediated by MVA.

Example 5 cGAS is Required for the Induction of Type I IFN by MVA in cDCs

Figure 4A:
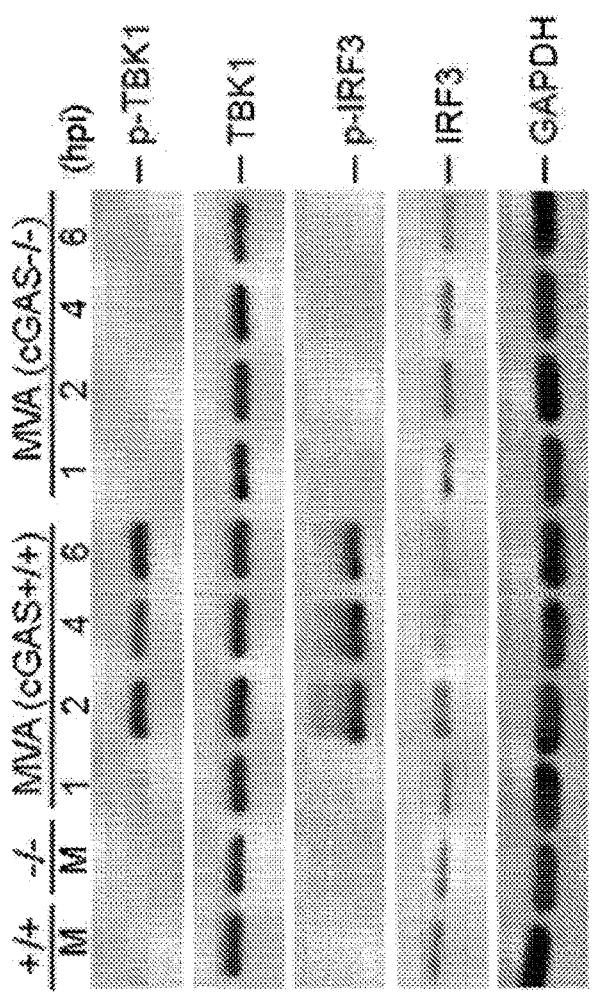
FIGS. 4A-4C are a series of graphical representations demonstrating that cGAS is the critical cytosolic DNA sensor for MVA infection of cDCs.
Figure 4B:
Figure 4C:
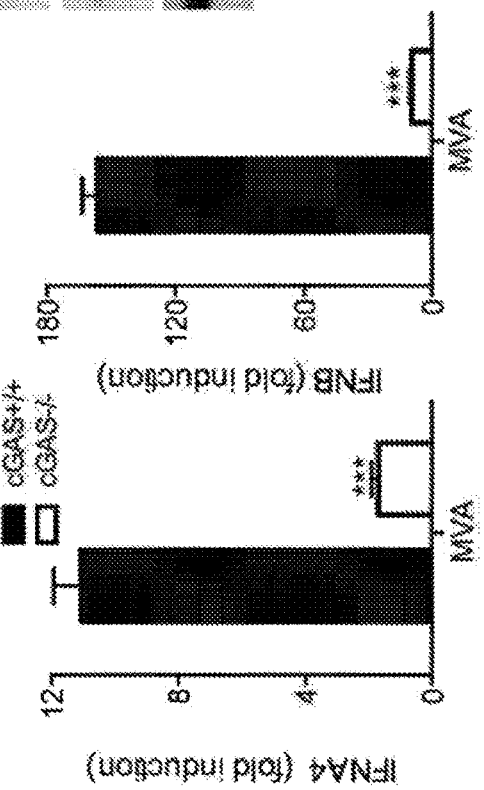

The STING/IRF3 pathway can be activated by cyclic GMP-AMP (cGAMP), a second messenger produced by cyclic GMP-AMP synthase (cGAS) in response to DNA virus infection (71) (Sun et al. *Science* 339: 786-791 (2013). To test whether MVA infection of cDCs triggers type I IFN induction via the cytosolic DNA-sensing pathway mediated by the cytosolic DNA sensor cGAS, cDCs were generated from cGAS$^{-/-}$ (72) (Li et al., *Science* 341 (6152): 1390-1394 (2013)) mice and age-matched WT controls and infected with MVA. As shown in FIG. 4A, MVA-induced IFN-α/β production was abolished in cGAS$^{-/-}$ cells. Induction of IFNA4 and IFNB mRNA by MVA was also diminished in cGAS$^{-/-}$ cells compared with WT cells (FIG. 4B). Finally, Western blot analysis demonstrated that MVA-induced phosphorylation of TBK1 and IRF3 was absent in cGAS$^{-/-}$ cells (FIG. 4C). These results demonstrate that cGAS is a critical cytosolic DNA sensor for MVA.

Example 6

MVAΔE3L Induces Higher Levels of Type I IFN Production in Murine cDCs than MVA

Figure 5A:
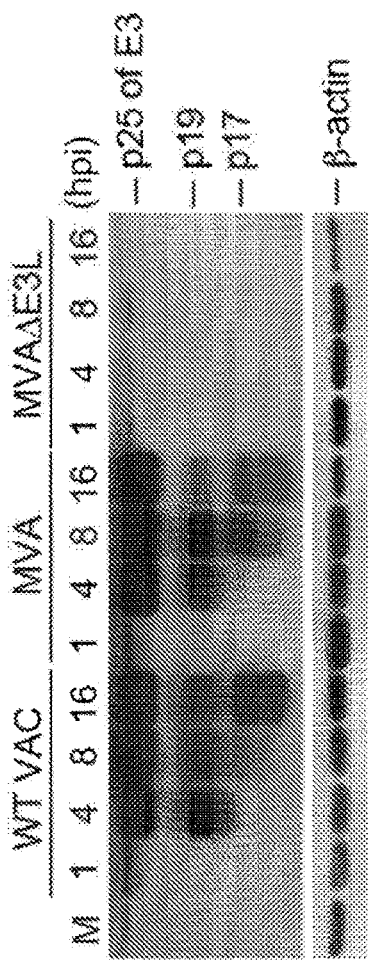
FIGS. 5A-5D are a series of graphical representations showing that MVAΔE3L induces higher levels of type I IFN gene expression in BMDCs than MVA does.
Figure 5B:
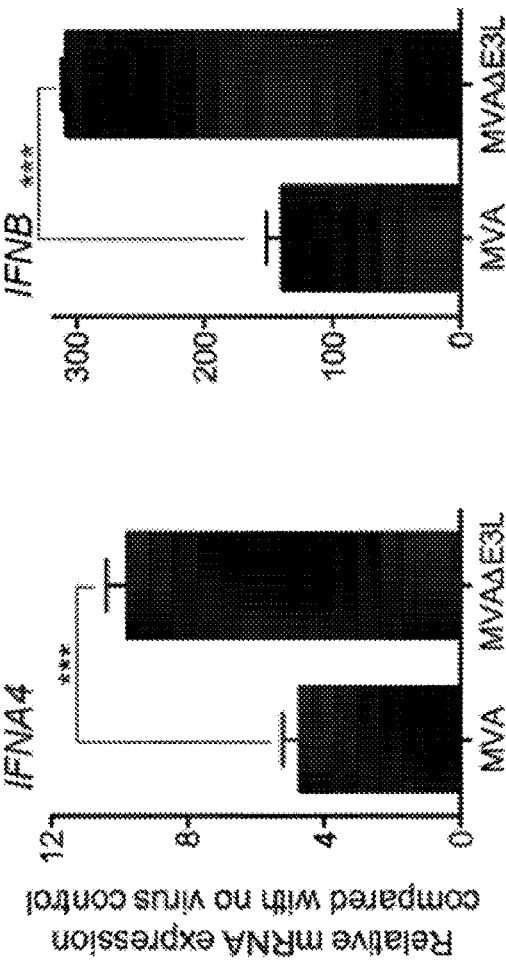
Figure 5C:
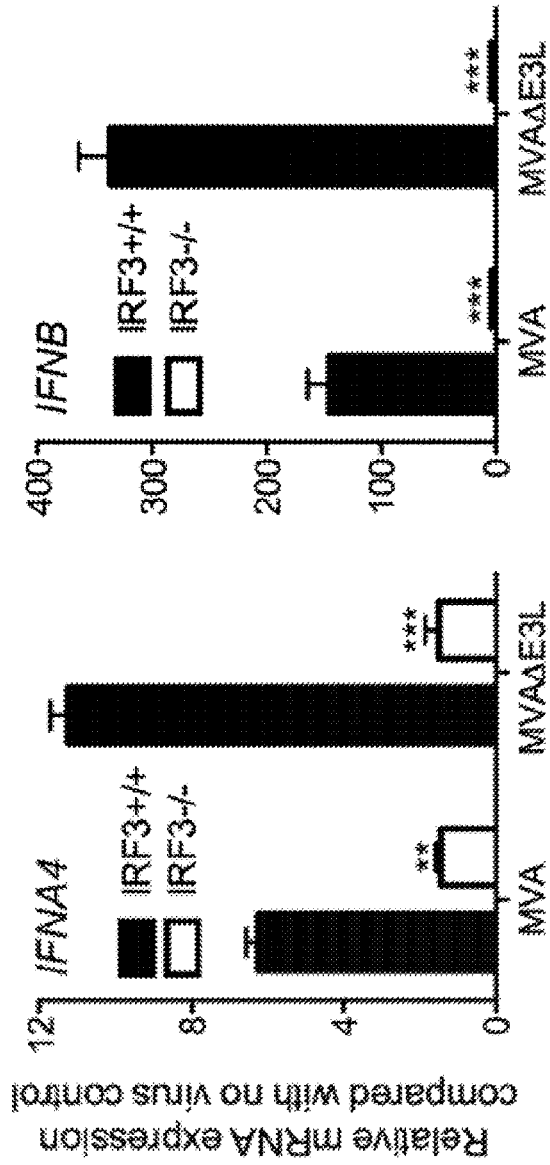
Figure 5D:
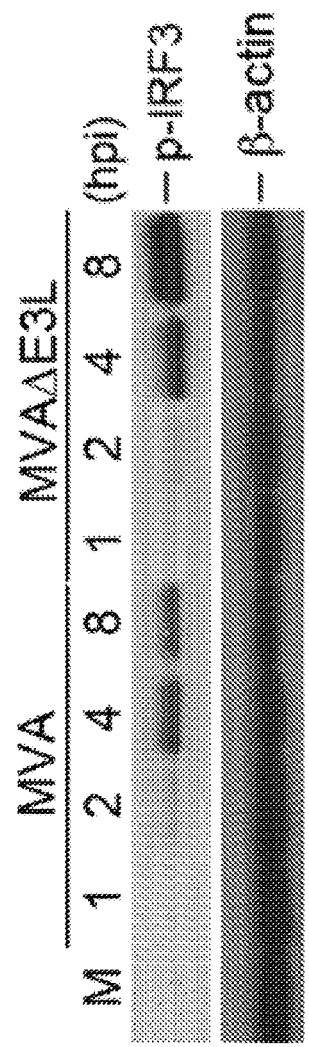

E3 is a key virulence factor that attenuates various innate immune responses, including type I IFN induction. MVA retains the E3L gene. Western blot analysis showed that E3 protein was produced in WT VAC and MVA-infected BMDCs, but not in MVAΔE3L-infected cells (FIG. 5A). To test whether E3 plays an inhibitory role in MVA sensing in cDCs, the induction of type I IFN gene expression was compared between MVA and MVAΔE3L. It was found that MVAΔE3L induced higher levels of IFNA4 and IFNB mRNAs than MVA (FIG. 5B) (P<0.001). This induction was abolished in cells lacking transcription factor IRF3 (FIG. 5C). Furthermore, Western blot analysis demonstrated that MVAΔE3L infection induced higher level of phospho-IRF3 than MVA at both 4 and 8 h post infection (FIG. 5D). These results suggest that E3 dampens innate immune-sensing of MVA and that removing E3 from MVA results in enhanced activation of type I IFN gene expression. The inventors infer that MVAΔE3L may have stronger antitumor effects than MVA due to its superior ability to induce type I IFN compared with MVA.

Example 7

Figures 6A, 6B, 6C:
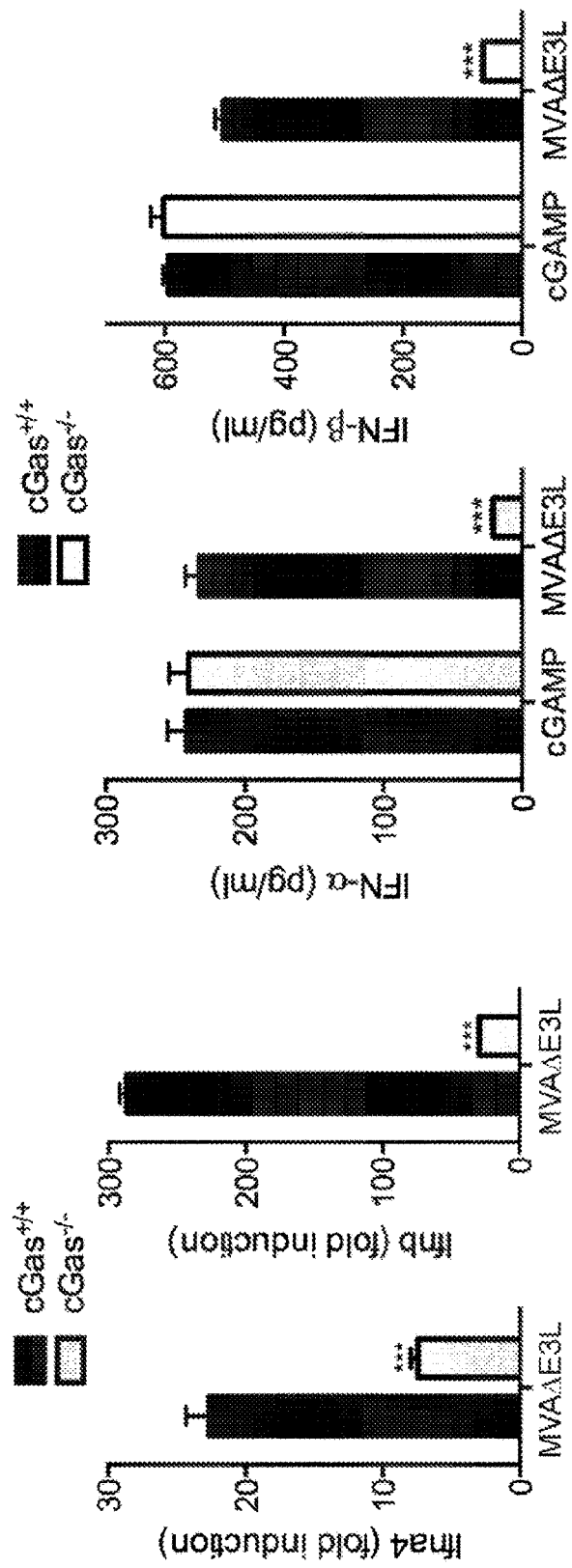
FIGS. 6A-6C are a series of bar graphs showing that cGAS is required for the induction of type I IFN by MVAΔE3L in cDCs.

The Cytosolic DNA-Sensing Pathway Mediated by cGAS Plays an Important Role in MVAΔE3L-Induced Type I IFN Induction in cDCs To test whether MVAΔE3L infection of cDCs triggers type I IFN induction via the cytosolic DNA-sensing pathway mediated by the cytosolic DNA sensor cGAS (cyclic GMP-AMP synthase) (71, 73) (Sun et al., Science 339 (6121): 786-791 (2013); Wu et al., Science 339 (6121): 826-830 (2013)), and its adaptor STING (68, 74) (Ishikawa et al., Nature 455 (7213): 674-678 (2008); Gao et al., Cell 154 (4): 748-762 (2013)), cDCs were generated from cGAS$^{-/-}$ (72) (Li et al., Science 341 (6152): 1390-1394 (2013)) mice and age-matched WT controls and infected with MVAΔE3L. Using quantitative real-time PCR analysis, it was found that MVAΔE3L-induced IFNA4 and IFN-β gene expression at 6 h post infection were both reduced in cGAS-deficient cells (FIG. 6A, P<0.001). ELISA analysis of supernatants collected at 22 h post infection also showed that MVAΔE3L-induced IFN-α/β secretion was significantly reduced in cGAS-deficient cells (FIG. 6B, P<0.001). By contrast, cGAMP treatment at 15 μM final concentration induced IFN-α/β secretion in both WT and cGAS$^{-/-}$ cDCs at similar levels. Finally, Western blot analysis demonstrated that MVAΔE3L-induced phosphorylation of IRF3 was absent at 2 and 4 h post infection and significantly reduced at 6 and 8 h post-infection in cGAS$^{-/-}$ cells (FIG. 4C). These results demonstrate that cGAS is a critical cytosolic DNA sensor for MVAΔE3L. These results also imply that the ability of MVAΔE3L to induce cGAS/STING pathway in dendritic cells may contribute to its therapeutic benefits. Based on results obtained by the present inventors with inactivated MVA and described in PCT US2016/019663 filed Feb. 25, 2016, incorporated by reference in its entirety for all purposes, the inventors expect that the antitumor effects of MVAΔE3L will be diminished in mice that are deficient of cGAS or STING. WT VAC with deletion of E3 is unable to induce type I IFN in dendritic cells (data not shown), indicating that viral inhibitor(s) of the cGAS/STING pathway expressed by WT VAC might be missing in MVA.

Example 8

Figure 7A:
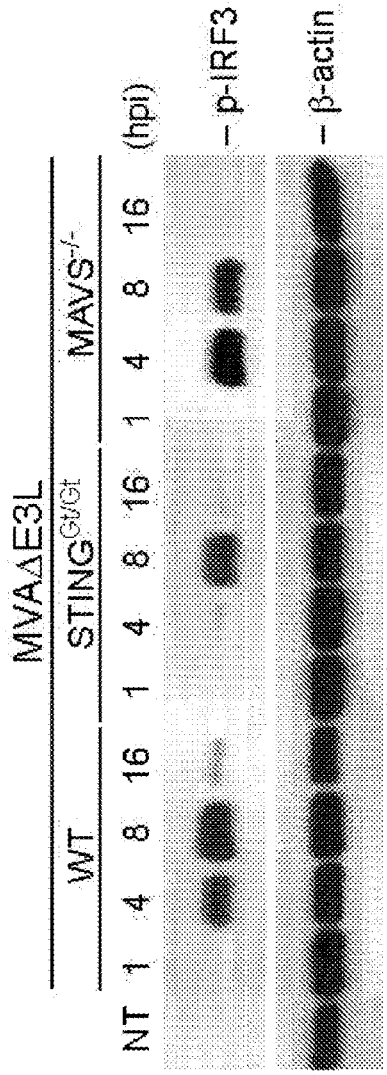
FIGS. 7A-7B are a series of scanned images of Western blot data showing that dsRNA-sensing pathway also plays a role in MVAΔE3L-induced phosphorylation of IRF3.
Figure 7B:
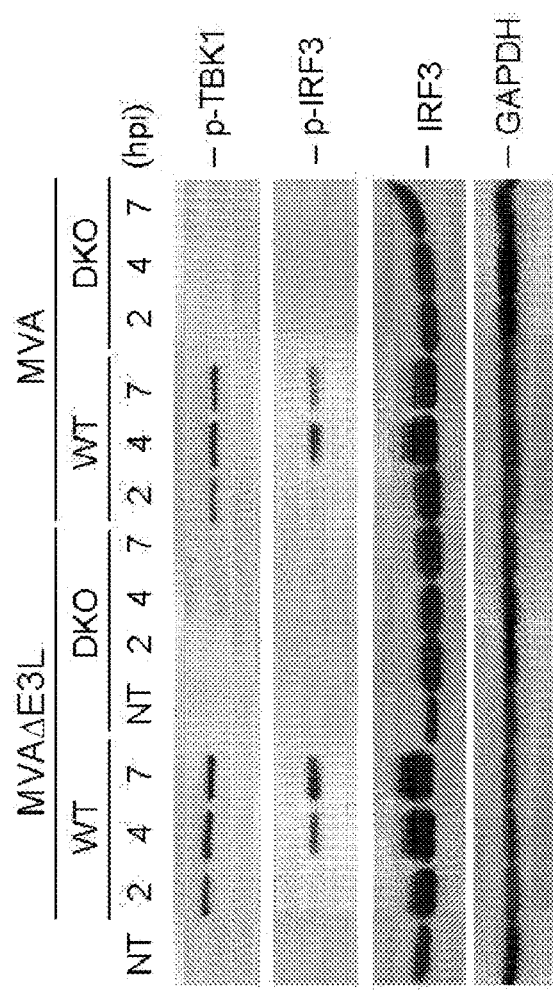

The Cytosolic dsRNA-Sensing Pathway Mediated by MDA5/MAVS Also Contributes MVAΔE3L-Induced type I IFN Production in cDCs Western blot analysis showed that MVAΔE3-induced phosphorylation of IRF3 was diminished at 4 h and reduced at 8 h post infection in STING-deficient bone marrow-derived cDCs generated from STING$^{Gt/Gt}$ mice compared with WT cells (FIG. 7A). MVAΔE3L-induced phosphorylation of IRF3 was also reduced at 8 h post infection in MAVS$^{-/-}$ cDCs compared with WT cells (FIG. 7A). These results suggest that MVAΔE3L infection of cDCs could be sensed by both the cytosolic DNA-sensing pathway mediated by cGAS/STING as well as the cytosolic dsRNA-sensing pathway mediated by MDA5/MAVS. To test that hypothesis, STING$^{Gt/Gt}$/MDA5$^{-/-}$ mice were generated, and double-deficient cDCs isolated. MVAΔE3L-induced phosphorylation of TBK1 and IRF3 was abolished in STING$^{Gt/Gt}$/MDA5$^{-/-}$ cells (FIG. 7B). These results indicate that the cytosolic dsRNA-sensing pathway also plays a role in sensing dsRNA produced by MVAΔE3L. Taken together, these results demonstrate that MVAΔE3L infection in cDCs leads to the cytosolic detection of viral DNA and dsRNA by the cGAS/STING and MDA5/MAVS signaling pathways, respectively, which results in the activation of TBK1 and IRF3 and the induction of type I IFN gene expression. It has been shown that intravenous delivery of synthetic dsRNA activates MDA5 and induces antitumor effects (Tormo et al., 2009). The ability of MVAΔE3L to induce activate MDA5 through the production of dsRNA in both immune cells, fibroblasts (see example) and tumor cells (see example) may also contribute to its therapeutic benefits.

Example 9

The Cytosolic DNA-Sensing Pathway Mediated by cGAS/STING Plays an Important Role in MVAΔE3L-Induced Ifnb Gene Expression in Murine Primary Fibroblasts Skin dermal fibroblasts constitute an important cell type in melanoma stromal cells, contributing to melanoma progression and metastasis through the production of growth factors and other soluble mediators (Li et al., Oncogene 2003; Inada et al., 2015). To investigate whether skin dermal fibroblasts also respond to MVA or MVAΔE3L, the inventors generated primary skin fibroblasts from WT and cGAS$^{-/-}$ mice, and infected them with MVA or MVAΔE3L at a MOI of 10. Cells were collected at 6 h post infection. Using quantitative real-time PCR analysis, the inventors found that MVAΔE3L infection induced higher levels of Ifnb, Ccl4, and Il6 gene expression at 6 h post infection than MVA (FIG. 8 A-D). The induction of Ifnb, Ccl4, Cc15, and I16 gene expression by MVA and MVAΔE3L was diminished in cGAS-deficient fibroblasts (FIG. 8A-D). These results demonstrate that MVA and MVAΔE3L infection of fibroblasts can be detected by the cytosolic DNA sensor cGAS, which leads to the induction of IFNB, and other proinflammatory cytokines and chemokines. STING is a critical adaptor for the cytosolic DNA-sensing pathway. MDA5 is a cytosolic dsRNA sensor (Gitlin et al., PNAS 2006). To test whether STING or MDA5, or both are also involved in sensing MVA or MVAΔE3L in skin fibroblasts, the inventors generated primary skin fibroblasts from WT, STING$^{Gt/Gt}$, MDA5$^{-/-}$, and STING$^{Gt/Gt}$ MDA5$^{-/-}$ mice, and infected them with MVA or MVAΔE3L. Quantitative real-time PCR analysis showed that MVA or MVAΔE3L induced Ifnb, Cc14, Cc15, and I16 gene expression was largely diminished in STING-deficient cells, confirming that the cytosolic DNA-sensing pathway mediated by cGAS/STING is critical for detecting viral infection and inducing an antiviral innate immunity. There were some low residual levels of I16 and Cc14 gene expression induced by MVAΔE3L in STING-deficient cells, and those levels were gone in the STING and MDA5-double deficient cells, indicating that MDA5 plays a supporting role in detecting dsRNA produced by MVAΔE3L virus. The inventors conclude that in skin dermal primary fibroblasts, MVA is detected by the cGAS/STNG cytosolic DNA-sensing pathway to induce Ifnb, Cc14, Cc15, and I16 gene expression, whereas MVAΔE3L activates both cGAS/STING and MDA5 pathways to induce innate immunity.

Example 10

The Cytosolic DNA-Sensing Pathway Mediated by cGAS/STING Plays an Important Role in MVA and MVAΔE3L-Induced type I IFN, Inflammatory Cytokine and Chemokine Production in Murine Primary Fibroblasts To correlate protein secretion from infected skin fibroblasts, the inventors collected supernatants from skin fibroblasts from WT, STING$^{Gt/Gt}$, MDA5$^{-/-}$, and STING$^{Gt/Gt}$ MDA5$^{-/-}$ mice infected with MVA or MVAΔE3L and performed ELISA analysis. It was observed that MVAΔE3L infection induced higher secretion levels of IFN-β, IL-6 and CCL4 than MVA. Similar to what it was observed with gene expression analysis, MVA-induced secretion of IFN-β, IL-6 and CCL5 was abolished in STING-deficient cells. Although MVAΔE3L-induced IFN-β and CCL5 were diminished in STING-deficient cells, there were residual levels of IL-6 and CCL4 in the supernatants of STING-deficient cells infected with MVAΔE3L virus, which were abolished in the STING and MDA5-double deficient cells. Taken together, these results showed that skin fibroblasts are an important source for the production of IFN-β, IL-6, CCL4, and CCL5 in response to MVA or MVAΔE3L infection, which is dependent on the cytosolic DNA-sensing pathway. The inventors infer that tumor stromal fibroblasts are also capable of induction of type I IFN and proinflammatory cytokines and chemokines in response to immune activating viruses such as MVA or MVAΔE3L.

Example 11

MVAΔE3L Infection of B16 Melanoma Cells Induces Type I IFN and Inflammatory Cytokines/Chemokines Production To test whether MVAΔE3L infection of B16 melanoma cells also induces type I IFN, and inflammatory cytokine/chemokine production, B16 melanoma cells were infected with MVA or MVAΔE3L at a MOI of 10, or mock-infected (NT). Cells were collected at 6 h post infection and real-time PCR analysis was performed to analyze gene expression. As shown in FIG. 10A-F, MVAΔE3L infection induced higher levels of IFNA4 (FIG. 10A), IFNb (FIG. 10B), Il6 (FIG. 10C), TNF (FIG. 10D), CCL5 (FIG. 10E) and CXCL-10 (FIG. 10F) gene expression than MVA.

Example 12

Infection of B16 Melanoma Cells With Either MVA or MVAΔE3L Induces Apoptosis

Figures 9A, 9B:
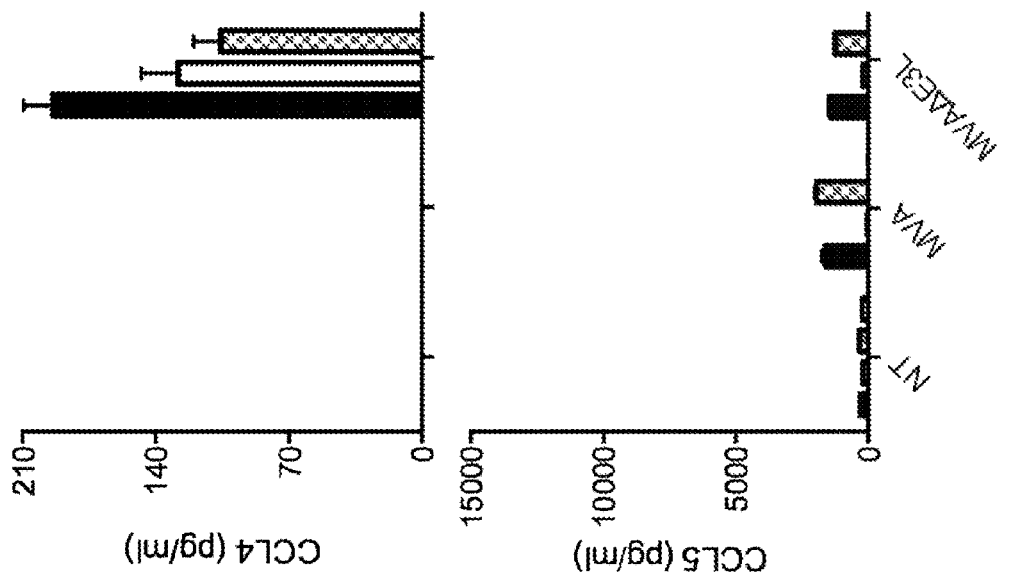
FIGS. 9A-9D are a series of bar graphs showing that MVA and MVAΔE3L infection of murine primary fibroblasts leads to production of IFN-β (FIG. 9A), CCL4 (FIG. 9B), IL-6 (FIG. 9C), and CCL5 (FIG. 9D), which is largely dependent on STING and with some contribution from MDA5.
Figures 9C, 9D:
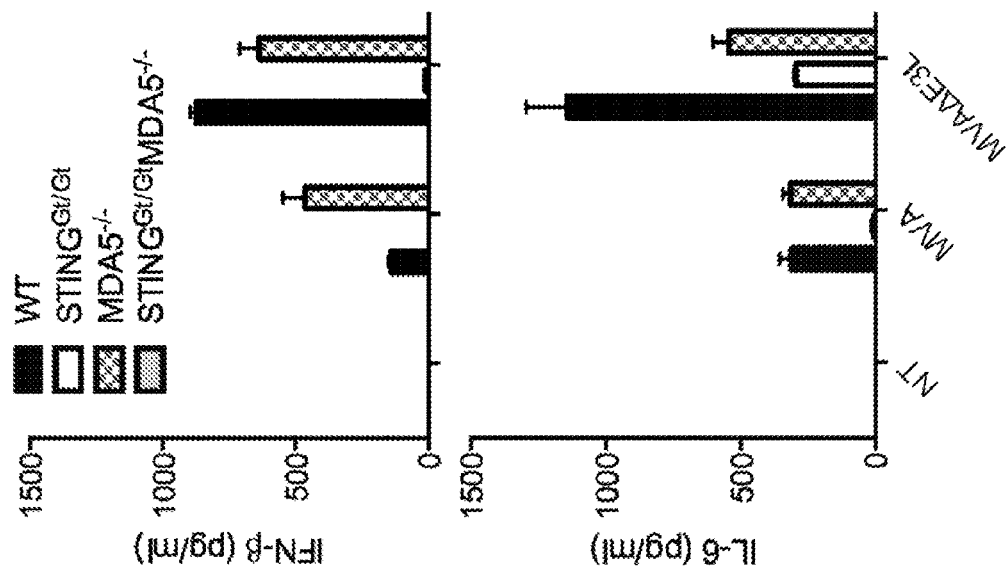

Proteolytic cleavage of poly(ADP-ribose) polymerase (PARP) by caspases is a hallmark of apoptosis. Vaccinia E3 has been shown to inhibit apoptosis induced by dsRNA in HeLa cells (75, 76) (Kibler et al., *J Virol* 71, 1992-2003 (1997); Lee et al., *Virology* 199, 491-496 (1994)). MVAΔE3L induces more apoptosis in chicken embryonic fibroblasts (CEFs) than MVA (28) (Hornemann et al., J Virol 77, 8394-8407 (2003)). To evaluate whether MVA and MVAΔE3L induce apoptosis in melanoma cells, B16 melanoma cells were infected with either MVA or MVAΔE3L at a MOI of 10 and cleavage of PARP was determined using Western blot analysis. As shown in FIG. 9A, both MVA and MVAΔE3L infection triggered cleavage of PARP from 116-kDa full-length protein to 89-kDa fragment at 22 h post infection. Furthermore, MVAΔE3L induced PARP cleavage more efficiently than MVA (FIG. 11A).

Figure 11B:
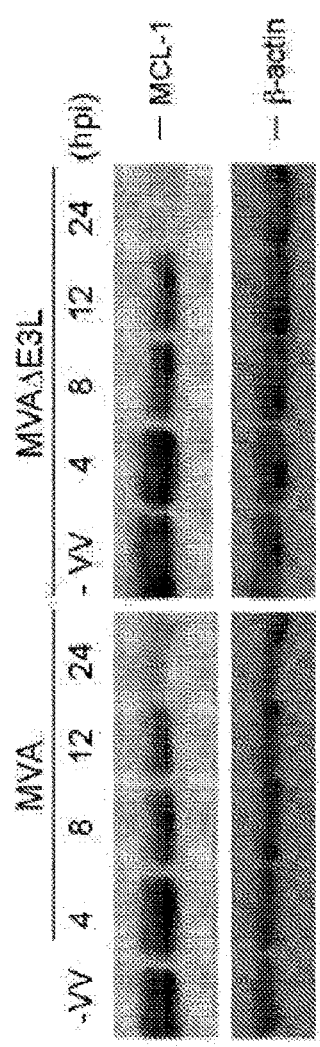
FIGS. 11A-11C are a series of scanned immunoblot images showing that infection of B16-F10 melanoma cells with MVA or MVAΔE3L induces apoptosis.

In accordance with the observation that MVA and MVAΔE3L trigger apoptosis, MVA and MVAΔE3L infection caused the degradation of Myeloid cell leukemia-1 (Mcl-1) protein, an important anti-apoptotic Bcl-2 family member (FIG. 11B). Taken together, these results show that MVAΔE3L infection of melanoma cells triggers apoptosis to the same or even a greater extent than MVA.

Example 13

Figure 12E:
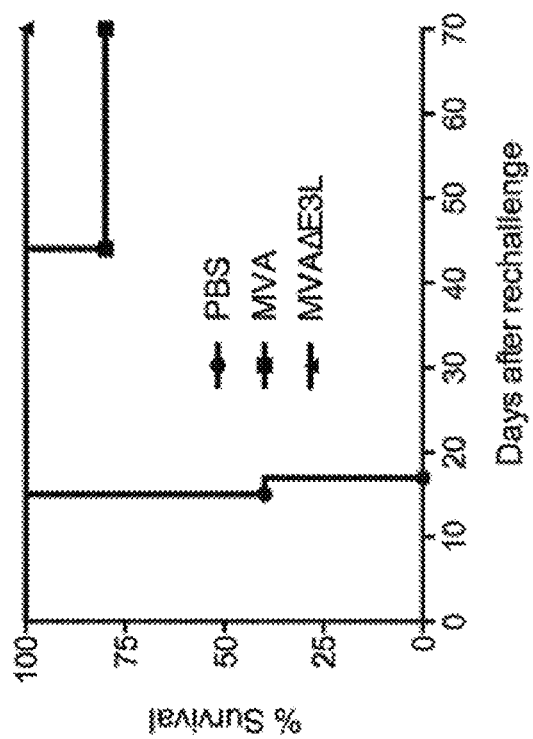
Figure 12D:
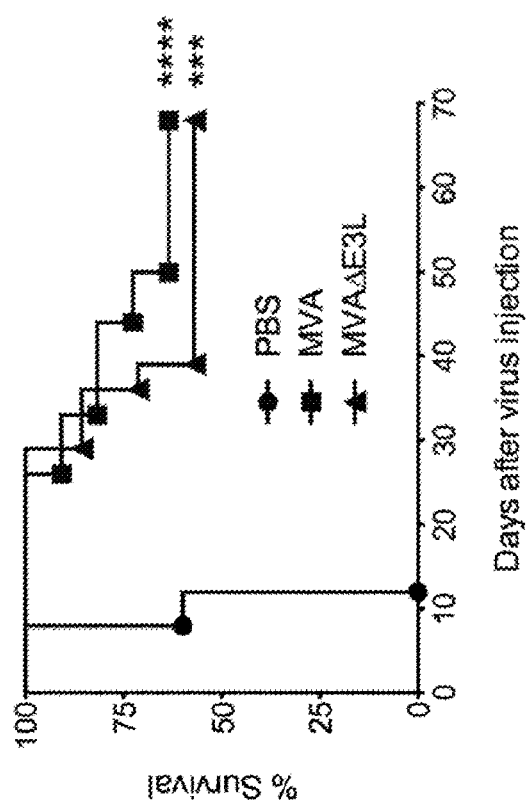

Intratumoral Injection of MVA or MVAΔE3L Leads to Prolonged Survival of Tumor-Bearing Mice and the Generation of Systemic Antitumor Immunity The transplantable in vivo B16 melanoma model involves the intradermal implantation of murine B16F10 melanoma cells (1×10$^5$) on one flank of C57B/6 mice. Twelve days following tumor implantation, when the tumors were approximately 3 mm in diameter, MVA or MVAΔE3L (2×10$^7$ pfu) or PBS was injected to the tumors weekly. Intratumoral injection of MVA resulted in tumor eradication in 60% of treated mice and prolonged survival in the rest (FIG. 12B-D), whereas intratumoral injection of MVAΔE3L resulted in tumor eradication in 57% of treated mice and prolonged survival in the rest (FIG. 12B-D), demonstrating excellent therapeutic efficacy with both agents. By contrast, all of the mice with intratumoral injection of PBS had continued tumor growth and were euthanized at a median of 21 days post tumor implantation (FIGS. 12A and D). In the initial experiment, intratumoral injection of MVA seemed to have at least similar anti-tumor efficacy as MVAΔE3L virus.

To test whether mice whose tumors were eradicated after intratumoral injection of MVA or MVAΔE3L developed systemic anti-tumoral immunity in the animals, animals were challenged by intradermal injection of a lethal dose of B16 melanoma cells (5×10$^4$) to the contralateral side 8 weeks after the eradication of initial tumors. Naïve mice that were never exposed to B16 melanoma cells or viruses were used as a control in the challenge experiment. Animals were followed for 70 days after tumor challenge. 80% of MVA-treated mice and 100% of MVAΔE3L-treated mice survived the tumor challenge, whereas all of the naïve mice developed growing tumors and were eventually euthanized (FIG. 10E). Collectively, these results suggest that intratumoral injection of MVA or MVAΔE3L leads to tumor eradication, prolonged survival, as well as to the development of systemic antitumor immunity. In addition, this experiment indicates efficacy of the disclosed treatments in inhibiting metastasis represented by the tumor challenge.

Example 14

Figure 11C:
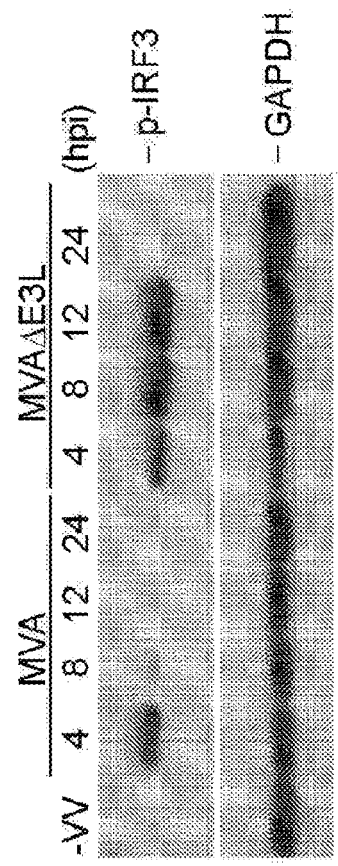
Figure 11A:
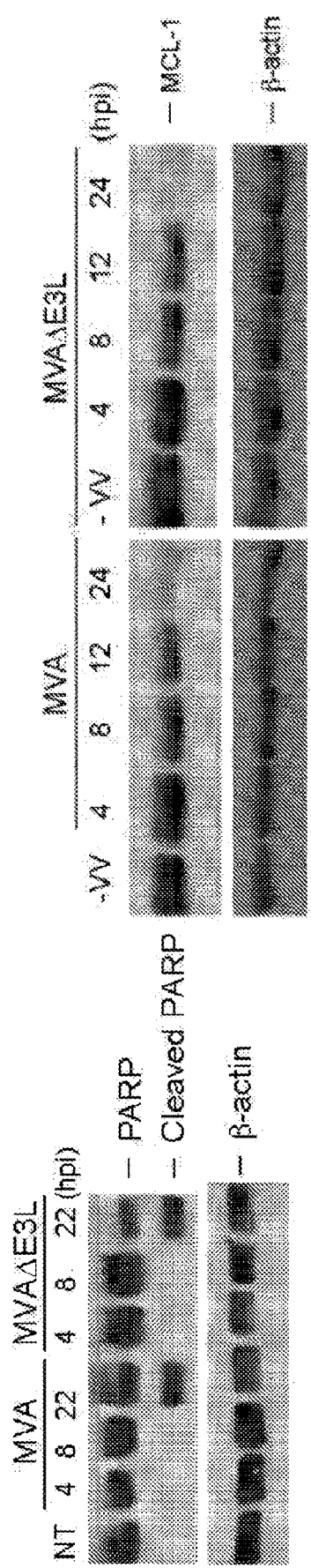
Figure 13C:
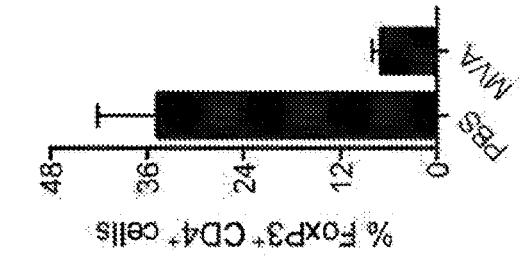
Figure 13F:
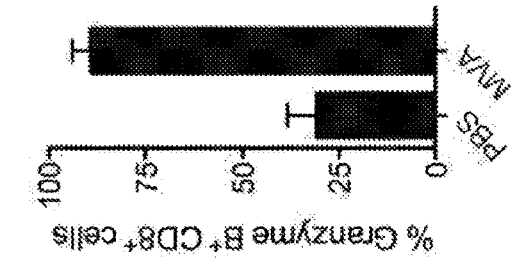
Figures 13A, 13B:
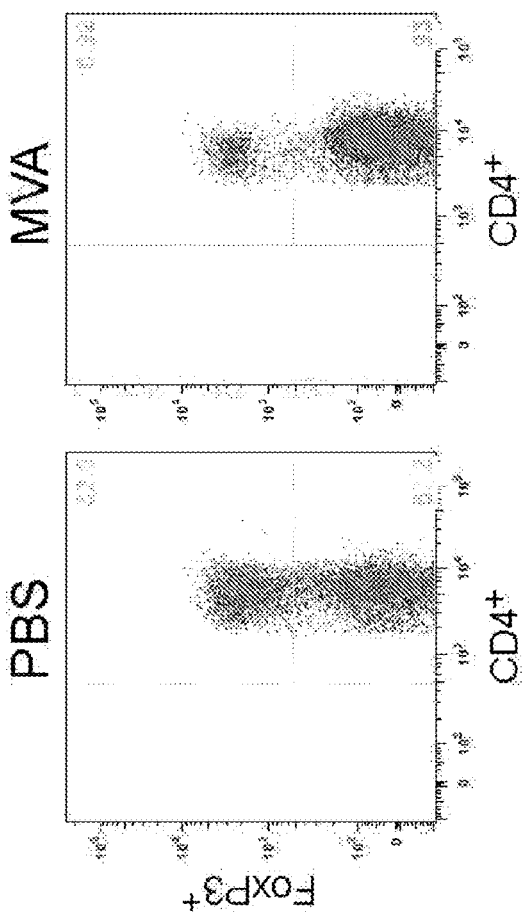
Figures 13D, 13E:
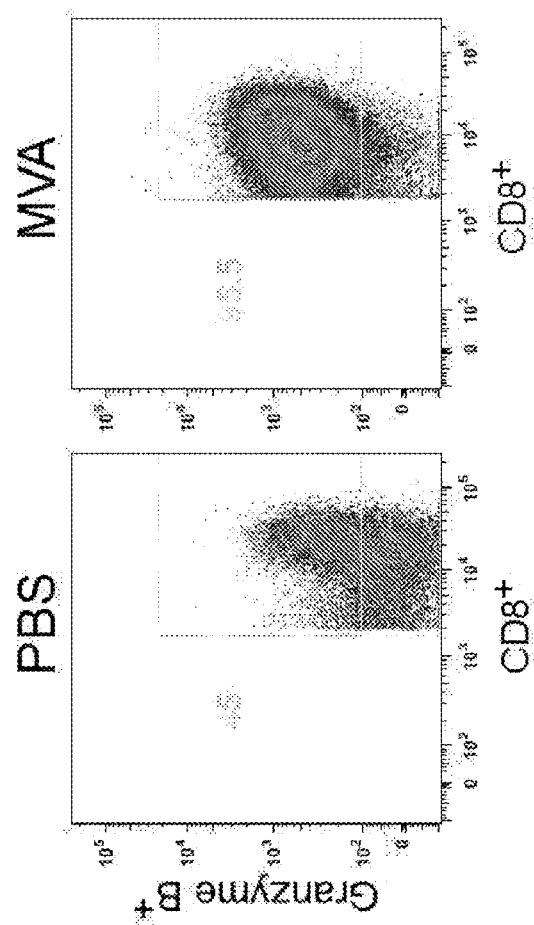

Intratumoral Injection of MVA Leads to Immunological Changes in the Tumor Environment To investigate the immunologic changes within the tumors induced by intratumoral injection of MVA, tumors were harvested at 3 days post intratumoral injection of MVA or PBS and the immune cell infiltrates were analyzed by FACS. We observed that the percentage of Foxp3$^+$ CD4$^+$ T cells (i.e., regulatory CD4+ T cells) decreased from 34.7% in PBS-treated tumors to 7.0% in MVA-treated tumors (P<0.0001, FIG. 13A-C). We also observed an increase in the percentage of CD8$^+$ T cells that express Granzyme B (i.e. expressing the cytotoxic phenotype) within the tumors treated with MVA (89%) compared those treated with PBS (31%) (P<0.0001, FIG. 13D-F). The percentage of Ki-67$^+$ CD8+ T cells (i.e., proliferating CD8+ T cells) was increased from 51% in the PBS-treated tumors to 76% in the MVA-treated tumors (P=0.0004, FIG. 11, G-I). These results indicate that intratumoral injection of MVA dramatically upregulates immune responses in the tumor microenvironment, including proliferation and activation cytotoxic CD8⁺ T cells and a concomitant reduction of CD4+ regulatory T cells within the tumors. We expect to see similar changes in immune cell infiltrates within tumors treated with MVAΔE3L. These experiments have been planned.

Example 15

Intratumoral Injection of MVA Also Induces Immunological Changes in the Tumor-Draining Lymph Nodes (TDLNs)

To test whether intratumoral injection of MVA also causes immunological changes in TDLNs, TDLNs were isolated from MVA- or PBS-injected mice at three days post treatment, and analyzed by FACS. The percentage of Granzyme B⁺ CD8⁺ T cells in TDLNs increased from 0.15% in mice treated with PBS to 4.6% in mice treated with MVA (P=0.0002, FIG. 14A-C). In addition, the percentage of Ki-67⁺ CD8⁺ T cells increased from 7.2% in mice treated with PBS to 15% in mice treated with MVA (P=0.0008, FIG. 14D-F). These results indicate that there are more activated and replicating CD8⁺ T cells in the TDLNs in MVA-treated mice than in PBS-treated mice. Taken together, these results indicate that intratumoral injection of MVA leads to the activation and proliferation of both CD8⁺ T cells not only locally within the tumor but also systemically in the host.

Example 16

MVA and MVAΔE3L Infection of MC38 Murine Colon Adenocarcinoma Cells Induces Type I IFN and Inflammatory Cytokines/Chemokines Production To address whether MVA and MVAΔE3L also trigger similar responses in other types of solid tumor cells, the abilities of MVA and MVAΔE3L to induce type I IFN pathway were tested in the MC38 colon adenocarcinoma cells. MC38 cells were infected with MVA or MVAΔE3L at a MOI of 10, or mock-infection control. Supernatants were collected at 22 h post infection. Using ELISA, it was determined that MVAΔE3L induced higher levels of production of IFN-β, IL-6, CCL4 and CCL5 in MC38 cells than MVA (FIG. 15A-D). Similarly, real-time PCR analysis revealed that MVAΔE3L infection triggered higher levels of Ifnb, Il6, Ccl4, and Ccl5 gene expression in MC38 cells than MVA (FIG. 15E-H). Western blot analysis demonstrated that MVAΔE3L infection triggered higher levels of phosphorylation of IRF3 than MVA in MC38 cells at 22 h post infection (FIG. 15I). These results show that the efficacy of the present treatment is not confined to melanoma. Moreover, because the choice of colon carcinoma was arbitrary and because the two tumors are not related. Other than both being solid tumors and of basal cell origin (carcinomas), the present results can be extrapolated to all carcinomas. Moreover, because the present inventors have shown that MVA and MVAΔE3L exert their activity on the immune system systemically and in a tumor antigen-independent manner, the present findings can be further extrapolated to solid tumors.

Example 17

MVAΔE3L Infection of MC38 Murine Colon Adenocarcinoma Cells Induces Apoptosis

To investigate whether MVA and MVAΔE3L also trigger apoptosis in MC38 murine colon adenocarcinoma cells, MC38 cells were infected with MVA or MVAΔE3L at a MOI of 10, or mock-infection control. As observed in the B16 melanoma cells, Western blot analysis showed that both MVA and MVAΔE3L triggered cleavage of PARP from 116-kDa full-length protein to 89-kDa fragment (at 22 hours, FIG. 15I). Together, Examples 16 and 17 indicate that each of MVA and MVAΔE3L has the capacity to induce type I IFN and inflammatory cytokines/chemokines production, as well as apoptosis in different types of cancer cells. MVAΔE3L seems to be a stronger inducer of both type I IFN and pro-inflammatory cytokine and chemokine production, as well as apoptosis compared with MVA. Nevertheless, both results indicate that the immune response elicited by the present viruses carries through to apoptosis, resulting in cancer cell death. This further establishes the presently disclosed treatments as a viable approach to therapy of melanoma, colon cancer, carcinomas in general and indeed solid tumors.

Example 18

MVAΔE3L Inhibits Tumorigenesis in Murine Model of Colon Carcinoma

Experimental studies disclosed in Example 11 showed that intratumoral injection of MVA or MVAΔE3L leads to tumor eradication and systemic anti-tumoral immunity in a murine transplantable B16 melanoma model. To test whether MVAΔE3L is capable of inhibiting tumor growth in other solid tumors, the inventors tested the anti-tumor effects of MVAΔE3L in a murine colon carcinoma implantation model. Colon carcinoma is representative of a tumor not related to melanoma but was otherwise a random choice. 2×10⁵ MC38 colon carcinoma cells were intradermally implanted into the right flank of C57B/6 mice. Tumors were allowed to form for 7 days, after which MVAΔE3L (2×10⁷) or PBS control were intratumorally injected into mice. Tumors were measured at prior to injection (day 0) and for up to 45 days post injection and tumor volume was calculated according the following formula: 1 (length)×w (width)×h(height)/2. As shown in FIGS. 16 (A and B), tumors treated with MVAΔE3L were significantly smaller than PBS-treated tumors. Furthermore, mice treated with MVAΔE3L exhibited improved survival as demonstrated by the Kaplan-Meier survival curve of tumor-bearing mice injected with PBS or MVAΔE3L (FIG. 16C). Collectively, these findings reveal that in the context of colon cancer as well as melanoma, MVAΔE3L maintains the capacity to inhibit tumorigenesis and tumor growth. Collectively, results observed here as well as in Example 13 and Example 17 demonstrate and illustrate that MVAΔE3L is efficient in promoting anti-tumor effects in various solid tumors and that the findings described in this disclosure are not limited to melanoma but can be extrapolated to other solid tumors of diverse origins.

Example 19

Intratumoral Injection of MVA and MVAΔE3L Leads to Antitumor Effects in Both Injected and Non-Injected Distant Tumors and Enhanced Survival Next, the inventors investigated the effects of intratumoral injection of MVA and MVAΔE3L on metastatic growth using a murine B16-F10 melanoma bilateral implantation model. Briefly, B16-F10 melanoma cells were implanted intradermally to the left and right flanks of C57B/6 mice (5×10⁵ to the right flank and 1×10⁵ to the left flank). 8 days after tumor implantation, the inventors intratumorally injected MVA or MVAΔE3L (2×10⁷ pfu) or PBS to the larger tumors on the right flank twice weekly. The tumor sizes were measured and the survival of mice was monitored (FIG. 17).

Whereas the PBS-treated mice died quickly with increasing tumor growth over the next 10-14 days (FIGS. 17A and B), mice treated with MVA and MVAΔE3L exhibited delayed tumor growth of both the injected and non-injected tumors at the contralateral side (FIG. 17A-F).

Figure 17G:
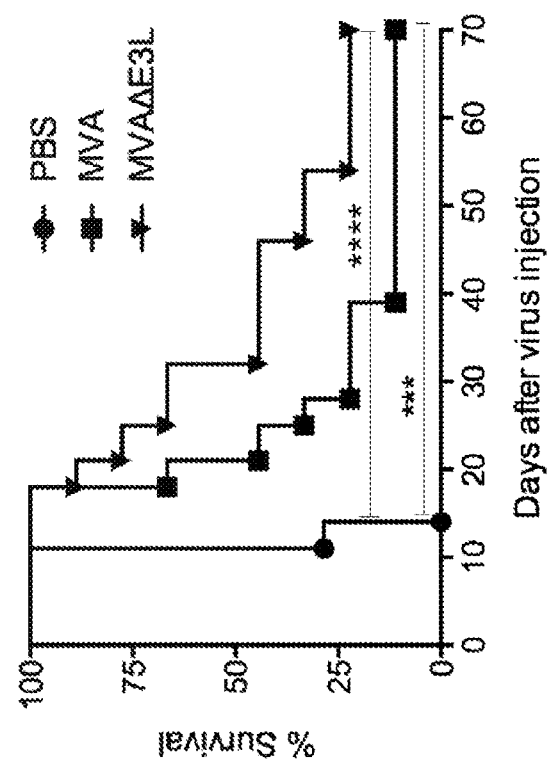

The ability to control the growth of non-injected distant tumors correlated with the improved survival of animals treated with MVA and MVAΔE3L (FIG. 17G, *, P<0.001 for MVA vs. PBS, **, P<0.0001 for MVAΔE3L vs. PBS). Collectively, these results illustrate the soundness of a therapeutic approach for the treatment of metastatic solid tumors.

Example 20

Figure 18D:
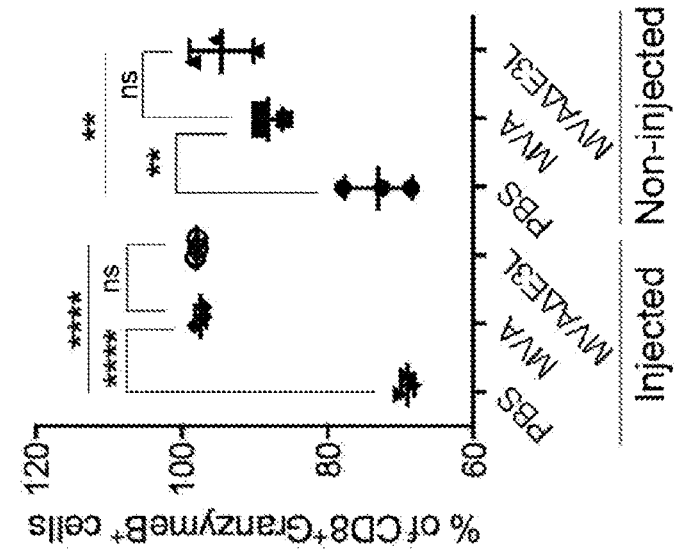
Figure 18C:
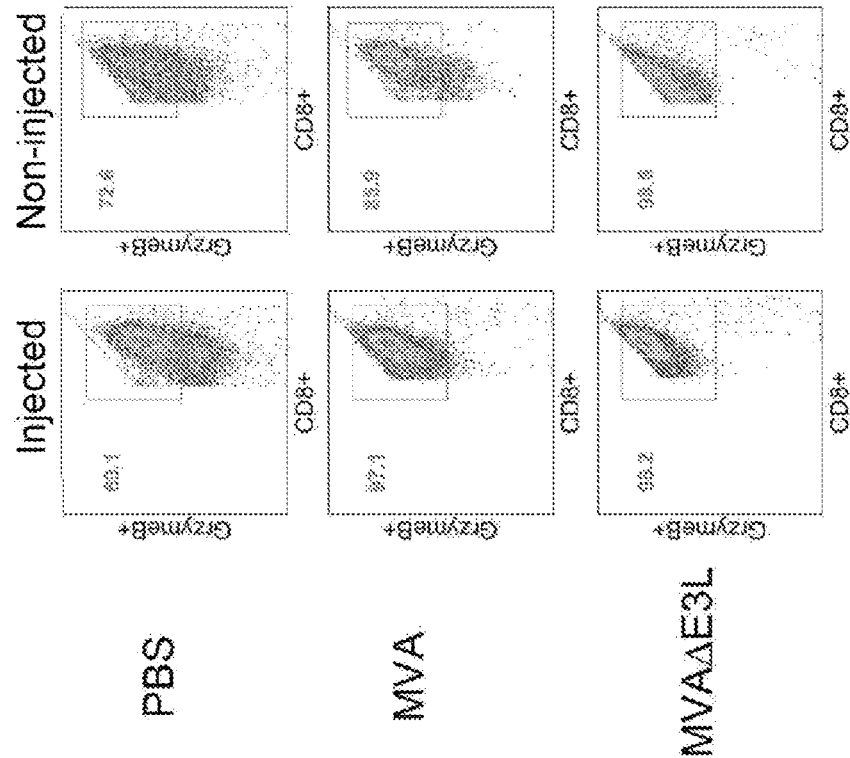
Figure 18F:
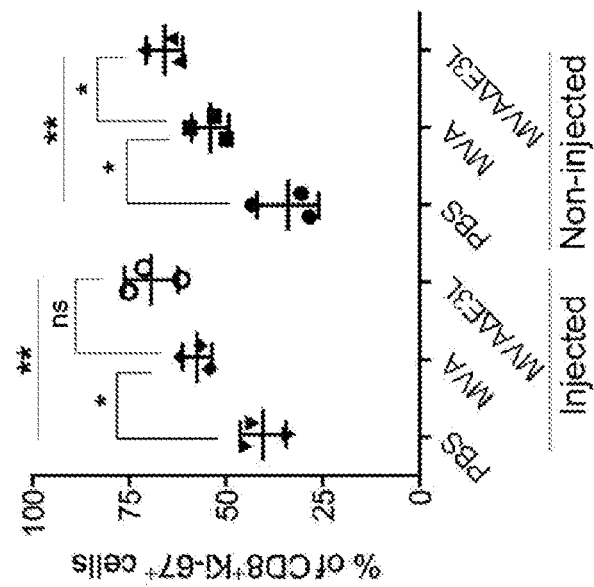
Figure 18E:
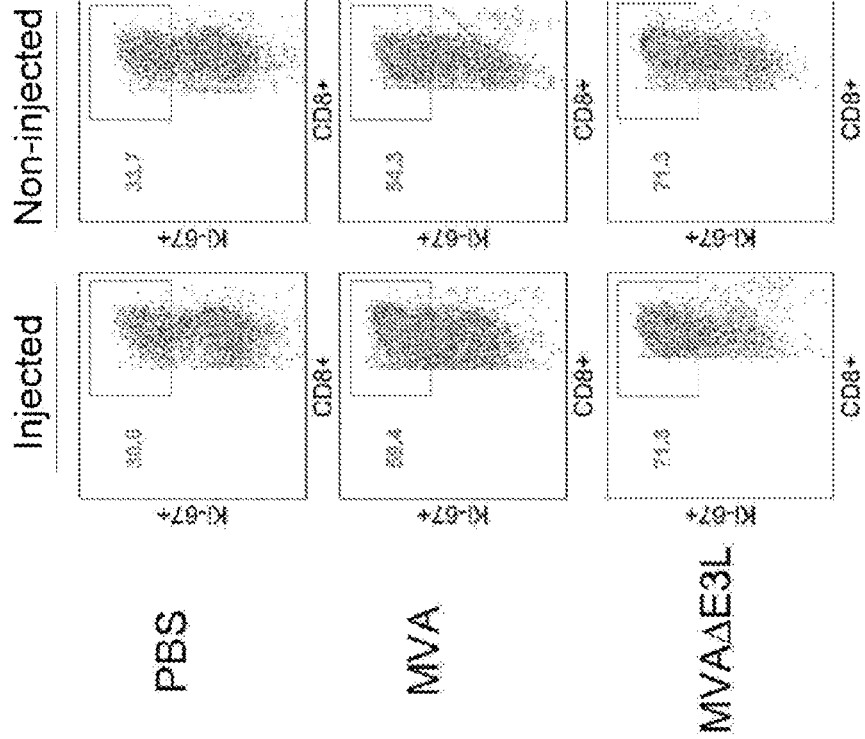
Figure 18J:
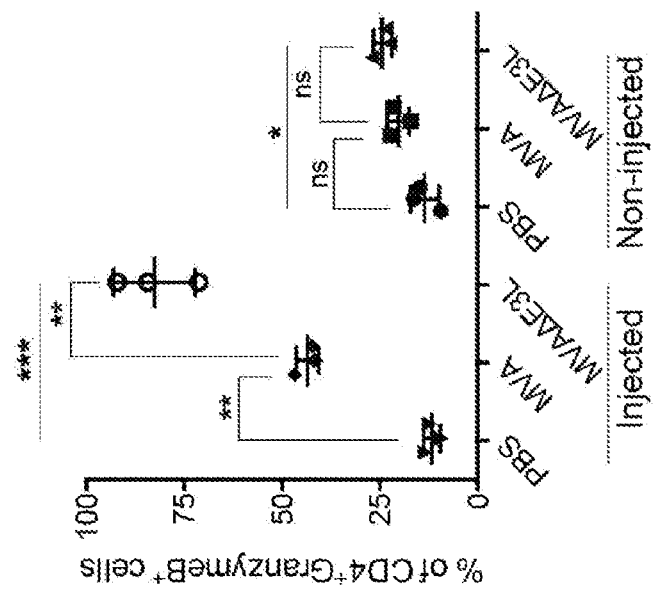
Figure 18I:
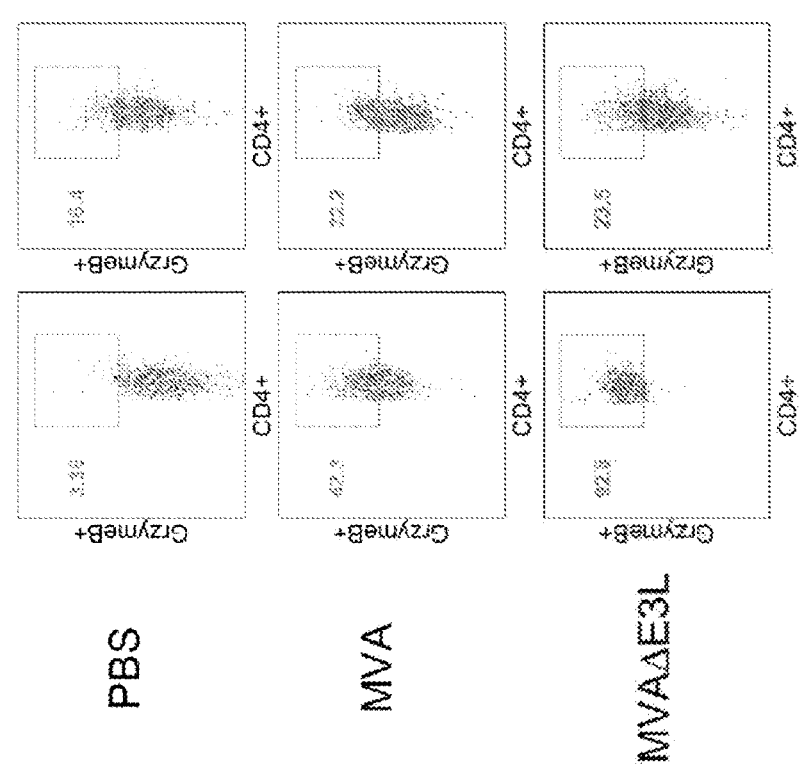
Figure 18L:
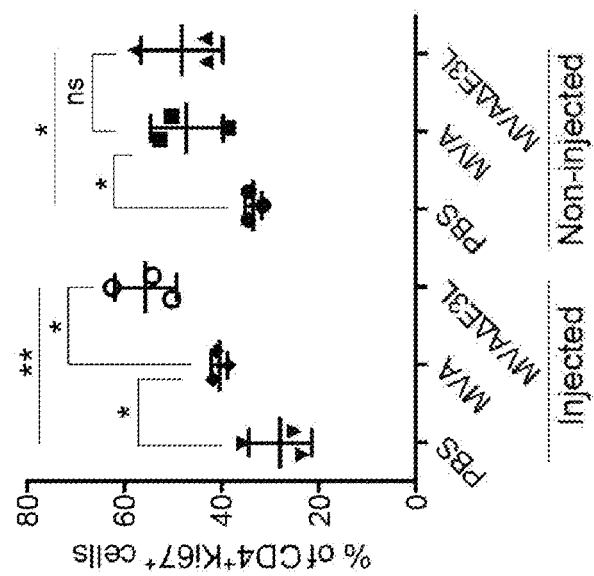
Figure 18K:
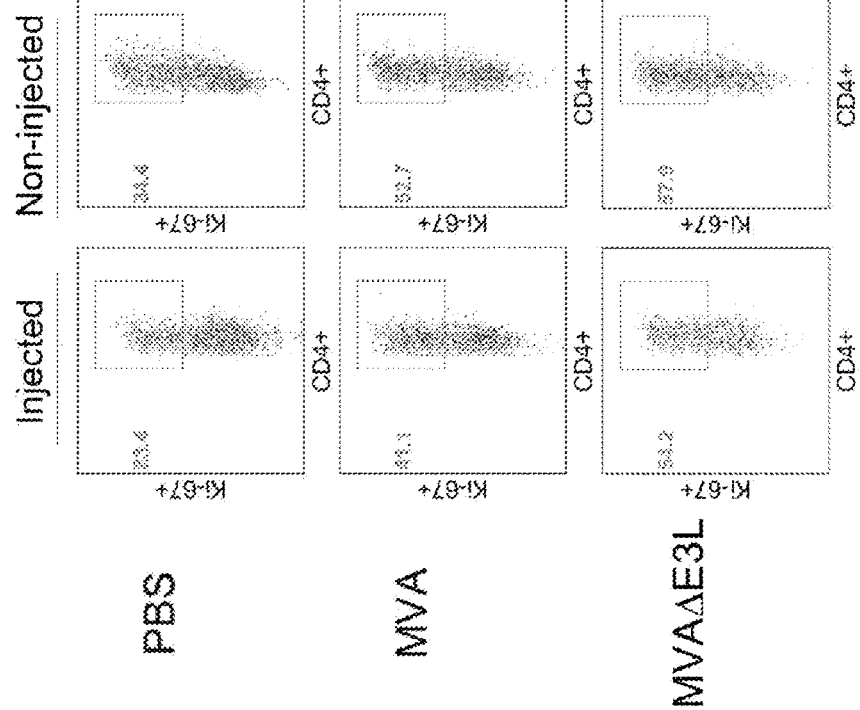

Intratumoral Injection of MVA and MVAΔE3L Leads to Immunological Changes in Both Injected and Non-Injected Distant Tumors To understand the immune mechanisms underlying the antitumor effects of MVA and MVAΔE3L, the inventors investigated the immune cell infiltrates in both injected and non-injected tumors in MVA or MVAΔE3L-treated mice compared with PBS control. Briefly, $2.5 \times 10^5$ B16-F10 melanoma cells were intradermally implanted to the left flank and $5 \times 10^5$ B16-F10 melanoma cells to the right flank of the mice. 7 days post implantation, $2 \times 10^7$ pfu of MVA, or MVAΔE3L, or PBS were injected into the larger tumors on the right flank. The injection was repeated three days later. The non-injected tumors were harvested and cell suspensions were generated. The live immune cell infiltrates in the tumors were analyzed by flow cytometry (FACS). The inventors observed a dramatic increase of $CD8^+$ $CD3^+$ immune cells in both injected and non-injected tumors of mice treated with MVA or MVAΔE3L compared with those in mice treated with PBS (FIGS. 18A and B). MVAΔE3L is more effective than MVA in the recruitment of $CD8^+$ $CD3^+$ in both injected and non-injected tumors (FIGS. 18A and B). MVA or MVAΔE3L-treatment resulted in the increase of numbers of Granzyme B expressing $CD8^+$ and $CD4^+$ T cells in both injected and non-injected tumors (FIGS. 18C, D, I, and J). In addition, MVA or MVAΔE3L-treatment resulted in the proliferation of effector $CD8^+$ and $CD4^+$ T cells in both injected and non-injected tumors as measured by the expression of proliferation marker Ki-67 (FIGS. 18E, F, K, and L). Finally, intratumoral injection of MVA and MVAΔE3L resulted in the reduction of the percent of FoxP3-expressing $CD4^+$ T cells in the injected and non-injected tumors (FIGS. 18G and H). These results indicate that both MVA and MVAΔE3L are capable of the recruitment, activation, and induction of proliferation of effector $CD8^+$ and $CD4^+$ ' as well as the reduction of the immune suppressive regulatory $CD4^+$ T cells in the injected and non-injected tumors. This correlates with their efficacies in eradicating or delaying the growth of injected and non-injected tumors and prolongation of survival. In most cases, MVAΔE3L is more potent than MVA in the induction of immunological changes within injected and non-injected tumors. This could be due to the enhanced abilities of MVAΔE3L in the induction of type I IFN in immune cells, tumor cells, as well as stromal cells compared with MVA.

Example 21

Intratumoral Injection of MVA and MVAΔE3L Leads to Dramatic Reduction of Tumor-Associated Macrophages in the Injected Tumors To investigate whether tumor-associated macrophages (TAM) in melanoma tumors were influenced by MVA or MVAΔE3L therapy, the inventors applied panels of antibodies to define TAM based on the strategy reported previously (Broz et al., Cancer Cell 2014). Generally, live $CD45^+$ and $Ly6C^-$ cells were first defined. Within $MHCII^+$ cells, macrophages were distinguished from DCs based on $CD24^{hi}$ and $F4/80^{lo}$ expression. The TAM populations further revealed two types of macrophages (TAM1 and TAM2) by differential expression of CD11c and CD11b. After MVA or MVAΔE3L therapy, TAM population was decreased in melanoma tumor compared with control (FIGS. 19A and B). Meanwhile, both TAM1 and TAM2 populations were declined to low levels (FIGS. 19A, C, and D). These observations indicate that intratumor injection of MVA and MVAΔE3L leads to reduction of TAMs, which induce immune suppressive effects within tumor microenvironment.

Prophetic Example 22

The Combination of Intratumoral Injection of MVA or MVAΔE3L With Intraperitoneal Delivery of Immune Checkpoint Blockade Antibody in a Unilateral Melanoma Implantation Model Intratumoral injection of the present viruses will be used to enhance therapeutic effects of current immunotherapies, such as the blockade of immune checkpoints (for example, anti-CTLA-4 antibody), tumor-bearing mice will be treated with intratumoral injection of MVA or MVAΔE3L in combination with intraperitoneal delivery of anti-CTLA-4 antibody. Briefly, B16-F10 melanoma cells ($2 \times 10^5$) will be implanted intradermally into the right flank of WT C57B/6 mice. Ten days following tumor implantation, when the tumors have grown larger than those in Example 11, mice will be treated with the following combinations: PBS+isotype control, PBS+anti-CTLA-4 antibody, MVA+isotype control, MVA+anti-CTLA-4, MVAΔE3L+isotype control, and MVAΔE3L+anti-CTLA. The inventors will ensure that the tumor volume is consistent among tested groups at the start of the virus injections. It is anticipated that the treatment with MVA and anti-CTLA-4 antibody, or MVAΔE3L and anti-CTLA-4 antibody will lead to superior therapeutic efficacy compared to either immune checkpoint blockade alone or MVA or MVAΔE3L treatment alone.

Prophetic Example 23

The Combination of Intratumoral Injection of MVA or MVAΔE3L With Intraperitoneal Delivery of Immune Checkpoint Blockade in a Bilateral Melanoma Implantation Model The inventors will also intratumorally inject MVA or MVAΔE3L enhances therapeutic effects of immune checkpoint blockade therapy such as anti-CTLA-4, anti-PD-1, or anti-PD-L1 antibodies in a bilateral B16-F10 melanoma model, which also simulates an individual with metastatic disease. Briefly, B16-F10 melanoma cells will be implanted intradermally to the left and right flanks of C57B/6 mice ($5 \times 10^5$ to the right flank and $1 \times 10^5$ to the left flank). 8 days after tumor implantation, MVA or MVAΔE3L will be intratumorally injected ($2 \times 10^7$ pfu of MVA or MVAΔE3L) or PBS to the larger tumors on the right flank twice weekly. Four groups of mice were treated with MVA and four groups with MVAΔE3L, with each group receiving intraperitoneal delivery of either isotype control, or anti-CTLA-4, or anti-PD-1, or anti-PD-L1 antibodies.

The inventors anticipate that the combination of intratumoral injection of MVA or MVAΔE3L and systemic delivery of checkpoint inhibitors (represented by anti-CTLcomA-4, anti-PD-1 and anti-PD-L1 antibodies) will further delay growth or eradicate the non-injected tumors compared to intratumoral injection of either checkpoint inhibitor alone or MVA or MVAΔE3L alone.

It is anticipated that the results will show that intratumoral delivery of MVA or MVAΔE3L overcomes treatment resistance to immune checkpoint blockade in a metastatic B16 melanoma model which portends well for transferring this approach to human therapy with beneficial results.

Prophetic Example 24

Combination of Intratumoral Injection of MVA or MVAΔE3L With Intraperitoneal Delivery of Immune Checkpoint Blockade in a Bilateral MC38 Colon Adenocarcinoma Implantation Model The inventors will further perform experiments involving intratumoral injection of MVA or MVAΔE3L enhances therapeutic effects of immune checkpoint blockade therapy such as anti-CTLA-4, anti- or anti-PD-L1 antibodies in other bilateral tumor implantation model, which simulates an individual with metastatic disease. Briefly, MC38 colon adenocarcinoma cells will be implanted intradermally to the left and right flanks of C57B/6 mice ($5\times10^5$ to the right flank and $1\times10^5$ to the left flank). 8 days after tumor implantation, MVA or MVAΔE3L will be intratumorally injected ($2\times10^7$ pfu of MVA or MVAΔE3L) or PBS to the larger tumors on the right flank twice weekly. Three groups of mice will be treated with PBS, with each group receiving intraperitoneal delivery of isotype control, or anti-CTLA-4, or anti-PD-L1 antibodies. There will be additional three groups of mice that will be treated with MVA, with each group receiving intraperitoneal delivery of either isotype control, or anti-CTLA-4, or anti-PD-L1 antibodies. Finally, mice treated with MVAΔE3L will be divided into three groups, with each group treated with either isotype control, or anti-CTLA-4, or anti-PD-L1 antibodies. Each group will then be divided into a subgroup also treated with MVA or MVAΔE3L. Controls treated with virus alone will also be provided.

Tumor volume of both injected and non-injected tumors of each group of mice will be monitored and evaluated. Additionally, the inventors will monitor the survival of each treatment group.

It is anticipated that the combination of intratumoral delivery of MVA or MVAΔE3L with checkpoint blockade represented by intraperitoneal delivery of anti-CTLA-4 antibody or intratumoral delivery of MVA or MVAΔE3L with intraperitoneal delivery of anti-PD-1/PD-L1 will lead to eradication of non-injected distant tumors at a higher efficiency than MVA or MVAΔE3L. Thus, it is anticipated that these results show improvement to the treatment of metastatic solid tumors using a combination of MVA or MVAΔE3L and immune checkpoint blockade compared to either checkpoint blockade alone or virus alone. More specifically, it is anticipated that both injected and noninjected tumors will be reduced in size and even eradicated to a degree greater than that achieved with either type of monotherapy and that the results will persist for at least 45 days an longer, thereby validating the combination approach for primary and metastatic solid tumor treatment.

Prophetic Example 25

Combination of Intratumoral Injection of MVA or MVAΔE3L With Intratumoral Delivery of Immune Checkpoint Blockade Anti-CTLA-4 Antibody in a Bilateral B16-F10 Implantation Model In Prophetic Examples 22, 23, and 24, the inventors will test the combination of intratumoral injection of MVA or MVAΔE3L with systemic delivery of immune checkpoint blockade in both melanoma and colon adenocarcinoma models. In this Example, the inventors will test whether the co-administration of MVA or MVAΔE3L and checkpoint blockade represented by anti-CTLA-4 antibody (at 1/10 of dose used for intraperitoneal delivery) will achieve antitumor effects in a stringent bilateral tumor implantation model. Briefly, B16-F10 melanoma cells will be implanted intradermally to the left and right flanks of C57B/6 mice ($5\times10^5$ to the right flank and $1\times10^5$ to the left flank). 8 days after tumor implantation, MVA or MVAΔE3L will be intratumorally injected ($2\times10^7$ pfu of MVA or MVAΔE3L or PBS) into the larger tumors on the right flank twice weekly. Three groups of mice will be treated with MVA, with each group receiving: (i) intraperitoneal delivery of anti-CTLA-4 (100 µg/mouse) (ii) intratumoral delivery of isotype antibody (10 µg/mouse), or (iii) intratumoral delivery of anti-CTLA-4 antibody (10 µg/mouse). Additional three groups of mice will be treated with MVAΔE3L, with each group receiving: (i) intraperitoneal delivery of anti-CTLA-4 (100 µg/mouse) (ii) intratumoral delivery of isotype antibody (10 µg/mouse), or (iii) intratumoral delivery of anti-CTLA-4 antibody (10 µg/mouse).

Tumor volumes of both injected and non-injected tumors will be monitored and evaluated. The inventors anticipate that the intratumoral co-injection of MVA or MVAΔE3L and checkpoint blockade (anti-CTLA-4 antibody at 10 µg/mouse) will be comparable to the therapeutic effects of the combination of intratumoral injection of MVA or MVAΔE3L and intraperitoneal delivery of anti-CTLA-4 antibody (100 µg/mouse). It is anticipated that co-administration of MVA or MVAΔE3L and an immune checkpoint blockade at a substantially lower dose can achieve similar systemic antitumor effects to the combination of intratumoral delivery of MVA or MVAΔE3L with systemic delivery of anti-CTLA-4 antibody at a higher dose.

The above specification, examples and data provide a complete description of the manufacture and use of the composition of the invention. However, these are illustrative and nonlimiting. The breadth of the present invention resides in the claims.

All patent and literature documents cited herein are incorporated by reference in their entirety for all purposes. Any embodiment or claim feature disclosed herein can be disclaimed in Applicant's discretion.

What is claimed is:

1. A method of eliciting an immune response in a subject with a solid malignant tumor, the method comprising delivering to the tumor cells a therapeutically effective amount of a modified vaccinia Ankara virus with deletion of vaccinia virulence factor E3 (MVAΔE3L).

2. The method of claim 1, wherein the delivering results in the treatment of the tumor, wherein the tumor is a carcinoma.

3. The method of claim 1, wherein the delivering results in one or more of the following:
inducing the immune system of the subject to mount an immune response against the tumor or enhance an ongoing response by the immune system against the tumor;
reducing the size of the tumor;
eradicating the tumor;
inhibiting growth of the tumor;
inhibiting metastasis of the tumor;
reducing or eradicating metastatic tumor;
inducing apoptosis of the tumor cells; and
prolonging survival of the subject as compared to an untreated control subject.

4. The method of claim 1, wherein the tumor includes tumor located at the site of MVAΔE3L delivery, or tumor located elsewhere in the body of the subject, or tumor located both at the site and elsewhere in the body of the subject.

5. The method of claim 1, wherein the MVAΔE3L does not comprise a heterologous nucleic acid encoding or expressing a tumor antigen.

6. A method of eliciting an immune response in a subject with a solid malignant tumor, the method comprising delivering to the tumor cells of the subject a therapeutically effective amount of a modified vaccinia Ankara virus with deletion of vaccinia virulence factor E3 (MVAΔE3L), and conjointly administering to the subject a therapeutically effective amount of an immune checkpoint blocking agent or an immune checkpoint agonist.

7. The method of claim 6, wherein the tumor is a carcinoma.

8. The method of claim 6, wherein the MVAΔE3L is delivered parenterally, intratumorally, intravenously, and/or intraperitoneally to the subject, and wherein the immune checkpoint blocking agent or immune checkpoint agonist is administered parenterally, intratumorally, intravenously, and/or intraperitoneally to the subject.

9. The method of claim 6, wherein the immune checkpoint blocking agent is selected from the group consisting of PD-1 inhibitors, PD-L1 inhibitors, CTLA4 inhibitors, inhibitory antibodies against LAG-3 (lymphocyte activation gene 3), TIM3 (T cell Immunoglobulin and Mucin-3), B7-H3, and TIGIT (T-cell immunoreceptor with Ig and ITIM domains); and the immune checkpoint agonist is selected from the group consisting of anti-ICOS antibody, anti-OX40 antibody, agonist antibody against 4-1BB (CD137), and agonist antibody against GITR.

10. The method of claim 6, wherein the virus is delivered to the subject separately, sequentially, or simultaneously with the immune checkpoint blocking agent or immune checkpoint agonist.

11. The method of claim 6, wherein one or both of the virus and the immune checkpoint blocking agent or immune checkpoint agonist are respectively delivered and administered during a period of time of several weeks, months, or years, or indefinitely as long as benefits persist or a maximum tolerated dose is reached.

12. The method of claim 6, wherein the virus is delivered at a dosage per administration of about $10^5$ to about $10^{10}$ plaque-forming units (pfu).

13. The method of claim 6, wherein the MVAΔE3L does not comprise a heterologous nucleic acid encoding or expressing a tumor antigen.

* * * * *